US010815297B2

(12) United States Patent
Bültmann et al.

(10) Patent No.: US 10,815,297 B2
(45) Date of Patent: Oct. 27, 2020

(54) ANTAGONISTS OF IL17C FOR THE TREATMENT OF INFLAMMATORY DISORDERS

(71) Applicants: MorphoSys AG, Planegg (DE); Galapagos NV, Mechelen (DE)

(72) Inventors: Andreas Bültmann, Planegg (DE); Robert Mühlbacher, Geretsried/Gelting (DE); Teresa Garcia, Romainville (FR); Reginald Christophe Xavier Brys, Romainville (FR); Luc Nelles, Mechelen (BE); Katja Conrath, Mechelen (BE)

(73) Assignees: MORPHOSYS AG, Planegg (DE); GALAPAGOS NV, Mechelen (BE)

( * ) Notice: Subject to any disclaimer, the term of this patent is extended or adjusted under 35 U.S.C. 154(b) by 43 days.

(21) Appl. No.: 16/184,390

(22) Filed: Nov. 8, 2018

(65) Prior Publication Data

US 2019/0062422 A1 Feb. 28, 2019

Related U.S. Application Data

(63) Continuation of application No. 14/351,162, filed as application No. PCT/EP2012/070736 on Oct. 19, 2012, now abandoned.

(60) Provisional application No. 61/548,744, filed on Oct. 19, 2011.

(30) Foreign Application Priority Data

Oct. 19, 2011 (EP) .................................... 11185763

(51) Int. Cl.

*C07K 16/24* (2006.01)
*A61K 39/395* (2006.01)
*A61K 39/00* (2006.01)

(52) U.S. Cl.

CPC ........ *C07K 16/244* (2013.01); *A61K 39/3955* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/76* (2013.01); *C07K 2317/92* (2013.01)

(58) Field of Classification Search

None

See application file for complete search history.

(56) References Cited

U.S. PATENT DOCUMENTS

2004/0197306 A1 10/2004 Gorman
2006/0142192 A1 6/2006 Gao ..................... A61K 39/395 530/350
2007/0129302 A1 6/2007 Gao ................... C07K 14/7155 435/69.1
2008/0045698 A1 2/2008 Gorman ............... C07K 14/715 530/387.3
2012/0201821 A1 6/2012 Gonzalez, Jr. ..... C07K 16/2866 424/135.1

FOREIGN PATENT DOCUMENTS

WO 99060127 11/1999
WO 200146420 6/2001
WO 2005065711 7/2005
WO 2008049070 4/2008
WO 2011044563 4/2011
WO 2012061129 5/2012
WO WO2013/016220 1/2013

OTHER PUBLICATIONS

Farady et al. "Improving the species cross-reactivity of an antibody using computation design" Biorg Med Chem Lett 2009 19(14):3744-3747.
Hajighasemi et al. "Production and Characterization of Mouse Monoclonal Antibodies Recognizing Human Pan-IgG Specific Conformational or Linear Epitopes" Avicenna Journal of Medical Biotechnology 2012 4(4):170-177.
Popkov et al. "Human/mouse cross-reactive anti-VEGF receptor 2 recombinant, antibodies selected from an immune b9 allotype rabbit antibody library" Journal of Immunological Methods 2004 288:149-164.
Pappu , Genentech, Inc. Immunology 2011 Blackwell Publishing Ltd, Immunology, 134, 8-16.
Ramirez-Carrozzi, et al.: IL-17C regulates the innate immune function of epitheliell cells in an autocrine manner, Nature Immunology, vol. 12, No. 12, Oct. 12, 2011.
Yamaguchi et al. (2007) J. Immunol 179, 7128-36.
Leonardi Craig, N Engl J Med 2012;366:1190-9.
Chang et al. (2011) Immunity 35, 1-11.
Calhoun, D. ; Generation of Proof of Concept Molecules Neutralitzing Monoclonal Antibodies to IL17Cm, Honors Baccalaureate of Science in Biochemistry and Biophysics (Honors Scholar), Presented Jun. 8, 2007.
Li et al. (2000) Proc. Natl. Acad. Sci. U. S. A. 97, 773-8.
Gaffen (2009) Nat Rev. Immunol 9, 556-67.
Hwang & Kim (2005) Mol Cells 19, 180,184.
Pappu 2012 Elsevier Ltd. Trends in Immunology, Jul. 2012, Cvol. 33, No. 7.
Song, 2011 advance online publication nature immunology.
EP 11 185763.7, Extended European Search Report dated Jun. 1, 2012.

(Continued)

*Primary Examiner* — Bridget E Bunner
(74) *Attorney, Agent, or Firm* — Licata & Tyrrell P.C.

(57) ABSTRACT

The present invention provides antagonists of IL17C for use in the treatment of an inflammatory disorder.

8 Claims, 16 Drawing Sheets

Specification includes a Sequence Listing.

(56) References Cited

OTHER PUBLICATIONS

PCT/EP2012/070736, International Search Report dated Jan. 2, 2013.
PCT/EP2012/070736, Written Opinion of the International Preliminary Examining Authority dated Sep. 11, 2013.
PCT/EP 2012/070736, International Preliminary Report on Patentability dated Jan. 24, 2014.
Johansen C., et al. "Characterization of the interleukin-17 isoforms and receptors in lesional psoriatic skin", British Journal of Dermatology, vol. 160, No. 2, Feb. 2009, pp. 319-324.
Papp Kim, et al. "Brodalumab, an anti-interleukin-17-receptor antibody psoriasis"; The new England Journal of Medicine; Mar. 29, 2012, vol. 366; No, 13, p. 1181-1189.
Brummell et al, Biochemistry; 1993; vol. 32, pp. 1180-1187.
Kobayashi et al. Protein Engineering; 1999; vol. 12, pp. 879-844.
Brorson et al. J. Immunol; 1999; vol. 163, pp. 6694-6701.
Coleman Research in Immunol; 1994; vol. 145; pp. 33-36.

■ rat anti-mIL-17C (311522) IgG2a
▲ rat anti-mIL-17C (311523) IgG2a
▼ rat anti-mIL-17C (8B28) IgG2a
♦ irrelevant rat anti-mouse IgG1
— soluble murine IL-17RE/Fc

FIG. 2

| | | | h/m IgG2a | | |
|---|---|---|---|---|---|
| HCDR3 family | MOR | VL | SEC monomer portion [%] | yield culture purified [mg/l] | Comments |
| 1 | **12740** | lambda | 93 | 9 | low concentration |
| 2 | **12741** | lambda | 95 | 23 | |
| 3 | **12742** | lambda | 8 | 10 | failed in SEC |
| 4 | **12743** | lambda | 98 | 23 | |
| 4 | **12744** | lambda | 98 | 16 | |
| 4 | **12745** | lambda | 94 | 28 | |
| 4 | **12746** | lambda | 99 | 18 | |
| 5 | **12751** | lambda | 96 | 19 | |
| 6 | **12753** | lambda | 92 | 3 | low concentration |
| 7 | **12754** | kappa | 93 | 28 | |
| 8 | **12755** | lambda | 96 | 26 | |
| 9 | **12756** | lambda | 92 | 25 | |
| 10 | **12757** | kappa | 98 | 22 | |
| 11 | **12758** | lambda | 93 | 29 | |
| 12 | **12759** | kappa | 97 | 18 | |
| 12 | **12760** | kappa | 91 | 17 | |
| 12 | **12761** | kappa | 97 | 24 | |
| 12 | **12762** | kappa | 97 | 28 | |

FIG. 3

| | | | Binding (ELISA) | | | |
|---|---|---|---|---|---|---|
| HCDR3 family | MOR | VL | mIL-17C $EC_{50}$ [nM] n=1-2 | huIL-17C | msIL-17B | lysozyme |
| 1 | **12740** | lambda | 1.14 ± 0.11 | No binding | No binding | No binding |
| 2 | **12741** | lambda | 0.47 ± 0.1 | | | |
| 4 | **12743** | lambda | 0.3 | | | |
| 4 | **12744** | lambda | 0.28 ± 0.1 | | | |
| 4 | **12745** | lambda | 0.4 | | | |
| 4 | **12746** | lambda | 0.38 ±0.25 | | | |
| 5 | **12751** | lambda | 0.39 ± 0.0 | | | |
| 8 | **12754** | kappa | 0.40 ± 0.01 | | | |
| 13 | **12759** | kappa | 0.29± 0.18 | | | |
| 13 | **12760** | kappa | 0.27 ± 0.1 | | | |
| 13 | **12761** | kappa | 0.36 ± 0.15 | | | |
| 13 | **12762** | kappa | 0.4 | | | |

FIG. 4

| | | | Affinity (Fab) |
|---|---|---|---|
| **HCDR3 family** | **MOR** | **VL** | **KD [pM]** |
| 1 | **12740** | lambda | 170 |
| 2 | **12741** | lambda | * |
| 3 | **12742** | lambda | * (not available as IgG2a) |
| 4 | **12743** | lambda | 48 |
| 4 | **12744** | lambda | 53 |
| 4 | **12745** | lambda | 75 |
| 4 | **12746** | lambda | 56 |
| 5 | **12751** | lambda | * |
| 6 | **12753** | lambda | 62 (not available as IgG2a) |
| 7 | **12754** | kappa | 4100 |
| 8 | **12755** | lambda | no signal |
| 9 | **12756** | lambda | no signal |
| 10 | **12757** | kappa | no signal |
| 11 | **12758** | lambda | no signal |
| 12 | **12759** | kappa | 220 |
| 12 | **12760** | kappa | ** |
| 12 | **12761** | kappa | 85 |
| 12 | **12762** | kappa | 96 |

*= no sigmoidal binding
**= Fab precipitates

FIG. 5

| HCDR3 family | MOR | VL | mIL17C - mIL-17RE inhibition assay $IC_{50}$ [pM] |
|---|---|---|---|
| 1 | **12740** | lambda | 3493 ± 142 |
| 2 | **12741** | lambda | incomplete inhibition |
| 4 | **12743** | lambda | 16 ± 5.4 |
| 4 | **12744** | lambda | 12 ± 3.7 |
| 4 | **12745** | lambda | 13 ± 7.3 |
| 4 | **12746** | lambda | 23 ± 13 |
| 5 | **12751** | lambda | 160 ± 93.6 |
| 8 | **12754** | kappa | 8442 ± 1494 |
| 13 | **12759** | kappa | 28 ± 2.7 |
| 13 | **12760** | kappa | 122 ± 43.9 |
| 13 | **12761** | kappa | 24 ± 6 |
| 13 | **12762** | kappa | 9 ± 1.8 |

FIG. 6

| HCDR3 family | MOR | VL | Mouse Serum Stability Assay 24h/37°C Coefficient of variation |
|---|---|---|---|
| 1 | **12740** | lambda | n.d. |
| 2 | **12741** | lambda | 13.01% |
| 3 | **12743** | lambda | 2.88% |
| 3 | **12744** | lambda | 11.78% |
| 3 | **12745** | lambda | 15.94% |
| 3 | **12746** | lambda | 7.36% |
| 4 | **12751** | lambda | 3.75% |
| 5 | **12754** | kappa | 17.00% |
| 6 | **12759** | kappa | 8.80% |
| 6 | **12760** | kappa | 35.31% |
| 6 | **12761** | kappa | 1.23% |
| 6 | **12762** | kappa | 2.43% |

*p<0.05, p<0.01, *p<0.0001 vs IMQ Control with Anova, Dunnett's-Test

```
                         SEQUENCE LISTING


<160> NUMBER OF SEQ ID NOS: 186

<210> SEQ ID NO 1
<211> LENGTH: 10
<212> TYPE: PRT
<213> ORGANISM: Artificial Sequence
<220> FEATURE:
<223> OTHER INFORMATION: HCDR1

<400> SEQUENCE: 1

Gly Gly Thr Phe Ser Ile Tyr Ala Ile Ser
1               5                   10


<210> SEQ ID NO 2
<211> LENGTH: 20
<212> TYPE: PRT
<213> ORGANISM: Artificial Sequence
<220> FEATURE:
<223> OTHER INFORMATION: HCDR2

<400> SEQUENCE: 2

Trp Met Gly Gly Ile Ile Pro Ile Leu Gly Ile Ala Asn Tyr Ala Gln
1               5                   10                  15

Lys Phe Gln Gly
            20


<210> SEQ ID NO 3
<211> LENGTH: 10
<212> TYPE: PRT
<213> ORGANISM: Artificial Sequence
<220> FEATURE:
<223> OTHER INFORMATION: HCDR3

<400> SEQUENCE: 3

Asp Ala Thr His Ser Tyr Tyr His Asp Tyr
1               5                   10


<210> SEQ ID NO 4
<211> LENGTH: 14
<212> TYPE: PRT
<213> ORGANISM: Artificial Sequence
<220> FEATURE:
<223> OTHER INFORMATION: LCDR1

<400> SEQUENCE: 4
```

-continued

Thr Gly Thr Ser Ser Asp Val Gly Ser Tyr Glu Thr Val Ser
1 5 10

<210> SEQ ID NO 5
<211> LENGTH: 11
<212> TYPE: PRT
<213> ORGANISM: Artificial Sequence
<220> FEATURE:
<223> OTHER INFORMATION: LCDR2

<400> SEQUENCE: 5

Val Met Ile Tyr Glu Val Ser Asp Arg Pro Ser
1 5 10

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gly Ser Phe Ala His Trp Gly Ser Trp
1 5

<210> SEQ ID NO 7
<211> LENGTH: 112
<212> TYPE: PRT
<213> ORGANISM: Artificial Sequence
<220> FEATURE:
<223> OTHER INFORMATION: VL

<400> SEQUENCE: 7

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Glu Thr Val Ser Trp Tyr Gln Gln His Pro Gly Lys Ala Pro Lys Val
35 40 45

Met Ile Tyr Glu Val Ser Asp Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Gly Ser Phe Ala His Trp
85 90 95

Gly Ser Trp Val Phe Gly Gly Gly Thr Lys Leu Thr Val Leu Gly Gln
100 105 110

<210> SEQ ID NO 8
<211> LENGTH: 119
<212> TYPE: PRT
<213> ORGANISM: Artificial Sequence
<220> FEATURE:
<223> OTHER INFORMATION: VH

<400> SEQUENCE: 8

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ile Tyr
20 25 30

Ala Ile Ser Trp Val Arg Gln Ala Pro Gly Gln Gly Leu Glu Trp Met
35 40 45

-continued

```
Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Thr His Ser Tyr Tyr His Asp Tyr Trp Gly Gln Gly
            100                 105                 110

Thr Leu Val Thr Val Ser Ser
        115


<210> SEQ ID NO 9
<211> LENGTH: 336
<212> TYPE: DNA
<213> ORGANISM: Artificial Sequence
<220> FEATURE:
<223> OTHER INFORMATION: VL DNA

<400> SEQUENCE: 9

gatatcgcgc tgacccagcc ggcgagcgtg agcggtagcc cgggccagag cattaccatt      60

agctgcaccg gcaccagcag cgatgtgggc tcttacgaaa ctgtgtcttg gtaccagcag     120

catccgggca aggcgccgaa agttatgatc tacgaagttt ctgaccgtcc gagcggcgtg     180

agcaaccgtt ttagcggatc caaaagcggc aacaccgcga gcctgaccat tagcggcctg     240

caagcggaag acgaagcgga ttattactgc ggttctttcg ctcattgggg ttcttgggtg     300

tttggcggcg gcacgaagtt aaccgttctt ggccag                               336


<210> SEQ ID NO 10
<211> LENGTH: 357
<212> TYPE: DNA
<213> ORGANISM: Artificial Sequence
<220> FEATURE:
<223> OTHER INFORMATION: VH DNA

<400> SEQUENCE: 10

caggtgcaat tggtgcagag cggtgccgaa gtgaaaaaac cgggcagcag cgtgaaagtt      60

agctgcaaag catccggagg gacgttttct atctacgcta tctcttgggt gcgccaggcc     120

ccgggccagg gcctcgagtg gatgggcggt atcatcccga tcctgggcat cgcgaactac     180

gcccagaaat ttcagggccg ggtgaccatt accgccgatg aaagcaccag caccgcctat     240

atggaactga gcagcctgcg cagcgaagat acggccgtgt attattgcgc gcgtgacgct     300

actcattctt actaccatga ttactggggc caaggcaccc tggtgactgt tagctca       357


<210> SEQ ID NO 11
<211> LENGTH: 10
<212> TYPE: PRT
<213> ORGANISM: Artificial Sequence
<220> FEATURE:
<223> OTHER INFORMATION: HCDR1

<400> SEQUENCE: 11

Gly Gly Thr Phe Ser Ser Tyr Ala Ile Ser
1               5                   10


<210> SEQ ID NO 12
<211> LENGTH: 20
<212> TYPE: PRT
<213> ORGANISM: Artificial Sequence
<220> FEATURE:
<223> OTHER INFORMATION: HCDR2
```

<400> SEQUENCE: 12

```
Trp Met Gly Met Ile Met Pro Glu Val Gly Met Ala Asp Tyr Ala Gln
1               5                   10                  15

Lys Phe Gln Gly
            20
```

<210> SEQ ID NO 13
<211> LENGTH: 19
<212> TYPE: PRT
<213> ORGANISM: Artificial Sequence
<220> FEATURE:
<223> OTHER INFORMATION: HCDR3

<400> SEQUENCE: 13

```
Asp Phe Ile Ala Val Gly Ser Leu Glu Ile Trp His Tyr Tyr Tyr Gly
1               5                   10                  15

Leu Asp Val
```

<210> SEQ ID NO 14
<211> LENGTH: 11
<212> TYPE: PRT
<213> ORGANISM: Artificial Sequence
<220> FEATURE:
<223> OTHER INFORMATION: LCDR1

<400> SEQUENCE: 14

```
Ser Gly Asp Asn Ile Gly Glu His Tyr Ala Ser
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: LCDR2

<400> SEQUENCE: 15

```
Leu Val Ile Ser Tyr Asp Asn Glu Arg Pro Ser
1               5                   10
```

<210> SEQ ID NO 16
<211> LENGTH: 10
<212> TYPE: PRT
<213> ORGANISM: Artificial Sequence
<220> FEATURE:
<223> OTHER INFORMATION: LCDR3

<400> SEQUENCE: 16

```
Gln Ser Trp Thr Ser Gln Lys Pro Asp Tyr
1               5                   10
```

<210> SEQ ID NO 17
<211> LENGTH: 110
<212> TYPE: PRT
<213> ORGANISM: Artificial Sequence
<220> FEATURE:
<223> OTHER INFORMATION: VL

<400> SEQUENCE: 17

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Glu His Tyr Ala
            20                  25                  30
```

Ser Trp Tyr Gln Gln Lys Pro Gly Gln Ala Pro Val Leu Val Ile Ser
        35                  40                  45

Tyr Asp Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Thr Ser Gln Lys Pro Asp
                85                  90                  95

Tyr Val Phe Gly Gly Gly Thr Lys Leu Thr Val Leu Gly Gln
            100                 105                 110

<210> SEQ ID NO 18
<211> LENGTH: 128
<212> TYPE: PRT
<213> ORGANISM: Artificial Sequence
<220> FEATURE:
<223> OTHER INFORMATION: VH

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Met Ile Met Pro Glu Val Gly Met Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Ile Ala Val Gly Ser Leu Glu Ile Trp His Tyr Tyr
            100                 105                 110

Tyr Gly Leu Asp Val Trp Gly Gln Gly Thr Leu Val Thr Val Ser Ser
        115                 120                 125

<210> SEQ ID NO 19
<211> LENGTH: 330
<212> TYPE: DNA
<213> ORGANISM: Artificial Sequence
<220> FEATURE:
<223> OTHER INFORMATION: VL DNA

<400> SEQUENCE: 19
gatatcgaac tgacccagcc gccgagcgtg agcgtgagcc cgggccagac cgcgagcatt      60
acctgtagcg gcgataacat cggtgaacat tacgcttctt ggtaccagca gaaaccgggc     120
caggcgccgg tgctggtgat ctcttacgac aacgaacgtc cgagcggcat cccggaacgt     180
tttagcggat ccaacagcgg caacaccgcg accctgacca ttagcggcac ccaggcggaa     240
gacgaagcgg attattactg ccagtcttgg acttctcaga aaccggacta cgtgtttggc     300
ggcggcacga agttaaccgt tcttggccag                                      330

<210> SEQ ID NO 20
<211> LENGTH: 384
<212> TYPE: DNA
<213> ORGANISM: Artificial Sequence
<220> FEATURE:
<223> OTHER INFORMATION: VH DNA

<400> SEQUENCE: 20
caggtgcaat tggtgcagag cggtgccgaa gtgaaaaaac cgggcagcag cgtgaaagtt 60
agctgcaaag catccggagg gacgtttagc agctatgcga ttagctgggt gcgccaggcc 120
ccgggccagg gcctcgagtg gatgggcatg atcatgccgg aagttggcat ggctgactac 180
gcccagaaat ttcagggccg ggtgaccatt accgccgatg aaagcaccag caccgcctat 240
atggaactga gcagcctgcg cagcgaagat acggccgtgt attattgcgc gcgtgacttc 300
atcgctgttg gttctctgga aatctggcat tactactacg gtctggatgt ttggggccaa 360
ggcaccctgg tgactgttag ctca 384

<210> SEQ ID NO 21
<211> LENGTH: 10
<212> TYPE: PRT
<213> ORGANISM: Artificial Sequence
<220> FEATURE:
<223> OTHER INFORMATION: HCDR1

<400> SEQUENCE: 21

Gly Gly Thr Phe Ser Ser Tyr Gly Ile Ser
1 5 10

<210> SEQ ID NO 22
<211> LENGTH: 20
<212> TYPE: PRT
<213> ORGANISM: Artificial Sequence
<220> FEATURE:
<223> OTHER INFORMATION: HCDR2

<400> SEQUENCE: 22

Trp Met Gly Arg Ile Ile Pro Ile Phe Gly Thr Ala Tyr Tyr Ala Gln
1 5 10 15

Lys Phe Gln Gly
20

<210> SEQ ID NO 23
<211> LENGTH: 19
<212> TYPE: PRT
<213> ORGANISM: Artificial Sequence
<220> FEATURE:
<223> OTHER INFORMATION: HCDR3

<400> SEQUENCE: 23

Asp Met Arg Tyr His Asp Tyr Trp Pro Tyr Tyr Tyr Gly Ser Asp Gln
1 5 10 15

Phe Asp Val

<210> SEQ ID NO 24
<211> LENGTH: 13
<212> TYPE: PRT
<213> ORGANISM: Artificial Sequence
<220> FEATURE:
<223> OTHER INFORMATION: LCDR1

<400> SEQUENCE: 24

Ser Gly Ser Ser Ser Asn Ile Gly Ser Asp Ile Val Ser
1 5 10

<210> SEQ ID NO 25
<211> LENGTH: 11
<212> TYPE: PRT
<213> ORGANISM: Artificial Sequence
<220> FEATURE:

<223> OTHER INFORMATION: LCDR2

<400> SEQUENCE: 25

Leu Leu Ile Tyr Tyr Asn Asn Leu Arg Pro Ser
1 5 10

<210> SEQ ID NO 26
<211> LENGTH: 10
<212> TYPE: PRT
<213> ORGANISM: Artificial Sequence
<220> FEATURE:
<223> OTHER INFORMATION: LCDR3

<400> SEQUENCE: 26

Gln Ser Trp Asp Trp Ala Ser Leu Ala Met
1 5 10

<210> SEQ ID NO 27
<211> LENGTH: 112
<212> TYPE: PRT
<213> ORGANISM: Artificial Sequence
<220> FEATURE:
<223> OTHER INFORMATION: VL

<400> SEQUENCE: 27

Asp Ile Val Leu Thr Gln Pro Pro Ser Val Ser Gly Ala Pro Gly Gln
1 5 10 15

Arg Val Thr Ile Ser Cys Ser Gly Ser Ser Ser Asn Ile Gly Ser Asp
20 25 30

Ile Val Ser Trp Tyr Gln Gln Leu Pro Gly Thr Ala Pro Lys Leu Leu
35 40 45

Ile Tyr Tyr Asn Asn Leu Arg Pro Ser Gly Val Pro Asp Arg Phe Ser
50 55 60

Gly Ser Lys Ser Gly Thr Ser Ala Ser Leu Ala Ile Thr Gly Leu Gln
65 70 75 80

Ala Glu Asp Glu Ala Asp Tyr Tyr Cys Gln Ser Trp Asp Trp Ala Ser
85 90 95

Leu Ala Met Val Phe Gly Gly Gly Thr Lys Leu Thr Val Leu Gly Gln
100 105 110

<210> SEQ ID NO 28
<211> LENGTH: 128
<212> TYPE: PRT
<213> ORGANISM: Artificial Sequence
<220> FEATURE:
<223> OTHER INFORMATION: VH

<400> SEQUENCE: 28

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Gly Ile Ser Trp Val Arg Gln Ala Pro Gly Gln Gly Leu Glu Trp Met
35 40 45

Gly Arg Ile Ile Pro Ile Phe Gly Thr Ala Tyr Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

-continued

```
Ala Arg Asp Met Arg Tyr His Asp Tyr Trp Pro Tyr Tyr Tyr Gly Ser
            100                 105                 110

Asp Gln Phe Asp Val Trp Gly Gln Gly Thr Leu Val Thr Val Ser Ser
        115                 120                 125


<210> SEQ ID NO 29
<211> LENGTH: 336
<212> TYPE: DNA
<213> ORGANISM: Artificial Sequence
<220> FEATURE:
<223> OTHER INFORMATION: VL DNA

<400> SEQUENCE: 29

gatatcgtgc tgacccagcc gccgagcgtg agcggtgcac cgggccagcg cgtgaccatt      60

agctgtagcg gcagcagcag caacattggt tctgacatcg tgtcttggta ccagcagctg     120

ccgggcacgg cgccgaaact gctgatctac tacaacaacc tgcgcccgag cggcgtgccg     180

gatcgcttta gcggatccaa aagcggcacc agcgccagcc tggcgattac cggcctgcaa     240

gcagaagacg aagcggatta ttactgccag tcttgggact gggcttctct ggctatggtg     300

tttggcggcg gcacgaagtt aaccgttctt ggccag                               336


<210> SEQ ID NO 30
<211> LENGTH: 384
<212> TYPE: DNA
<213> ORGANISM: Artificial Sequence
<220> FEATURE:
<223> OTHER INFORMATION: VH DNA

<400> SEQUENCE: 30

caggtgcaat tggtgcagag cggtgccgaa gtgaaaaaac cgggcagcag cgtgaaagtt      60

agctgcaaag catccggagg gacgttttct tcttacggta tctcttgggt gcgccaggcc     120

ccgggccagg gcctcgagtg gatgggccgt atcatcccga tcttcggcac tgcgtactac     180

gcccagaaat ttcagggccg ggtgaccatt accgccgatg aaagcaccag caccgcctat     240

atggaactga gcagcctgcg cagcgaagat acggccgtgt attattgcgc gcgtgacatg     300

cgttaccatg actactggcc gtactactac ggttctgacc agttcgatgt ttggggccaa     360

ggcaccctgg tgactgttag ctca                                            384


<210> SEQ ID NO 31
<211> LENGTH: 10
<212> TYPE: PRT
<213> ORGANISM: Artificial Sequence
<220> FEATURE:
<223> OTHER INFORMATION: HCDR1

<400> SEQUENCE: 31

Gly Tyr Thr Phe Thr Ser Asn Phe Ile His
1               5                   10


<210> SEQ ID NO 32
<211> LENGTH: 20
<212> TYPE: PRT
<213> ORGANISM: Artificial Sequence
<220> FEATURE:
<223> OTHER INFORMATION: HCDR2

<400> SEQUENCE: 32

Trp Met Gly Trp Ile Ser Pro Tyr Asn Gly Asp Thr Asn Tyr Ala Gln
1               5                   10                  15

Lys Phe Gln Gly
```

20

<210> SEQ ID NO 33
<211> LENGTH: 16
<212> TYPE: PRT
<213> ORGANISM: Artificial Sequence
<220> FEATURE:
<223> OTHER INFORMATION: HCDR3

<400> SEQUENCE: 33

Glu Ser Val Tyr Tyr Gly Ser Asp Tyr Gly Tyr Asn Gly Met Asp Ile
1 5 10 15

<210> SEQ ID NO 34
<211> LENGTH: 11
<212> TYPE: PRT
<213> ORGANISM: Artificial Sequence
<220> FEATURE:
<223> OTHER INFORMATION: LCDR1

<400> SEQUENCE: 34

Ser Gly Asp Asn Leu Gly Glu Glu Tyr Val Ser
1 5 10

<210> SEQ ID NO 35
<211> LENGTH: 11
<212> TYPE: PRT
<213> ORGANISM: Artificial Sequence
<220> FEATURE:
<223> OTHER INFORMATION: LCDR2

<400> SEQUENCE: 35

Leu Val Ile Tyr Asp Asp Thr Lys Arg Pro Ser
1 5 10

<210> SEQ ID NO 36
<211> LENGTH: 9
<212> TYPE: PRT
<213> ORGANISM: Artificial Sequence
<220> FEATURE:
<223> OTHER INFORMATION: LCDR3

<400> SEQUENCE: 36

Ala Ser Trp Asp Leu Trp Ser Val Glu
1 5

<210> SEQ ID NO 37
<211> LENGTH: 109
<212> TYPE: PRT
<213> ORGANISM: Artificial Sequence
<220> FEATURE:
<223> OTHER INFORMATION: VL

<400> SEQUENCE: 37

Asp Ile Glu Leu Thr Gln Pro Pro Ser Val Ser Val Ser Pro Gly Gln
1 5 10 15

Thr Ala Ser Ile Thr Cys Ser Gly Asp Asn Leu Gly Glu Glu Tyr Val
20 25 30

Ser Trp Tyr Gln Gln Lys Pro Gly Gln Ala Pro Val Leu Val Ile Tyr
35 40 45

Asp Asp Thr Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

```
Asp Glu Ala Asp Tyr Tyr Cys Ala Ser Trp Asp Leu Trp Ser Val Glu
                85                  90                  95

Val Phe Gly Gly Gly Thr Lys Leu Thr Val Leu Gly Gln
            100                 105


<210> SEQ ID NO 38
<211> LENGTH: 125
<212> TYPE: PRT
<213> ORGANISM: Artificial Sequence
<220> FEATURE:
<223> OTHER INFORMATION: VH

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Phe Ile His Trp Val Arg Gln Ala Pro Gly Gln Gly Leu Glu Trp Met
        35                  40                  45

Gly Trp Ile Ser Pro Tyr Asn Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Val Tyr Tyr Gly Ser Asp Tyr Gly Tyr Asn Gly Met
            100                 105                 110

Asp Ile Trp Gly Gln Gly Thr Leu Val Thr Val Ser Ser
        115                 120                 125


<210> SEQ ID NO 39
<211> LENGTH: 327
<212> TYPE: DNA
<213> ORGANISM: Artificial Sequence
<220> FEATURE:
<223> OTHER INFORMATION: VL DNA

<400> SEQUENCE: 39

gatatcgaac tgacccagcc gccgagcgtg agcgtgagcc cgggccagac cgcgagcatt      60

acctgtagcg gcgataacct gggtgaagaa tacgtttctt ggtaccagca gaaaccgggc     120

caggcgccgg tgctggtgat ctacgacgac actaaacgtc cgagcggcat cccggaacgt     180

tttagcggat ccaacagcgg caacaccgcg accctgacca ttagcggcac ccaggcggaa     240

gacgaagcgg attattactg cgcttcttgg gacctgtggt ctgttgaagt gtttggcggc     300

ggcacgaagt taaccgttct tggccag                                         327


<210> SEQ ID NO 40
<211> LENGTH: 375
<212> TYPE: DNA
<213> ORGANISM: Artificial Sequence
<220> FEATURE:
<223> OTHER INFORMATION: VH DNA

<400> SEQUENCE: 40

caggtgcaat tggtgcagag cggtgcggaa gtgaaaaaac cgggtgccag cgtgaaagtt      60

agctgcaaag cgtccggata taccttcact tctaacttca tccattgggt gcgccaggcc     120

ccgggccagg gcctcgagtg gatgggctgg atctctccgt acaacggcga cacgaactac     180

gcgcagaaat ttcagggccg ggtgaccatg acccgtgata ccagcattag caccgcgtat     240
```

atggaactga gccgtctgcg tagcgaagat acggccgtgt attattgcgc gcgtgaatct 300
gtttactacg gttctgacta cggttacaac ggtatggata tctggggcca aggcaccctg 360
gtgactgtta gctca 375

<210> SEQ ID NO 41
<211> LENGTH: 10
<212> TYPE: PRT
<213> ORGANISM: Artificial Sequence
<220> FEATURE:
<223> OTHER INFORMATION: HCDR1

<400> SEQUENCE: 41

Gly Tyr Thr Phe Thr Ser Asn Phe Ile His
1 5 10

<210> SEQ ID NO 42
<211> LENGTH: 20
<212> TYPE: PRT
<213> ORGANISM: Artificial Sequence
<220> FEATURE:
<223> OTHER INFORMATION: HCDR2

<400> SEQUENCE: 42

Trp Met Gly Trp Ile Ser Pro Tyr Asn Gly Asp Thr Asn Tyr Ala Gln
1 5 10 15

Lys Phe Gln Gly
20

<210> SEQ ID NO 43
<211> LENGTH: 16
<212> TYPE: PRT
<213> ORGANISM: Artificial Sequence
<220> FEATURE:
<223> OTHER INFORMATION: HCDR3

<400> SEQUENCE: 43

Glu Ser Val Tyr Tyr Gly Ser Asp Tyr Gly Tyr Asn Gly Met Asp Ile
1 5 10 15

<210> SEQ ID NO 44
<211> LENGTH: 11
<212> TYPE: PRT
<213> ORGANISM: Artificial Sequence
<220> FEATURE:
<223> OTHER INFORMATION: LCDR1

<400> SEQUENCE: 44

Ser Gly Asp Asn Leu Gly Glu Glu Tyr Val Ser
1 5 10

<210> SEQ ID NO 45
<211> LENGTH: 11
<212> TYPE: PRT
<213> ORGANISM: Artificial Sequence
<220> FEATURE:
<223> OTHER INFORMATION: LCDR2

<400> SEQUENCE: 45

Leu Val Ile Tyr Asp Asp Thr Lys Arg Pro Ser
1 5 10

<210> SEQ ID NO 46
<211> LENGTH: 9
<212> TYPE: PRT

<213> ORGANISM: Artificial Sequence
<220> FEATURE:
<223> OTHER INFORMATION: LCDR3

<400> SEQUENCE: 46

Ala Ser Trp Ala Phe Tyr Ser Ser Gln
1               5

<210> SEQ ID NO 47
<211> LENGTH: 109
<212> TYPE: PRT
<213> ORGANISM: Artificial Sequence
<220> FEATURE:
<223> OTHER INFORMATION: VL

<400> SEQUENCE: 47

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Glu Glu Tyr Val
            20                  25                  30

Ser Trp Tyr Gln Gln Lys Pro Gly Gln Ala Pro Val Leu Val Ile Tyr
        35                  40                  45

Asp Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Ala Phe Tyr Ser Ser Gln
                85                  90                  95

Val Phe Gly Gly Gly Thr Lys Leu Thr Val Leu Gly Gln
            100                 105

<210> SEQ ID NO 48
<211> LENGTH: 125
<212> TYPE: PRT
<213> ORGANISM: Artificial Sequence
<220> FEATURE:
<223> OTHER INFORMATION: VH

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Phe Ile His Trp Val Arg Gln Ala Pro Gly Gln Gly Leu Glu Trp Met
        35                  40                  45

Gly Trp Ile Ser Pro Tyr Asn Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Val Tyr Tyr Gly Ser Asp Tyr Gly Tyr Asn Gly Met
            100                 105                 110

Asp Ile Trp Gly Gln Gly Thr Leu Val Thr Val Ser Ser
        115                 120                 125

<210> SEQ ID NO 49
<211> LENGTH: 327
<212> TYPE: DNA
<213> ORGANISM: Artificial Sequence

<220> FEATURE:
<223> OTHER INFORMATION: VL DNA

<400> SEQUENCE: 49
gatatcgaac tgacccagcc gccgagcgtg agcgtgagcc cgggccagac cgcgagcatt 60
acctgtagcg gcgataacct gggtgaagaa tacgtttctt ggtaccagca gaaaccgggc 120
caggcgccgg tgctggtgat ctacgacgac actaaacgtc cgagcggcat cccggaacgt 180
tttagcggat ccaacagcgg caacaccgcg accctgacca ttagcggcac ccaggcggaa 240
gacgaagcgg attattactg cgcttcttgg gctttctact cttctcaggt gtttggcggc 300
ggcacgaagt taaccgttct tggccag 327

<210> SEQ ID NO 50
<211> LENGTH: 375
<212> TYPE: DNA
<213> ORGANISM: Artificial Sequence
<220> FEATURE:
<223> OTHER INFORMATION: VH DNA

<400> SEQUENCE: 50
caggtgcaat tggtgcagag cggtgcggaa gtgaaaaaac cgggtgccag cgtgaaagtt 60
agctgcaaag cgtccggata taccttcact tctaacttca tccattgggt gcgccaggcc 120
ccgggccagg gcctcgagtg gatgggctgg atctctccgt acaacggcga cacgaactac 180
gcgcagaaat ttcagggccg ggtgaccatg acccgtgata ccagcattag caccgcgtat 240
atggaactga gccgtctgcg tagcgaagat acggccgtgt attattgcgc gcgtgaatct 300
gtttactacg gttctgacta cggttacaac ggtatggata tctggggcca aggcaccctg 360
gtgactgtta gctca 375

<210> SEQ ID NO 51
<211> LENGTH: 10
<212> TYPE: PRT
<213> ORGANISM: Artificial Sequence
<220> FEATURE:
<223> OTHER INFORMATION: HCDR1

<400> SEQUENCE: 51

Gly Tyr Thr Phe Thr Ser Asn Phe Ile His
1 5 10

<210> SEQ ID NO 52
<211> LENGTH: 20
<212> TYPE: PRT
<213> ORGANISM: Artificial Sequence
<220> FEATURE:
<223> OTHER INFORMATION: HCDR2

<400> SEQUENCE: 52

Trp Met Gly Trp Ile Ser Pro Tyr Asn Gly Asp Thr Asn Tyr Ala Gln
1 5 10 15

Lys Phe Gln Gly
20

<210> SEQ ID NO 53
<211> LENGTH: 16
<212> TYPE: PRT
<213> ORGANISM: Artificial Sequence
<220> FEATURE:
<223> OTHER INFORMATION: HCDR3

<400> SEQUENCE: 53

```
Glu Ser Val Tyr Tyr Gly Ser Asp Tyr Gly Tyr Asn Gly Met Asp Ile
1               5                   10                  15


<210> SEQ ID NO 54
<211> LENGTH: 11
<212> TYPE: PRT
<213> ORGANISM: Artificial Sequence
<220> FEATURE:
<223> OTHER INFORMATION: LCDR1

<400> SEQUENCE: 54

Ser Gly Asp Asn Leu Gly Glu Glu Tyr Val Ser
1               5                   10


<210> SEQ ID NO 55
<211> LENGTH: 11
<212> TYPE: PRT
<213> ORGANISM: Artificial Sequence
<220> FEATURE:
<223> OTHER INFORMATION: LCDR2

<400> SEQUENCE: 55

Leu Val Ile Tyr Asp Asp Thr Lys Arg Pro Ser
1               5                   10


<210> SEQ ID NO 56
<211> LENGTH: 9
<212> TYPE: PRT
<213> ORGANISM: Artificial Sequence
<220> FEATURE:
<223> OTHER INFORMATION: LCDR3

<400> SEQUENCE: 56

Ser Ala Trp Ala Thr Trp Ser Val Ala
1               5


<210> SEQ ID NO 57
<211> LENGTH: 109
<212> TYPE: PRT
<213> ORGANISM: Artificial Sequence
<220> FEATURE:
<223> OTHER INFORMATION: VL

<400> SEQUENCE: 57

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Glu Glu Tyr Val
            20                  25                  30

Ser Trp Tyr Gln Gln Lys Pro Gly Gln Ala Pro Val Leu Val Ile Tyr
        35                  40                  45

Asp Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ala Trp Ala Thr Trp Ser Val Ala
                85                  90                  95

Val Phe Gly Gly Gly Thr Lys Leu Thr Val Leu Gly Gln
            100                 105


<210> SEQ ID NO 58
<211> LENGTH: 125
<212> TYPE: PRT
<213> ORGANISM: Artificial Sequence
```

<220> FEATURE:
<223> OTHER INFORMATION: VH

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Phe Ile His Trp Val Arg Gln Ala Pro Gly Gln Gly Leu Glu Trp Met
        35                  40                  45

Gly Trp Ile Ser Pro Tyr Asn Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Val Tyr Tyr Gly Ser Asp Tyr Gly Tyr Asn Gly Met
            100                 105                 110

Asp Ile Trp Gly Gln Gly Thr Leu Val Thr Val Ser Ser
        115                 120                 125

<210> SEQ ID NO 59
<211> LENGTH: 327
<212> TYPE: DNA
<213> ORGANISM: Artificial Sequence
<220> FEATURE:
<223> OTHER INFORMATION: VL DNA

<400> SEQUENCE: 59
gatatcgaac tgacccagcc gccgagcgtg agcgtgagcc cgggccagac cgcgagcatt 60
acctgtagcg gcgataacct gggtgaagaa tacgtttctt ggtaccagca gaaaccgggc 120
caggcgccgg tgctggtgat ctacgacgac actaaacgtc cgagcggcat cccggaacgt 180
tttagcggat ccaacagcgg caacaccgcg accctgacca ttagcggcac ccaggcggaa 240
gacgaagcgg attattactg ctctgcttgg gctacttggt ctgttgctgt gtttggcggc 300
ggcacgaagt taaccgttct tggccag 327

<210> SEQ ID NO 60
<211> LENGTH: 375
<212> TYPE: DNA
<213> ORGANISM: Artificial Sequence
<220> FEATURE:
<223> OTHER INFORMATION: VH DNA

<400> SEQUENCE: 60
caggtgcaat tggtgcagag cggtgcggaa gtgaaaaaac cgggtgccag cgtgaaagtt 60
agctgcaaag cgtccggata taccttcact tctaacttca tccattgggt gcgccaggcc 120
ccgggccagg gcctcgagtg gatgggctgg atctctccgt acaacggcga cacgaactac 180
gcgcagaaat ttcagggccg ggtgaccatg acccgtgata ccagcattag caccgcgtat 240
atggaactga gccgtctgcg tagcgaagat acggccgtgt attattgcgc gcgtgaatct 300
gtttactacg gttctgacta cggttacaac ggtatggata tctggggcca aggcaccctg 360
gtgactgtta gctca 375

<210> SEQ ID NO 61
<211> LENGTH: 10
<212> TYPE: PRT

<213> ORGANISM: Artificial Sequence
<220> FEATURE:
<223> OTHER INFORMATION: HCDR1

<400> SEQUENCE: 61

Gly Tyr Thr Phe Thr Ser Asn Phe Ile His
1 5 10

<210> SEQ ID NO 62
<211> LENGTH: 20
<212> TYPE: PRT
<213> ORGANISM: Artificial Sequence
<220> FEATURE:
<223> OTHER INFORMATION: HCDR2

<400> SEQUENCE: 62

Trp Met Gly Trp Ile Ser Pro Tyr Asn Gly Asp Thr Asn Tyr Ala Gln
1 5 10 15

Lys Phe Gln Gly
20

<210> SEQ ID NO 63
<211> LENGTH: 16
<212> TYPE: PRT
<213> ORGANISM: Artificial Sequence
<220> FEATURE:
<223> OTHER INFORMATION: HCDR3

<400> SEQUENCE: 63

Glu Ser Val Tyr Tyr Gly Ser Asp Tyr Gly Tyr Asn Gly Met Asp Ile
1 5 10 15

<210> SEQ ID NO 64
<211> LENGTH: 11
<212> TYPE: PRT
<213> ORGANISM: Artificial Sequence
<220> FEATURE:
<223> OTHER INFORMATION: LCDR1

<400> SEQUENCE: 64

Ser Gly Asp Asn Leu Gly Glu Glu Tyr Val Ser
1 5 10

<210> SEQ ID NO 65
<211> LENGTH: 11
<212> TYPE: PRT
<213> ORGANISM: Artificial Sequence
<220> FEATURE:
<223> OTHER INFORMATION: LCDR2

<400> SEQUENCE: 65

Leu Val Ile Tyr Asp Asp Thr Lys Arg Pro Ser
1 5 10

<210> SEQ ID NO 66
<211> LENGTH: 9
<212> TYPE: PRT
<213> ORGANISM: Artificial Sequence
<220> FEATURE:
<223> OTHER INFORMATION: LCDR3

<400> SEQUENCE: 66

Ser Ser Trp Thr His Phe Ser Asn Ile
1 5

<210> SEQ ID NO 67

<211> LENGTH: 109
<212> TYPE: PRT
<213> ORGANISM: Artificial Sequence
<220> FEATURE:
<223> OTHER INFORMATION: VL

<400> SEQUENCE: 67

Asp Ile Glu Leu Thr Gln Pro Pro Ser Val Ser Val Ser Pro Gly Gln
1 5 10 15

Thr Ala Ser Ile Thr Cys Ser Gly Asp Asn Leu Gly Glu Glu Tyr Val
20 25 30

Ser Trp Tyr Gln Gln Lys Pro Gly Gln Ala Pro Val Leu Val Ile Tyr
35 40 45

Asp Asp Thr Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Ser Ser Trp Thr His Phe Ser Asn Ile
85 90 95

Val Phe Gly Gly Gly Thr Lys Leu Thr Val Leu Gly Gln
100 105

<210> SEQ ID NO 68
<211> LENGTH: 125
<212> TYPE: PRT
<213> ORGANISM: Artificial Sequence
<220> FEATURE:
<223> OTHER INFORMATION: VH

<400> SEQUENCE: 68

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Asn
20 25 30

Phe Ile His Trp Val Arg Gln Ala Pro Gly Gln Gly Leu Glu Trp Met
35 40 45

Gly Trp Ile Ser Pro Tyr Asn Gly Asp Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Glu Asp Thr Ala Val Tyr Tyr Cys
85 90 95

Ala Arg Glu Ser Val Tyr Tyr Gly Ser Asp Tyr Gly Tyr Asn Gly Met
100 105 110

Asp Ile Trp Gly Gln Gly Thr Leu Val Thr Val Ser Ser
115 120 125

<210> SEQ ID NO 69
<211> LENGTH: 327
<212> TYPE: DNA
<213> ORGANISM: Artificial Sequence
<220> FEATURE:
<223> OTHER INFORMATION: VL DNA

<400> SEQUENCE: 69
gatatcgaac tgacccagcc gccgagcgtg agcgtgagcc cgggccagac cgcgagcatt 60
acctgtagcg gcgataacct gggtgaagaa tacgtttctt ggtaccagca gaaaccgggc 120
caggcgccgg tgctggtgat ctacgacgac actaaacgtc cgagcggcat cccggaacgt 180

```
tttagcggat ccaacagcgg caacaccgcg accctgacca ttagcggcac ccaggcggaa    240

gacgaagcgg attattactg ctcttcttgg actcatttct ctaacatcgt gtttggcggc    300

ggcacgaagt taaccgttct tggccag                                        327


<210> SEQ ID NO 70
<211> LENGTH: 375
<212> TYPE: DNA
<213> ORGANISM: Artificial Sequence
<220> FEATURE:
<223> OTHER INFORMATION: VH DNA

<400> SEQUENCE: 70

caggtgcaat tggtgcagag cggtgcggaa gtgaaaaaac cgggtgccag cgtgaaagtt     60

agctgcaaag cgtccggata taccttcact tctaacttca tccattgggt gcgccaggcc    120

ccgggccagg gcctcgagtg gatgggctgg atctctccgt acaacggcga cacgaactac    180

gcgcagaaat ttcagggccg ggtgaccatg acccgtgata ccagcattag caccgcgtat    240

atggaactga gccgtctgcg tagcgaagat acggccgtgt attattgcgc gcgtgaatct    300

gtttactacg gttctgacta cggttacaac ggtatggata tctggggcca aggcaccctg    360

gtgactgtta gctca                                                     375


<210> SEQ ID NO 71
<211> LENGTH: 12
<212> TYPE: PRT
<213> ORGANISM: Artificial Sequence
<220> FEATURE:
<223> OTHER INFORMATION: HCDR1

<400> SEQUENCE: 71

Gly Asp Ser Val Ser Ser Asn Ser Ala Ala Trp Asn
1               5                   10


<210> SEQ ID NO 72
<211> LENGTH: 21
<212> TYPE: PRT
<213> ORGANISM: Artificial Sequence
<220> FEATURE:
<223> OTHER INFORMATION: HCDR2

<400> SEQUENCE: 72

Trp Leu Gly Val Ile Tyr Tyr Arg Ser Lys Trp Tyr Ile Asn Tyr Ala
1               5                   10                  15

Asp Ser Val Lys Ser
            20


<210> SEQ ID NO 73
<211> LENGTH: 10
<212> TYPE: PRT
<213> ORGANISM: Artificial Sequence
<220> FEATURE:
<223> OTHER INFORMATION: HCDR3

<400> SEQUENCE: 73

Glu Gly Ile Val Gly Gly Trp Phe Ala Tyr
1               5                   10


<210> SEQ ID NO 74
<211> LENGTH: 11
<212> TYPE: PRT
<213> ORGANISM: Artificial Sequence
<220> FEATURE:
<223> OTHER INFORMATION: LCDR1
```

<400> SEQUENCE: 74

Ser Gly Asp Lys Leu Gly Ser Lys Ile Ala His
1 5 10

<210> SEQ ID NO 75
<211> LENGTH: 11
<212> TYPE: PRT
<213> ORGANISM: Artificial Sequence
<220> FEATURE:
<223> OTHER INFORMATION: LCDR2

<400> SEQUENCE: 75

Leu Val Ile Tyr Asp Asp Asn Glu Arg Pro Ser
1 5 10

<210> SEQ ID NO 76
<211> LENGTH: 10
<212> TYPE: PRT
<213> ORGANISM: Artificial Sequence
<220> FEATURE:
<223> OTHER INFORMATION: LCDR3

<400> SEQUENCE: 76

Gln Ser Trp Asp Tyr Leu Ser Trp Ser Val
1 5 10

<210> SEQ ID NO 77
<211> LENGTH: 110
<212> TYPE: PRT
<213> ORGANISM: Artificial Sequence
<220> FEATURE:
<223> OTHER INFORMATION: VL

<400> SEQUENCE: 77

Asp Ile Glu Leu Thr Gln Pro Pro Ser Val Ser Val Ser Pro Gly Gln
1 5 10 15

Thr Ala Ser Ile Thr Cys Ser Gly Asp Lys Leu Gly Ser Lys Ile Ala
20 25 30

His Trp Tyr Gln Gln Lys Pro Gly Gln Ala Pro Val Leu Val Ile Tyr
35 40 45

Asp Asp Asn Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Asp Tyr Leu Ser Trp Ser
85 90 95

Val Val Phe Gly Gly Gly Thr Lys Leu Thr Val Leu Gly Gln
100 105 110

<210> SEQ ID NO 78
<211> LENGTH: 330
<212> TYPE: PRT
<213> ORGANISM: Artificial Sequence
<220> FEATURE:
<223> OTHER INFORMATION: VH

<400> SEQUENCE: 78

Gly Ala Thr Ala Thr Cys Gly Ala Ala Cys Thr Gly Ala Cys Cys Cys
1 5 10 15

Ala Gly Cys Cys Gly Cys Cys Gly Ala Gly Cys Gly Thr Gly Ala Gly
20 25 30

```
Cys Gly Thr Gly Ala Gly Cys Cys Cys Gly Gly Gly Cys Cys Ala Gly
        35                  40                  45

Ala Cys Cys Gly Cys Gly Ala Gly Cys Ala Thr Thr Ala Cys Cys Thr
    50                  55                  60

Gly Thr Ala Gly Cys Gly Gly Cys Gly Ala Thr Ala Ala Ala Cys Thr
65                  70                  75                  80

Gly Gly Gly Thr Thr Cys Thr Ala Ala Ala Ala Thr Cys Gly Cys Thr
                85                  90                  95

Cys Ala Thr Thr Gly Gly Thr Ala Cys Cys Ala Gly Cys Ala Gly Ala
            100                 105                 110

Ala Ala Cys Cys Gly Gly Gly Cys Cys Ala Gly Gly Cys Gly Cys Cys
        115                 120                 125

Gly Gly Thr Gly Cys Thr Gly Gly Thr Gly Ala Thr Cys Thr Ala Cys
    130                 135                 140

Gly Ala Cys Gly Ala Cys Ala Ala Cys Gly Ala Ala Cys Gly Thr Cys
145                 150                 155                 160

Cys Gly Ala Gly Cys Gly Gly Cys Ala Thr Cys Cys Cys Gly Gly Ala
                165                 170                 175

Ala Cys Gly Thr Thr Thr Thr Ala Gly Cys Gly Gly Ala Thr Cys Cys
            180                 185                 190

Ala Ala Cys Ala Gly Cys Gly Gly Cys Ala Ala Cys Ala Cys Cys Gly
        195                 200                 205

Cys Gly Ala Cys Cys Cys Thr Gly Ala Cys Cys Ala Thr Thr Ala Gly
    210                 215                 220

Cys Gly Gly Cys Ala Cys Cys Cys Ala Gly Gly Cys Gly Gly Ala Ala
225                 230                 235                 240

Gly Ala Cys Gly Ala Ala Gly Cys Gly Gly Ala Thr Thr Ala Thr Thr
                245                 250                 255

Ala Cys Thr Gly Cys Cys Ala Gly Thr Cys Thr Thr Gly Gly Gly Ala
            260                 265                 270

Cys Thr Ala Cys Cys Thr Gly Thr Cys Thr Thr Gly Gly Thr Cys Thr
        275                 280                 285

Gly Thr Thr Gly Thr Gly Thr Thr Thr Gly Gly Cys Gly Gly Cys Gly
    290                 295                 300

Gly Cys Ala Cys Gly Ala Ala Gly Thr Thr Ala Ala Cys Cys Gly Thr
305                 310                 315                 320

Thr Cys Thr Thr Gly Gly Cys Cys Ala Gly
                325                 330
```

<210> SEQ ID NO 79
<211> LENGTH: 330
<212> TYPE: DNA
<213> ORGANISM: Artificial Sequence
<220> FEATURE:
<223> OTHER INFORMATION: VL DNA

<400> SEQUENCE: 79

```
gatatcgaac tgacccagcc gccgagcgtg agcgtgagcc cgggccagac cgcgagcatt     60

acctgtagcg gcgataaact gggttctaaa atcgctcatt ggtaccagca gaaaccgggc    120

caggcgccgg tgctggtgat ctacgacgac aacgaacgtc cgagcggcat cccggaacgt    180

tttagcggat ccaacagcgg caacaccgcg accctgacca ttagcggcac ccaggcggaa    240

gacgaagcgg attattactg ccagtcttgg gactacctgt cttggtctgt tgtgtttggc    300

ggcggcacga agttaaccgt tcttggccag                                     330
```

<210> SEQ ID NO 80
<211> LENGTH: 366
<212> TYPE: DNA
<213> ORGANISM: Artificial Sequence
<220> FEATURE:
<223> OTHER INFORMATION: VH DNA

<400> SEQUENCE: 80
caggtgcaat tgcagcagag cggtccgggc ctggtgaaac cgagccagac cctgagcctg 60
acctgcgcga tttccggaga tagcgtgagc agtaactctg ctgcttggaa ctggattcgt 120
cagagcccga gccgtggcct cgagtggctg ggcgttatct actaccgtag caaatggtac 180
atcaactatg ccgacagcgt gaaaagccgc attaccatta acccggatac ttcgaaaaac 240
cagtttagcc tgcaactgaa cagcgtgacc ccggaagata cggccgtgta ttattgcgcg 300
cgtgaaggta tcgttggtgg ttggttcgct tactggggcc aaggcaccct ggtgactgtt 360
agctca 366

<210> SEQ ID NO 81
<211> LENGTH: 12
<212> TYPE: PRT
<213> ORGANISM: Artificial Sequence
<220> FEATURE:
<223> OTHER INFORMATION: HCDR1

<400> SEQUENCE: 81

Gly Asp Ser Val Ser Ser Ser Ser Ala Ala Trp Asn
1               5                   10

<210> SEQ ID NO 82
<211> LENGTH: 21
<212> TYPE: PRT
<213> ORGANISM: Artificial Sequence
<220> FEATURE:
<223> OTHER INFORMATION: HCDR2

<400> SEQUENCE: 82

Trp Leu Gly Arg Ile Glu Tyr Arg Ser Lys Trp Tyr Asn Asp Tyr Ala
1               5                   10                  15

Val Ser Val Lys Ser
            20

<210> SEQ ID NO 83
<211> LENGTH: 13
<212> TYPE: PRT
<213> ORGANISM: Artificial Sequence
<220> FEATURE:
<223> OTHER INFORMATION: HCDR3

<400> SEQUENCE: 83

Glu Met Tyr Tyr Tyr Ser Gly Tyr Gly Val Phe Asp Val
1               5                   10

<210> SEQ ID NO 84
<211> LENGTH: 11
<212> TYPE: PRT
<213> ORGANISM: Artificial Sequence
<220> FEATURE:
<223> OTHER INFORMATION: LCDR1

<400> SEQUENCE: 84

Ser Gly Asp Ala Leu Gly Gly Glu Tyr Val His
1               5                   10

<210> SEQ ID NO 85
<211> LENGTH: 11
<212> TYPE: PRT
<213> ORGANISM: Artificial Sequence
<220> FEATURE:
<223> OTHER INFORMATION: LCDR2

<400> SEQUENCE: 85

```
Leu Val Ile Tyr Asp Asp Asp Lys Arg Pro Ser
1               5                   10
```

<210> SEQ ID NO 86
<211> LENGTH: 9
<212> TYPE: PRT
<213> ORGANISM: Artificial Sequence
<220> FEATURE:
<223> OTHER INFORMATION: LCDR3

<400> SEQUENCE: 86

```
Ser Ser Phe Asp Thr Trp Thr Ser Tyr
1               5
```

<210> SEQ ID NO 87
<211> LENGTH: 109
<212> TYPE: PRT
<213> ORGANISM: Artificial Sequence
<220> FEATURE:
<223> OTHER INFORMATION: VL

<400> SEQUENCE: 87

```
Asp Ile Glu Leu Thr Gln Pro Pro Ser Val Ser Val Ser Pro Gly Gln
1               5                   10                  15

Thr Ala Ser Ile Thr Cys Ser Gly Asp Ala Leu Gly Gly Glu Tyr Val
            20                  25                  30

His Trp Tyr Gln Gln Lys Pro Gly Gln Ala Pro Val Leu Val Ile Tyr
        35                  40                  45

Asp Asp Asp Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Phe Asp Thr Trp Thr Ser Tyr
                85                  90                  95

Val Phe Gly Gly Gly Thr Lys Leu Thr Val Leu Gly Gln
            100                 105
```

<210> SEQ ID NO 88
<211> LENGTH: 125
<212> TYPE: PRT
<213> ORGANISM: Artificial Sequence
<220> FEATURE:
<223> OTHER INFORMATION: VH

<400> SEQUENCE: 88

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Asn Trp Ile Arg Gln Ser Pro Ser Arg Gly Leu Glu
        35                  40                  45

Trp Leu Gly Arg Ile Glu Tyr Arg Ser Lys Trp Tyr Asn Asp Tyr Ala
    50                  55                  60
```

```
Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Met Tyr Tyr Tyr Ser Gly Tyr Gly Val Phe
            100                 105                 110

Asp Val Trp Gly Gln Gly Thr Leu Val Thr Val Ser Ser
        115                 120                 125


<210> SEQ ID NO 89
<211> LENGTH: 327
<212> TYPE: DNA
<213> ORGANISM: Artificial Sequence
<220> FEATURE:
<223> OTHER INFORMATION: VL DNA

<400> SEQUENCE: 89

gatatcgaac tgacccagcc gccgagcgtg agcgtgagcc cgggccagac cgcgagcatt      60

acctgtagcg gcgatgctct gggtggtgaa tacgttcatt ggtaccagca gaaaccgggc     120

caggcgccgg tgctggtgat ctacgacgac gacaaacgtc cgagcggcat cccggaacgt     180

tttagcggat ccaacagcgg caacaccgcg accctgacca ttagcggcac ccaggcggaa     240

gacgaagcgg attattactg ctcttctttc gacacttgga cttcttacgt gtttggcggc     300

ggcacgaagt taaccgttct tggccag                                         327


<210> SEQ ID NO 90
<211> LENGTH: 375
<212> TYPE: DNA
<213> ORGANISM: Artificial Sequence
<220> FEATURE:
<223> OTHER INFORMATION: VH DNA

<400> SEQUENCE: 90

caggtgcaat tgcagcagag cggtccgggc ctggtgaaac cgagccagac cctgagcctg      60

acctgcgcga tttccggaga tagcgtgagc tcctcttctg ctgcttggaa ctggattcgt     120

cagagcccga gccgtggcct cgagtggctg ggccgtatcg aataccgtag caaatggtac     180

aacgactatg ccgtgagcgt gaaaagccgc attaccatta acccggatac ttcgaaaaac     240

cagtttagcc tgcaactgaa cagcgtgacc ccggaagata cggccgtgta ttattgcgcg     300

cgtgaaatgt actactactc tggttacggt gttttcgatg tttggggcca aggcaccctg     360

gtgactgtta gctca                                                      375


<210> SEQ ID NO 91
<211> LENGTH: 10
<212> TYPE: PRT
<213> ORGANISM: Artificial Sequence
<220> FEATURE:
<223> OTHER INFORMATION: HCDR1

<400> SEQUENCE: 91

Gly Phe Thr Phe Ser Asp Tyr Ala Met Thr
1               5                   10


<210> SEQ ID NO 92
<211> LENGTH: 20
<212> TYPE: PRT
<213> ORGANISM: Artificial Sequence
<220> FEATURE:
<223> OTHER INFORMATION: HCDR2
```

<400> SEQUENCE: 92

Trp Val Ser Val Ile Ser Tyr Asp Gly Ser Leu Thr Tyr Tyr Ala Asp
1 5 10 15

Ser Val Lys Gly
20

<210> SEQ ID NO 93
<211> LENGTH: 12
<212> TYPE: PRT
<213> ORGANISM: Artificial Sequence
<220> FEATURE:
<223> OTHER INFORMATION: HCDR3

<400> SEQUENCE: 93

Asp Pro Gly Val Trp Trp Leu Ser Tyr Leu Asp Tyr
1 5 10

<210> SEQ ID NO 94
<211> LENGTH: 11
<212> TYPE: PRT
<213> ORGANISM: Artificial Sequence
<220> FEATURE:
<223> OTHER INFORMATION: LCDR1

<400> SEQUENCE: 94

Arg Ala Ser Gln Asp Ile Ile Ser Tyr Leu Ala
1 5 10

<210> SEQ ID NO 95
<211> LENGTH: 11
<212> TYPE: PRT
<213> ORGANISM: Artificial Sequence
<220> FEATURE:
<223> OTHER INFORMATION: LCDR2

<400> SEQUENCE: 95

Leu Leu Ile Tyr Gly Ala Ser Asn Leu Gln Gly
1 5 10

<210> SEQ ID NO 96
<211> LENGTH: 9
<212> TYPE: PRT
<213> ORGANISM: Artificial Sequence
<220> FEATURE:
<223> OTHER INFORMATION: LCDR3

<400> SEQUENCE: 96

Gln Gln Tyr Met Ile Ala Pro Pro Asn
1 5

<210> SEQ ID NO 97
<211> LENGTH: 110
<212> TYPE: PRT
<213> ORGANISM: Artificial Sequence
<220> FEATURE:
<223> OTHER INFORMATION: VL

<400> SEQUENCE: 97

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ile Ser Tyr
20 25 30

Leu Ala Trp Tyr Gln Gln Lys Pro Gly Lys Ala Pro Lys Leu Leu Ile
35 40 45

```
Tyr Gly Ala Ser Asn Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Met Ile Ala Pro Pro
                85                  90                  95

Asn Thr Phe Gly Gln Gly Thr Lys Val Glu Ile Lys Arg Thr
            100                 105                 110


<210> SEQ ID NO 98
<211> LENGTH: 121
<212> TYPE: PRT
<213> ORGANISM: Artificial Sequence
<220> FEATURE:
<223> OTHER INFORMATION: VH

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Thr Trp Val Arg Gln Ala Pro Gly Lys Gly Leu Glu Trp Val
        35                  40                  45

Ser Val Ile Ser Tyr Asp Gly Ser Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Val Trp Trp Leu Ser Tyr Leu Asp Tyr Trp Gly
            100                 105                 110

Gln Gly Thr Leu Val Thr Val Ser Ser
        115                 120


<210> SEQ ID NO 99
<211> LENGTH: 330
<212> TYPE: DNA
<213> ORGANISM: Artificial Sequence
<220> FEATURE:
<223> OTHER INFORMATION: VL DNA

<400> SEQUENCE: 99

gatatccaga tgacccagag cccgagcagc ctgagcgcca gcgtgggcga tcgcgtgacc     60

attacctgca gagccagcca ggacattatc tcttacctgg cttggtacca gcagaaaccg    120

ggcaaagcgc cgaaactatt aatctacggt gcttctaacc tgcaaggcgg cgtgccgagc    180

cgctttagcg gcagcggatc cggcaccgat ttcaccctga ccattagctc tctgcaaccg    240

gaagactttg cggtgtatta ttgccagcag tacatgatcg ctccaccgaa cacctttggc    300

cagggcacga aagttgaaat taaacgtacg                                     330


<210> SEQ ID NO 100
<211> LENGTH: 363
<212> TYPE: DNA
<213> ORGANISM: Artificial Sequence
<220> FEATURE:
<223> OTHER INFORMATION: VH DNA

<400> SEQUENCE: 100

gaagtgcaat tgctggaaag cggcggtggc ctggtgcagc cgggtggcag cctgcgtctg     60
```

-continued

```
agctgcgcgg cgtccggatt caccttttct gactacgcta tgacttgggt gcgccaggcc    120

ccgggcaaag gtctcgagtg ggtttccgtt atctcttacg acggttctct gacctactat    180

gcggatagcg tgaaaggccg ctttaccatc agccgcgata attcgaaaaa caccctgtat    240

ctgcaaatga acagcctgcg tgcggaagat acggccgtgt attattgcgc gcgtgacccg    300

ggtgtttggt ggctgtctta cctggattac tggggccaag gcaccctggt gactgttagc    360

tca                                                                  363


<210> SEQ ID NO 101
<211> LENGTH: 12
<212> TYPE: PRT
<213> ORGANISM: Artificial Sequence
<220> FEATURE:
<223> OTHER INFORMATION: HCDR1

<400> SEQUENCE: 101

Gly Asp Ser Val Ser Ser Asn Ser Ala Ala Trp Asn
1               5                   10


<210> SEQ ID NO 102
<211> LENGTH: 21
<212> TYPE: PRT
<213> ORGANISM: Artificial Sequence
<220> FEATURE:
<223> OTHER INFORMATION: HCDR2

<400> SEQUENCE: 102

Trp Leu Gly Lys Thr Tyr Tyr Arg Ser Thr Trp Ser Asn Asp Tyr Ala
1               5                   10                  15

Glu Ser Val Lys Ser
            20


<210> SEQ ID NO 103
<211> LENGTH: 16
<212> TYPE: PRT
<213> ORGANISM: Artificial Sequence
<220> FEATURE:
<223> OTHER INFORMATION: HCDR3

<400> SEQUENCE: 103

Glu Met Asp Ser Leu Thr Arg Ser Ala Ser Ser Ile Ala Phe Asp Tyr
1               5                   10                  15


<210> SEQ ID NO 104
<211> LENGTH: 11
<212> TYPE: PRT
<213> ORGANISM: Artificial Sequence
<220> FEATURE:
<223> OTHER INFORMATION: LCDR1

<400> SEQUENCE: 104

Ser Gly Asp Asn Leu Arg Glu His Tyr Val His
1               5                   10


<210> SEQ ID NO 105
<211> LENGTH: 11
<212> TYPE: PRT
<213> ORGANISM: Artificial Sequence
<220> FEATURE:
<223> OTHER INFORMATION: LCDR2

<400> SEQUENCE: 105

Leu Val Ile Tyr Asp Asp Thr Glu Arg Pro Ser
```

1 5 10

<210> SEQ ID NO 106
<211> LENGTH: 8
<212> TYPE: PRT
<213> ORGANISM: Artificial Sequence
<220> FEATURE:
<223> OTHER INFORMATION: LCDR3

<400> SEQUENCE: 106

Ala Thr Arg Asp Trp Ser Asn Val
1 5

<210> SEQ ID NO 107
<211> LENGTH: 108
<212> TYPE: PRT
<213> ORGANISM: Artificial Sequence
<220> FEATURE:
<223> OTHER INFORMATION: VL

<400> SEQUENCE: 107

Asp Ile Glu Leu Thr Gln Pro Pro Ser Val Ser Val Ser Pro Gly Gln
1 5 10 15

Thr Ala Ser Ile Thr Cys Ser Gly Asp Asn Leu Arg Glu His Tyr Val
20 25 30

His Trp Tyr Gln Gln Lys Pro Gly Gln Ala Pro Val Leu Val Ile Tyr
35 40 45

Asp Asp Thr Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Ala Thr Arg Asp Trp Ser Asn Val Val
85 90 95

Phe Gly Gly Gly Thr Lys Leu Thr Val Leu Gly Gln
100 105

<210> SEQ ID NO 108
<211> LENGTH: 128
<212> TYPE: PRT
<213> ORGANISM: Artificial Sequence
<220> FEATURE:
<223> OTHER INFORMATION: VH

<400> SEQUENCE: 108

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Lys Thr Tyr Tyr Arg Ser Thr Trp Ser Asn Asp Tyr Ala
50 55 60

Glu Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Met Asp Ser Leu Thr Arg Ser Ala Ser Ser
100 105 110

Ile Ala Phe Asp Tyr Trp Gly Gln Gly Thr Leu Val Thr Val Ser Ser
115 120 125

<210> SEQ ID NO 109
<211> LENGTH: 324
<212> TYPE: DNA
<213> ORGANISM: Artificial Sequence
<220> FEATURE:
<223> OTHER INFORMATION: VL DNA

<400> SEQUENCE: 109
gatatcgaac tgacccagcc gccgagcgtg agcgtgagcc cgggccagac cgcgagcatt 60
acctgtagcg gcgataacct gcgtgaacat tacgttcatt ggtaccagca gaaaccgggc 120
caggcgccgg tgctggtgat ctacgacgac actgaacgtc cgagcggcat cccggaacgt 180
tttagcggat ccaacagcgg caacaccgcg accctgacca ttagcggcac ccaggcggaa 240
gacgaagcgg attattactg cgctactcgt gactggtcta acgttgtgtt tggcggcggc 300
acgaagttaa ccgttcttgg ccag 324

<210> SEQ ID NO 110
<211> LENGTH: 384
<212> TYPE: DNA
<213> ORGANISM: Artificial Sequence
<220> FEATURE:
<223> OTHER INFORMATION: VH DNA

<400> SEQUENCE: 110
caggtgcaat tgcagcagag cggtccgggc ctggtgaaac cgagccagac cctgagcctg 60
acctgcgcga tttccggaga tagcgtgagc agtaactctg ctgcttggaa ctggattcgt 120
cagagcccga gccgtggcct cgagtggctg ggcaaaacct actaccgtag cacttggtct 180
aacgactatg ccgaaagcgt gaaaagccgc attaccatta acccggatac ttcgaaaaac 240
cagtttagcc tgcaactgaa cagcgtgacc ccggaagata cggccgtgta ttattgcgcg 300
cgtgaaatgg actctctgac tcgttctgct tcttctatcg ctttcgatta ctggggccaa 360
ggcaccctgg tgactgttag ctca 384

<210> SEQ ID NO 111
<211> LENGTH: 12
<212> TYPE: PRT
<213> ORGANISM: Artificial Sequence
<220> FEATURE:
<223> OTHER INFORMATION: HCDR1

<400> SEQUENCE: 111

Gly Asp Ser Val Ser Asp Asn Ser Val Ala Trp Asn
1 5 10

<210> SEQ ID NO 112
<211> LENGTH: 21
<212> TYPE: PRT
<213> ORGANISM: Artificial Sequence
<220> FEATURE:
<223> OTHER INFORMATION: HCDR2

<400> SEQUENCE: 112

Trp Leu Gly Arg Ile Tyr Tyr Arg Ser Lys Trp Tyr Asn Asp Tyr Ala
1 5 10 15

Val Ser Val Lys Ser
20

<210> SEQ ID NO 113
<211> LENGTH: 16

<212> TYPE: PRT
<213> ORGANISM: Artificial Sequence
<220> FEATURE:
<223> OTHER INFORMATION: HCDR3

<400> SEQUENCE: 113

Glu Val Leu Leu Phe Pro Ala Arg Ser Tyr Gly Thr Gly Met Asp Val
1 5 10 15

<210> SEQ ID NO 114
<211> LENGTH: 11
<212> TYPE: PRT
<213> ORGANISM: Artificial Sequence
<220> FEATURE:
<223> OTHER INFORMATION: LCDR1

<400> SEQUENCE: 114

Ser Gly Asp Asn Leu Pro Ser Lys Tyr Val His
1 5 10

<210> SEQ ID NO 115
<211> LENGTH: 11
<212> TYPE: PRT
<213> ORGANISM: Artificial Sequence
<220> FEATURE:
<223> OTHER INFORMATION: LCDR2

<400> SEQUENCE: 115

Leu Val Ile Tyr Asp Asp Asn Glu Arg Pro Ser
1 5 10

<210> SEQ ID NO 116
<211> LENGTH: 10
<212> TYPE: PRT
<213> ORGANISM: Artificial Sequence
<220> FEATURE:
<223> OTHER INFORMATION: LCDR3

<400> SEQUENCE: 116

Gly Val Ala Asp Met Pro Arg Gln Met Lys
1 5 10

<210> SEQ ID NO 117
<211> LENGTH: 110
<212> TYPE: PRT
<213> ORGANISM: Artificial Sequence
<220> FEATURE:
<223> OTHER INFORMATION: VL

<400> SEQUENCE: 117

Asp Ile Glu Leu Thr Gln Pro Pro Ser Val Ser Val Ser Pro Gly Gln
1 5 10 15

Thr Ala Ser Ile Thr Cys Ser Gly Asp Asn Leu Pro Ser Lys Tyr Val
20 25 30

His Trp Tyr Gln Gln Lys Pro Gly Gln Ala Pro Val Leu Val Ile Tyr
35 40 45

Asp Asp Asn Glu Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gly Val Ala Asp Met Pro Arg Gln Met
85 90 95

Lys Val Phe Gly Gly Gly Thr Lys Leu Thr Val Leu Gly Gln
100 105 110

<210> SEQ ID NO 118
<211> LENGTH: 128
<212> TYPE: PRT
<213> ORGANISM: Artificial Sequence
<220> FEATURE:
<223> OTHER INFORMATION: VH

<400> SEQUENCE: 118

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Asp Asn
20 25 30

Ser Val Ala Trp Asn Trp Ile Arg Gln Ser Pro Ser Arg Gly Leu Glu
35 40 45

Trp Leu Gly Arg Ile Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Val Leu Leu Phe Pro Ala Arg Ser Tyr Gly
100 105 110

Thr Gly Met Asp Val Trp Gly Gln Gly Thr Leu Val Thr Val Ser Ser
115 120 125

<210> SEQ ID NO 119
<211> LENGTH: 330
<212> TYPE: DNA
<213> ORGANISM: Artificial Sequence
<220> FEATURE:
<223> OTHER INFORMATION: VL DNA

<400> SEQUENCE: 119
gatatcgaac tgacccagcc gccgagcgtg agcgtgagcc cgggccagac cgcgagcatt 60
acctgtagcg gcgataacct gccgtctaaa tacgttcatt ggtaccagca gaaaccgggc 120
caggcgccgg tgctggtgat ctacgacgac aacgaacgtc cgagcggcat cccggaacgt 180
tttagcggat ccaacagcgg caacaccgcg accctgacca ttagcggcac ccaggcggaa 240
gacgaagcgg attattactg cggtgttgct gacatgccgc gtcagatgaa agtgtttggc 300
ggcggcacga agttaaccgt tcttggccag 330

<210> SEQ ID NO 120
<211> LENGTH: 384
<212> TYPE: DNA
<213> ORGANISM: Artificial Sequence
<220> FEATURE:
<223> OTHER INFORMATION: VH DNA

<400> SEQUENCE: 120
caggtgcaat tgcagcagag cggtccgggc ctggtgaaac cgagccagac cctgagcctg 60
acctgcgcga tttccggaga tagcgtgagc gacaactctg ttgcttggaa ctggattcgt 120
cagagcccga gccgtggcct cgagtggctg ggccgtatct actaccgtag caaatggtac 180
aacgactatg ccgtgagcgt gaaaagccgc attaccatta acccggatac ttcgaaaaac 240
cagtttagcc tgcaactgaa cagcgtgacc ccggaagata cggccgtgta ttattgcgcg 300
cgtgaagttc tgctgttccc ggctcgttct tacggtactg gtatggatgt ttggggccaa 360
ggcaccctgg tgactgttag ctca 384

<210> SEQ ID NO 121
<211> LENGTH: 10
<212> TYPE: PRT
<213> ORGANISM: Artificial Sequence
<220> FEATURE:
<223> OTHER INFORMATION: HCDR1

<400> SEQUENCE: 121

Gly Phe Thr Phe Ser Ser Tyr Ala Met Ser
1 5 10

<210> SEQ ID NO 122
<211> LENGTH: 20
<212> TYPE: PRT
<213> ORGANISM: Artificial Sequence
<220> FEATURE:
<223> OTHER INFORMATION: HCDR2

<400> SEQUENCE: 122

Trp Val Ser Phe Ile Ser Ser Gly Gly Ser Glu Thr Phe Tyr Ala Asp
1 5 10 15

Ser Val Lys Gly
20

<210> SEQ ID NO 123
<211> LENGTH: 14
<212> TYPE: PRT
<213> ORGANISM: Artificial Sequence
<220> FEATURE:
<223> OTHER INFORMATION: HCDR3

<400> SEQUENCE: 123

Val Ser Tyr Ile Tyr Tyr Tyr Ser Trp Val Leu Phe Asp Val
1 5 10

<210> SEQ ID NO 124
<211> LENGTH: 11
<212> TYPE: PRT
<213> ORGANISM: Artificial Sequence
<220> FEATURE:
<223> OTHER INFORMATION: LCDR1

<400> SEQUENCE: 124

Arg Ala Ser Gln Gly Ile Gly Thr Ala Leu Asn
1 5 10

<210> SEQ ID NO 125
<211> LENGTH: 11
<212> TYPE: PRT
<213> ORGANISM: Artificial Sequence
<220> FEATURE:
<223> OTHER INFORMATION: LCDR2

<400> SEQUENCE: 125

Leu Leu Ile Tyr Asp Val Ser Ser Leu Gln Ser
1 5 10

<210> SEQ ID NO 126
<211> LENGTH: 8
<212> TYPE: PRT
<213> ORGANISM: Artificial Sequence
<220> FEATURE:
<223> OTHER INFORMATION: LCDR3

<400> SEQUENCE: 126

```
Gln Gln Gly Leu Phe Leu Pro Phe
1               5


<210> SEQ ID NO 127
<211> LENGTH: 109
<212> TYPE: PRT
<213> ORGANISM: Artificial Sequence
<220> FEATURE:
<223> OTHER INFORMATION: VL

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Thr Ala
            20                  25                  30

Leu Asn Trp Tyr Gln Gln Lys Pro Gly Lys Ala Pro Lys Leu Leu Ile
        35                  40                  45

Tyr Asp Val Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Leu Phe Leu Pro Phe
                85                  90                  95

Thr Phe Gly Gln Gly Thr Lys Val Glu Ile Lys Arg Thr
            100                 105


<210> SEQ ID NO 128
<211> LENGTH: 123
<212> TYPE: PRT
<213> ORGANISM: Artificial Sequence
<220> FEATURE:
<223> OTHER INFORMATION: VH

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Phe Ile Ser Ser Gly Gly Ser Glu Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Tyr Ile Tyr Tyr Tyr Ser Trp Val Leu Phe Asp Val
            100                 105                 110

Trp Gly Gln Gly Thr Leu Val Thr Val Ser Ser
        115                 120


<210> SEQ ID NO 129
<211> LENGTH: 327
<212> TYPE: DNA
<213> ORGANISM: Artificial Sequence
<220> FEATURE:
<223> OTHER INFORMATION: VL DNA

<400> SEQUENCE: 129
```

```
gatatccaga tgacccagag cccgagcagc ctgagcgcca gcgtgggcga tcgcgtgacc      60

attacctgca gagccagcca gggtattggt actgctctga actggtacca gcagaaaccg     120

ggcaaagcgc cgaaactatt aatctacgac gtttcttctc tgcaaagcgg cgtgccgagc     180

cgctttagcg gcagcggatc cggcaccgat ttcaccctga ccattagctc tctgcaaccg     240

gaagactttg cgacctatta ttgccagcag ggtctgttcc tgccgttcac ctttggccag     300

ggcacgaaag ttgaaattaa acgtacg                                         327


<210> SEQ ID NO 130
<211> LENGTH: 369
<212> TYPE: DNA
<213> ORGANISM: Artificial Sequence
<220> FEATURE:
<223> OTHER INFORMATION: VH DNA

<400> SEQUENCE: 130

gaagtgcaat tgctggaaag cggcggtggc ctggtgcagc cgggtggcag cctgcgtctg      60

agctgcgcgg cgtccggatt caccttttct tcttacgcta tgtcttgggt gcgccaggcc     120

ccgggcaaag gtctcgagtg ggtttccttc atctcttctg gtggttctga aaccttctat     180

gcggatagcg tgaaaggccg ctttaccatc agccgcgata attcgaaaaa caccctgtat     240

ctgcaaatga acagcctgcg tgcggaagat acggccgtgt attattgcgc gcgtgtttct     300

tacatctact actactcttg ggttctgttc gatgtttggg gccaaggcac cctggtgact     360

gttagctca                                                             369


<210> SEQ ID NO 131
<211> LENGTH: 10
<212> TYPE: PRT
<213> ORGANISM: Artificial Sequence
<220> FEATURE:
<223> OTHER INFORMATION: HCDR1

<400> SEQUENCE: 131

Gly Tyr Ser Phe Thr Asp Tyr Trp Ile Ser
1               5                   10


<210> SEQ ID NO 132
<211> LENGTH: 20
<212> TYPE: PRT
<213> ORGANISM: Artificial Sequence
<220> FEATURE:
<223> OTHER INFORMATION: HCDR2

<400> SEQUENCE: 132

Trp Met Gly Ala Ile Asp Pro Thr Asp Ser Tyr Thr Arg Tyr Ser Pro
1               5                   10                  15

Ser Phe Gln Gly
            20


<210> SEQ ID NO 133
<211> LENGTH: 16
<212> TYPE: PRT
<213> ORGANISM: Artificial Sequence
<220> FEATURE:
<223> OTHER INFORMATION: HCDR3

<400> SEQUENCE: 133

Trp Tyr Thr Ser His Pro Tyr Tyr Glu Gly Arg Tyr Pro Met Asp Val
1               5                   10                  15
```

<210> SEQ ID NO 134
<211> LENGTH: 14
<212> TYPE: PRT
<213> ORGANISM: Artificial Sequence
<220> FEATURE:
<223> OTHER INFORMATION: LCDR1

<400> SEQUENCE: 134

Thr Gly Thr Ser Ser Asp Val Gly His Tyr Asn Tyr Val Ser
1 5 10

<210> SEQ ID NO 135
<211> LENGTH: 11
<212> TYPE: PRT
<213> ORGANISM: Artificial Sequence
<220> FEATURE:
<223> OTHER INFORMATION: LCDR2

<400> SEQUENCE: 135

Leu Met Ile Tyr Gly Val Thr Lys Arg Pro Ser
1 5 10

<210> SEQ ID NO 136
<211> LENGTH: 10
<212> TYPE: PRT
<213> ORGANISM: Artificial Sequence
<220> FEATURE:
<223> OTHER INFORMATION: LCDR3

<400> SEQUENCE: 136

Ala Ser Ala Asp Glu Trp Pro Thr Leu His
1 5 10

<210> SEQ ID NO 137
<211> LENGTH: 113
<212> TYPE: PRT
<213> ORGANISM: Artificial Sequence
<220> FEATURE:
<223> OTHER INFORMATION: VL

<400> SEQUENCE: 137

Asp Ile Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly His Tyr
20 25 30

Asn Tyr Val Ser Trp Tyr Gln Gln His Pro Gly Lys Ala Pro Lys Leu
35 40 45

Met Ile Tyr Gly Val Thr Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ala Ser Ala Asp Glu Trp
85 90 95

Pro Thr Leu His Val Phe Gly Gly Gly Thr Lys Leu Thr Val Leu Gly
100 105 110

Gln

<210> SEQ ID NO 138
<211> LENGTH: 125
<212> TYPE: PRT
<213> ORGANISM: Artificial Sequence
<220> FEATURE:
<223> OTHER INFORMATION: VH

<400> SEQUENCE: 138

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Trp Ile Ser Trp Val Arg Gln Met Pro Gly Lys Gly Leu Glu Trp Met
        35                  40                  45

Gly Ala Ile Asp Pro Thr Asp Ser Tyr Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Tyr Thr Ser His Pro Tyr Tyr Glu Gly Arg Tyr Pro Met
            100                 105                 110

Asp Val Trp Gly Gln Gly Thr Leu Val Thr Val Ser Ser
        115                 120                 125

<210> SEQ ID NO 139
<211> LENGTH: 339
<212> TYPE: DNA
<213> ORGANISM: Artificial Sequence
<220> FEATURE:
<223> OTHER INFORMATION: VL DNA

<400> SEQUENCE: 139
gatatcgcgc tgacccagcc ggcgagcgtg agcggtagcc cgggccagag cattaccatt 60
agctgcaccg gcaccagcag cgatgtgggc cattacaact acgtgtcttg gtaccagcag 120
catccgggca aggcgccgaa actgatgatc tacggtgtta ctaaacgtcc gagcggcgtg 180
agcaaccgtt ttagcggatc caaaagcggc aacaccgcga gcctgaccat tagcggcctg 240
caagcggaag acgaagcgga ttattactgc gcttctgctg acgaatggcc gactctgcat 300
gtgtttggcg gcggcacgaa gttaaccgtt cttggccag 339

<210> SEQ ID NO 140
<211> LENGTH: 375
<212> TYPE: DNA
<213> ORGANISM: Artificial Sequence
<220> FEATURE:
<223> OTHER INFORMATION: VH DNA

<400> SEQUENCE: 140
gaagtgcaat tggtgcagag cggtgcggaa gtgaaaaaac cgggcgaaag cctgaaaatt 60
agctgcaaag gctccggata tagcttcact gactactgga tctcttgggt gcgccagatg 120
ccgggcaaag gtctcgagtg gatgggcgct atcgacccga ctgacagcta cacccgttat 180
agcccgagct ttcagggcca ggtgaccatt agcgcggata aaagcatcag caccgcgtat 240
ctgcaatgga gcagcctgaa agcgagcgat accgcgatgt attattgcgc gcgttggtac 300
acttctcatc cgtactacga aggtcgttac ccgatggatg tttggggcca aggcaccctg 360
gtgactgtta gctca 375

<210> SEQ ID NO 141
<211> LENGTH: 10
<212> TYPE: PRT
<213> ORGANISM: Artificial Sequence
<220> FEATURE:
<223> OTHER INFORMATION: HCDR1

<400> SEQUENCE: 141

Gly Tyr Ser Phe Asn Asn Tyr Trp Ile Ala
1               5                   10

<210> SEQ ID NO 142
<211> LENGTH: 20
<212> TYPE: PRT
<213> ORGANISM: Artificial Sequence
<220> FEATURE:
<223> OTHER INFORMATION: HCDR2

<400> SEQUENCE: 142

Trp Met Gly Phe Ile Tyr Pro Ser Asn Ser Ala Thr Gln Tyr Ser Pro
1               5                   10                  15

Ser Phe Gln Gly
            20

<210> SEQ ID NO 143
<211> LENGTH: 11
<212> TYPE: PRT
<213> ORGANISM: Artificial Sequence
<220> FEATURE:
<223> OTHER INFORMATION: HCDR3

<400> SEQUENCE: 143

Asp Asn Glu Tyr Ser Asp Ser Tyr Phe Asp Val
1               5                   10

<210> SEQ ID NO 144
<211> LENGTH: 11
<212> TYPE: PRT
<213> ORGANISM: Artificial Sequence
<220> FEATURE:
<223> OTHER INFORMATION: LCDR1

<400> SEQUENCE: 144

Arg Ala Ser Gln Ile Val Ser Ser Tyr Leu Ala
1               5                   10

<210> SEQ ID NO 145
<211> LENGTH: 11
<212> TYPE: PRT
<213> ORGANISM: Artificial Sequence
<220> FEATURE:
<223> OTHER INFORMATION: LCDR2

<400> SEQUENCE: 145

Leu Leu Ile Tyr Asp Ala Ser Ser Arg Ala Thr
1               5                   10

<210> SEQ ID NO 146
<211> LENGTH: 8
<212> TYPE: PRT
<213> ORGANISM: Artificial Sequence
<220> FEATURE:
<223> OTHER INFORMATION: LCDR3

<400> SEQUENCE: 146

Gln Gln Ser Val Asn Phe Pro Thr
1               5

<210> SEQ ID NO 147
<211> LENGTH: 109
<212> TYPE: PRT
<213> ORGANISM: Artificial Sequence

<220> FEATURE:
<223> OTHER INFORMATION: VL

<400> SEQUENCE: 147

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ile Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Val Asn Phe Pro Thr
                85                  90                  95

Thr Phe Gly Gln Gly Thr Lys Val Glu Ile Lys Arg Thr
            100                 105

<210> SEQ ID NO 148
<211> LENGTH: 120
<212> TYPE: PRT
<213> ORGANISM: Artificial Sequence
<220> FEATURE:
<223> OTHER INFORMATION: VH

<400> SEQUENCE: 148

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Ala Trp Val Arg Gln Met Pro Gly Lys Gly Leu Glu Trp Met
        35                  40                  45

Gly Phe Ile Tyr Pro Ser Asn Ser Ala Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Asn Glu Tyr Ser Asp Ser Tyr Phe Asp Val Trp Gly Gln
            100                 105                 110

Gly Thr Leu Val Thr Val Ser Ser
        115                 120

<210> SEQ ID NO 149
<211> LENGTH: 327
<212> TYPE: DNA
<213> ORGANISM: Artificial Sequence
<220> FEATURE:
<223> OTHER INFORMATION: VL DNA

<400> SEQUENCE: 149
gatatcgtgc tgacccagag cccggcgacc ctgagcctga gcccgggtga acgtgccacc 60
ctgagctgca gagcgagcca gatcgtttct tcttacctgg cttggtacca gcagaaaccg 120
ggccaggccc cgcgtctatt aatctacgac gcttcttctc gtgcgaccgg cattccggcg 180
cgttttagcg gcagcggatc cggcaccgat ttcaccctga ccattagcag cctggaaccg 240
gaagactttg cggtgtatta ttgccagcag tctgttaact tcccgactac ctttggccag 300
ggcacgaaag ttgaaattaa acgtacg 327

<210> SEQ ID NO 150
<211> LENGTH: 360
<212> TYPE: DNA
<213> ORGANISM: Artificial Sequence
<220> FEATURE:
<223> OTHER INFORMATION: VH DNA

<400> SEQUENCE: 150
gaagtgcaat tggtgcagag cggtgcggaa gtgaaaaaac cgggcgaaag cctgaaaatt 60
agctgcaaag gctccggata tagcttcaac aactactgga tcgcttgggt gcgccagatg 120
ccgggcaaag gtctcgagtg gatgggcttc atctacccgt ctaacagcgc tacccagtat 180
agcccgagct ttcagggcca ggtgaccatt agcgcggata aaagcatcag caccgcgtat 240
ctgcaatgga gcagcctgaa agcgagcgat accgcgatgt attattgcgc gcgtgacaac 300
gaatactctg actcttactt cgatgtttgg ggccaaggca ccctggtgac tgttagctca 360

<210> SEQ ID NO 151
<211> LENGTH: 10
<212> TYPE: PRT
<213> ORGANISM: Artificial Sequence
<220> FEATURE:
<223> OTHER INFORMATION: HCDR1

<400> SEQUENCE: 151

Gly Tyr Ser Phe Asn Asn Tyr Trp Ile Ala
1 5 10

<210> SEQ ID NO 152
<211> LENGTH: 20
<212> TYPE: PRT
<213> ORGANISM: Artificial Sequence
<220> FEATURE:
<223> OTHER INFORMATION: HCDR2

<400> SEQUENCE: 152

Trp Met Gly Phe Ile Tyr Pro Ser Asn Ser Ala Thr Gln Tyr Ser Pro
1 5 10 15

Ser Phe Gln Gly
20

<210> SEQ ID NO 153
<211> LENGTH: 11
<212> TYPE: PRT
<213> ORGANISM: Artificial Sequence
<220> FEATURE:
<223> OTHER INFORMATION: HCDR3

<400> SEQUENCE: 153

Asp Asn Glu Tyr Ser Asp Ser Tyr Phe Asp Val
1 5 10

<210> SEQ ID NO 154
<211> LENGTH: 11
<212> TYPE: PRT
<213> ORGANISM: Artificial Sequence
<220> FEATURE:
<223> OTHER INFORMATION: LCDR1

<400> SEQUENCE: 154

Arg Ala Ser Gln Ile Val Ser Ser Tyr Leu Ala
1 5 10

<210> SEQ ID NO 155
<211> LENGTH: 11
<212> TYPE: PRT
<213> ORGANISM: Artificial Sequence
<220> FEATURE:
<223> OTHER INFORMATION: LCDR2

<400> SEQUENCE: 155

Leu Leu Ile Tyr Asp Ala Ser Ser Arg Ala Thr
1               5                   10

<210> SEQ ID NO 156
<211> LENGTH: 7
<212> TYPE: PRT
<213> ORGANISM: Artificial Sequence
<220> FEATURE:
<223> OTHER INFORMATION: LCDR3

<400> SEQUENCE: 156

Gln Gln Ser Val Lys Ser Asn
1               5

<210> SEQ ID NO 157
<211> LENGTH: 108
<212> TYPE: PRT
<213> ORGANISM: Artificial Sequence
<220> FEATURE:
<223> OTHER INFORMATION: VL

<400> SEQUENCE: 157

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ile Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Val Lys Ser Asn Thr
                85                  90                  95

Phe Gly Gln Gly Thr Lys Val Glu Ile Lys Arg Thr
            100                 105

<210> SEQ ID NO 158
<211> LENGTH: 120
<212> TYPE: PRT
<213> ORGANISM: Artificial Sequence
<220> FEATURE:
<223> OTHER INFORMATION: VH

<400> SEQUENCE: 158

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Ala Trp Val Arg Gln Met Pro Gly Lys Gly Leu Glu Trp Met
        35                  40                  45

Gly Phe Ile Tyr Pro Ser Asn Ser Ala Thr Gln Tyr Ser Pro Ser Phe
    50                  55                  60

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Asn Glu Tyr Ser Asp Ser Tyr Phe Asp Val Trp Gly Gln
            100                 105                 110

Gly Thr Leu Val Thr Val Ser Ser
        115                 120


<210> SEQ ID NO 159
<211> LENGTH: 324
<212> TYPE: DNA
<213> ORGANISM: Artificial Sequence
<220> FEATURE:
<223> OTHER INFORMATION: VL DNA

<400> SEQUENCE: 159

gatatcgtgc tgacccagag cccggcgacc ctgagcctga gcccgggtga acgtgccacc      60

ctgagctgca gagcgagcca gatcgtttct tcttacctgg cttggtacca gcagaaaccg     120

ggccaggccc cgcgtctatt aatctacgac gcttcttctc gtgcgaccgg cattccggcg     180

cgttttagcg gcagcggatc cggcaccgat ttcaccctga ccattagcag cctggaaccg     240

gaagactttg cgacctatta ttgccagcag tctgttaaat ctaacacctt tggccagggc     300

acgaaagttg aaattaaacg tacg                                            324


<210> SEQ ID NO 160
<211> LENGTH: 360
<212> TYPE: DNA
<213> ORGANISM: Artificial Sequence
<220> FEATURE:
<223> OTHER INFORMATION: VH DNA

<400> SEQUENCE: 160

gaagtgcaat tggtgcagag cggtgcggaa gtgaaaaaac cgggcgaaag cctgaaaatt      60

agctgcaaag gctccggata tagcttcaac aactactgga tcgcttgggt gcgccagatg     120

ccgggcaaag gtctcgagtg gatgggcttc atctacccgt ctaacagcgc tacccagtat     180

agcccgagct ttcagggcca ggtgaccatt agcgcggata aaagcatcag caccgcgtat     240

ctgcaatgga gcagcctgaa agcgagcgat accgcgatgt attattgcgc gcgtgacaac     300

gaatactctg actcttactt cgatgtttgg ggccaaggca ccctggtgac tgttagctca     360


<210> SEQ ID NO 161
<211> LENGTH: 10
<212> TYPE: PRT
<213> ORGANISM: Artificial Sequence
<220> FEATURE:
<223> OTHER INFORMATION: HCDR1

<400> SEQUENCE: 161

Gly Tyr Ser Phe Asn Asn Tyr Trp Ile Ala
1               5                   10


<210> SEQ ID NO 162
<211> LENGTH: 20
<212> TYPE: PRT
<213> ORGANISM: Artificial Sequence
<220> FEATURE:
<223> OTHER INFORMATION: HCDR2

<400> SEQUENCE: 162
```

```
Trp Met Gly Phe Ile Tyr Pro Ser Asn Ser Ala Thr Gln Tyr Ser Pro
1               5                   10                  15

Ser Phe Gln Gly
            20


<210> SEQ ID NO 163
<211> LENGTH: 11
<212> TYPE: PRT
<213> ORGANISM: Artificial Sequence
<220> FEATURE:
<223> OTHER INFORMATION: HCDR3

<400> SEQUENCE: 163

Asp Asn Glu Tyr Ser Asp Ser Tyr Phe Asp Val
1               5                   10


<210> SEQ ID NO 164
<211> LENGTH: 11
<212> TYPE: PRT
<213> ORGANISM: Artificial Sequence
<220> FEATURE:
<223> OTHER INFORMATION: LCDR1

<400> SEQUENCE: 164

Arg Ala Ser Gln Ile Val Ser Ser Tyr Leu Ala
1               5                   10


<210> SEQ ID NO 165
<211> LENGTH: 11
<212> TYPE: PRT
<213> ORGANISM: Artificial Sequence
<220> FEATURE:
<223> OTHER INFORMATION: LCDR2

<400> SEQUENCE: 165

Leu Leu Ile Tyr Asp Ala Ser Ser Arg Ala Thr
1               5                   10


<210> SEQ ID NO 166
<211> LENGTH: 8
<212> TYPE: PRT
<213> ORGANISM: Artificial Sequence
<220> FEATURE:
<223> OTHER INFORMATION: LCDR3

<400> SEQUENCE: 166

Gln Gln Ser Asn Gly Trp Leu Pro
1               5


<210> SEQ ID NO 167
<211> LENGTH: 109
<212> TYPE: PRT
<213> ORGANISM: Artificial Sequence
<220> FEATURE:
<223> OTHER INFORMATION: VL

<400> SEQUENCE: 167

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ile Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
```

```
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Asn Gly Trp Leu Pro
                85                  90                  95

Thr Phe Gly Gln Gly Thr Lys Val Glu Ile Lys Arg Thr
            100                 105


<210> SEQ ID NO 168
<211> LENGTH: 120
<212> TYPE: PRT
<213> ORGANISM: Artificial Sequence
<220> FEATURE:
<223> OTHER INFORMATION: VH

<400> SEQUENCE: 168

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Ala Trp Val Arg Gln Met Pro Gly Lys Gly Leu Glu Trp Met
        35                  40                  45

Gly Phe Ile Tyr Pro Ser Asn Ser Ala Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Asn Glu Tyr Ser Asp Ser Tyr Phe Asp Val Trp Gly Gln
            100                 105                 110

Gly Thr Leu Val Thr Val Ser Ser
        115                 120


<210> SEQ ID NO 169
<211> LENGTH: 327
<212> TYPE: DNA
<213> ORGANISM: Artificial Sequence
<220> FEATURE:
<223> OTHER INFORMATION: VL DNA

<400> SEQUENCE: 169

gatatcgtgc tgacccagag cccggcgacc ctgagcctga gcccgggtga acgtgccacc      60

ctgagctgca gagcgagcca gatcgtttct tcttacctgg cttggtacca gcagaaaccg     120

ggccaggccc cgcgtctatt aatctacgac gcttcttctc gtgcgaccgg cattccggcg     180

cgttttagcg gcagcggatc cggcaccgat ttcaccctga ccattagcag cctggaaccg     240

gaagactttg cgacctatta ttgccagcag tctaacggtt ggctgccgac ctttggccag     300

ggcacgaaag ttgaaattaa acgtacg                                         327


<210> SEQ ID NO 170
<211> LENGTH: 360
<212> TYPE: DNA
<213> ORGANISM: Artificial Sequence
<220> FEATURE:
<223> OTHER INFORMATION: VH DNA

<400> SEQUENCE: 170

gaagtgcaat tggtgcagag cggtgcggaa gtgaaaaaac cgggcgaaag cctgaaaatt      60
```

-continued

```
agctgcaaag gctccggata tagcttcaac aactactgga tcgcttgggt gcgccagatg    120

ccgggcaaag gtctcgagtg gatgggtttc atctacccgt ctaacagcgc tacccagtat    180

agcccgagct ttcagggcca ggtgaccatt agcgcggata aaagcatcag caccgcgtat    240

ctgcaatgga gcagcctgaa agcgagcgat accgcgatgt attattgcgc gcgtgacaac    300

gaatactctg actcttactt cgatgtttgg ggccaaggca ccctggtgac tgttagctca    360
```

```
<210> SEQ ID NO 171
<211> LENGTH: 10
<212> TYPE: PRT
<213> ORGANISM: Artificial Sequence
<220> FEATURE:
<223> OTHER INFORMATION: HCDR1

<400> SEQUENCE: 171

Gly Tyr Ser Phe Asn Asn Tyr Trp Ile Ala
1               5                   10


<210> SEQ ID NO 172
<211> LENGTH: 20
<212> TYPE: PRT
<213> ORGANISM: Artificial Sequence
<220> FEATURE:
<223> OTHER INFORMATION: HCDR2

<400> SEQUENCE: 172

Trp Met Gly Phe Ile Tyr Pro Ser Asn Ser Ala Thr Gln Tyr Ser Pro
1               5                   10                  15

Ser Phe Gln Gly
            20


<210> SEQ ID NO 173
<211> LENGTH: 11
<212> TYPE: PRT
<213> ORGANISM: Artificial Sequence
<220> FEATURE:
<223> OTHER INFORMATION: HCDR3

<400> SEQUENCE: 173

Asp Asn Glu Tyr Ser Asp Ser Tyr Phe Asp Val
1               5                   10


<210> SEQ ID NO 174
<211> LENGTH: 11
<212> TYPE: PRT
<213> ORGANISM: Artificial Sequence
<220> FEATURE:
<223> OTHER INFORMATION: LCDR1

<400> SEQUENCE: 174

Arg Ala Ser Gln Ile Val Ser Ser Tyr Leu Ala
1               5                   10


<210> SEQ ID NO 175
<211> LENGTH: 11
<212> TYPE: PRT
<213> ORGANISM: Artificial Sequence
<220> FEATURE:
<223> OTHER INFORMATION: LCDR2

<400> SEQUENCE: 175

Leu Leu Ile Tyr Asp Ala Ser Ser Arg Ala Thr
1               5                   10
```

<210> SEQ ID NO 176
<211> LENGTH: 8
<212> TYPE: PRT
<213> ORGANISM: Artificial Sequence
<220> FEATURE:
<223> OTHER INFORMATION: LCDR3

<400> SEQUENCE: 176

Gln Gln Ser Glu Gln Val Pro Thr
1               5

<210> SEQ ID NO 177
<211> LENGTH: 109
<212> TYPE: PRT
<213> ORGANISM: Artificial Sequence
<220> FEATURE:
<223> OTHER INFORMATION: VL

<400> SEQUENCE: 177

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ile Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Glu Gln Val Pro Thr
                85                  90                  95

Thr Phe Gly Gln Gly Thr Lys Val Glu Ile Lys Arg Thr
            100                 105

<210> SEQ ID NO 178
<211> LENGTH: 120
<212> TYPE: PRT
<213> ORGANISM: Artificial Sequence
<220> FEATURE:
<223> OTHER INFORMATION: VH

<400> SEQUENCE: 178

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Asn Tyr
            20                  25                  30

Trp Ile Ala Trp Val Arg Gln Met Pro Gly Lys Gly Leu Glu Trp Met
        35                  40                  45

Gly Phe Ile Tyr Pro Ser Asn Ser Ala Thr Gln Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Asn Glu Tyr Ser Asp Ser Tyr Phe Asp Val Trp Gly Gln
            100                 105                 110

Gly Thr Leu Val Thr Val Ser Ser
        115                 120

<210> SEQ ID NO 179

-continued

<211> LENGTH: 327
<212> TYPE: DNA
<213> ORGANISM: Artificial Sequence
<220> FEATURE:
<223> OTHER INFORMATION: VL DNA

<400> SEQUENCE: 179
gatatcgtgc tgacccagag cccggcgacc ctgagcctga gcccgggtga acgtgccacc 60
ctgagctgca gagcgagcca gatcgtttct tcttacctgg cttggtacca gcagaaaccg 120
ggccaggccc cgcgtctatt aatctacgac gcttcttctc gtgcgaccgg cattccggcg 180
cgttttagcg gcagcggatc cggcaccgat ttcaccctga ccattagcag cctggaaccg 240
gaagactttg cggtgtatta ttgccagcag tctgaacagg ttccgactac ctttggccag 300
ggcacgaaag ttgaaattaa acgtacg 327

<210> SEQ ID NO 180
<211> LENGTH: 360
<212> TYPE: DNA
<213> ORGANISM: Artificial Sequence
<220> FEATURE:
<223> OTHER INFORMATION: VH DNA

<400> SEQUENCE: 180
gaagtgcaat tggtgcagag cggtgcggaa gtgaaaaaac cgggcgaaag cctgaaaatt 60
agctgcaaag gctccggata tagcttcaac aactactgga tcgcttgggt gcgccagatg 120
ccgggcaaag gtctcgagtg gatgggcttc atctacccgt ctaacagcgc tacccagtat 180
agcccgagct ttcagggcca ggtgaccatt agcgcggata aaagcatcag caccgcgtat 240
ctgcaatgga gcagcctgaa agcgagcgat accgcgatgt attattgcgc gcgtgacaac 300
gaatactctg actcttactt cgatgtttgg ggccaaggca ccctggtgac tgttagctca 360

<210> SEQ ID NO 181
<211> LENGTH: 197
<212> TYPE: PRT
<213> ORGANISM: Homo sapiens
<220> FEATURE:
<223> OTHER INFORMATION: IL17C

<400> SEQUENCE: 181

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
            20                  25                  30

Thr Pro His Cys Tyr Ser Ala Glu Glu Leu Pro Leu Gly Gln Ala Pro
        35                  40                  45

Pro His Leu Leu Ala Arg Gly Ala Lys Trp Gly Gln Ala Leu Pro Val
    50                  55                  60

Ala Leu Val Ser Ser Leu Glu Ala Ala Ser His Arg Gly Arg His Glu
65                  70                  75                  80

Arg Pro Ser Ala Thr Thr Gln Cys Pro Val Leu Arg Pro Glu Glu Val
                85                  90                  95

Leu Glu Ala Asp Thr His Gln Arg Ser Ile Ser Pro Trp Arg Tyr Arg
            100                 105                 110

Val Asp Thr Asp Glu Asp Arg Tyr Pro Gln Lys Leu Ala Phe Ala Glu
        115                 120                 125

Cys Leu Cys Arg Gly Cys Ile Asp Ala Arg Thr Gly Arg Glu Thr Ala
    130                 135                 140

-continued

```
Ala Leu Asn Ser Val Arg Leu Leu Gln Ser Leu Leu Val Leu Arg Arg
145                 150                 155                 160

Arg Pro Cys Ser Arg Asp Gly Ser Gly Leu Pro Thr Pro Gly Ala Phe
                165                 170                 175

Ala Phe His Thr Glu Phe Ile His Val Pro Val Gly Cys Thr Cys Val
            180                 185                 190

Leu Pro Arg Ser Val
        195


<210> SEQ ID NO 182
<211> LENGTH: 866
<212> TYPE: PRT
<213> ORGANISM: Homo sapiens
<220> FEATURE:
<223> OTHER INFORMATION: IL17RA

<400> SEQUENCE: 182

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300
```

-continued

```
Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
        355                 360                 365

Asp Leu Ile Pro Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
        435                 440                 445

Arg Gly Thr Arg Ala Lys Trp Gln Ala Leu Leu Gly Arg Gly Ala Pro
    450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
        595                 600                 605

Pro Leu Leu Pro Pro Gly Thr Gly Ile Val Lys Arg Ala Pro Leu Val
    610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
        675                 680                 685

Gly Ala Ala Val Arg Leu Ala Leu Ala Gly Glu Gly Glu Ala Cys Pro
    690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
```

```
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
    770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
    850                 855                 860

Ser Ala
865


<210> SEQ ID NO 183
<211> LENGTH: 667
<212> TYPE: PRT
<213> ORGANISM: Homo sapiens
<220> FEATURE:
<223> OTHER INFORMATION: IL17RE

<400> SEQUENCE: 183

Met Gly Ser Ser Arg Leu Ala Ala Leu Leu Leu Pro Leu Leu Leu Ile
1               5                   10                  15

Val Ile Asp Leu Ser Asp Ser Ala Gly Ile Gly Phe Arg His Leu Pro
            20                  25                  30

His Trp Asn Thr Arg Cys Pro Leu Ala Ser His Thr Asp Asp Ser Phe
        35                  40                  45

Thr Gly Ser Ser Ala Tyr Ile Pro Cys Arg Thr Trp Trp Ala Leu Phe
    50                  55                  60

Ser Thr Lys Pro Trp Cys Val Arg Val Trp His Cys Ser Arg Cys Leu
65                  70                  75                  80

Cys Gln His Leu Leu Ser Gly Gly Ser Gly Leu Gln Arg Gly Leu Phe
                85                  90                  95

His Leu Leu Val Gln Lys Ser Lys Lys Ser Ser Thr Phe Lys Phe Tyr
            100                 105                 110

Arg Arg His Lys Met Pro Ala Pro Ala Gln Arg Lys Leu Leu Pro Arg
        115                 120                 125

Arg His Leu Ser Glu Lys Ser His His Ile Ser Ile Pro Ser Pro Asp
    130                 135                 140

Ile Ser His Lys Gly Leu Arg Ser Lys Arg Thr Gln Pro Ser Asp Pro
145                 150                 155                 160

Glu Thr Trp Glu Ser Leu Pro Arg Leu Asp Ser Gln Arg His Gly Gly
                165                 170                 175

Pro Glu Phe Ser Phe Asp Leu Leu Pro Glu Ala Arg Ala Ile Arg Val
            180                 185                 190

Thr Ile Ser Ser Gly Pro Glu Val Ser Val Arg Leu Cys His Gln Trp
        195                 200                 205

Ala Leu Glu Cys Glu Glu Leu Ser Ser Pro Tyr Asp Val Gln Lys Ile
```

```
    210                 215                 220

Val Ser Gly Gly His Thr Val Glu Leu Pro Tyr Glu Phe Leu Leu Pro
225                 230                 235                 240

Cys Leu Cys Ile Glu Ala Ser Tyr Leu Gln Glu Asp Thr Val Arg Arg
                245                 250                 255

Lys Lys Cys Pro Phe Gln Ser Trp Pro Glu Ala Tyr Gly Ser Asp Phe
            260                 265                 270

Trp Lys Ser Val His Phe Thr Asp Tyr Ser Gln His Thr Gln Met Val
        275                 280                 285

Met Ala Leu Thr Leu Arg Cys Pro Leu Lys Leu Glu Ala Ala Leu Cys
    290                 295                 300

Gln Arg His Asp Trp His Thr Leu Cys Lys Asp Leu Pro Asn Ala Thr
305                 310                 315                 320

Ala Arg Glu Ser Asp Gly Trp Tyr Val Leu Glu Lys Val Asp Leu His
                325                 330                 335

Pro Gln Leu Cys Phe Lys Phe Ser Phe Gly Asn Ser Ser His Val Glu
            340                 345                 350

Cys Pro His Gln Thr Gly Ser Leu Thr Ser Trp Asn Val Ser Met Asp
        355                 360                 365

Thr Gln Ala Gln Gln Leu Ile Leu His Phe Ser Ser Arg Met His Ala
    370                 375                 380

Thr Phe Ser Ala Ala Trp Ser Leu Pro Gly Leu Gly Gln Asp Thr Leu
385                 390                 395                 400

Val Pro Pro Val Tyr Thr Val Ser Gln Ala Arg Gly Ser Ser Pro Val
                405                 410                 415

Ser Leu Asp Leu Ile Ile Pro Phe Leu Arg Pro Gly Cys Cys Val Leu
            420                 425                 430

Val Trp Arg Ser Asp Val Gln Phe Ala Trp Lys His Leu Leu Cys Pro
        435                 440                 445

Asp Val Ser Tyr Arg His Leu Gly Leu Leu Ile Leu Ala Leu Leu Ala
    450                 455                 460

Leu Leu Thr Leu Leu Gly Val Val Leu Ala Leu Thr Cys Arg Arg Pro
465                 470                 475                 480

Gln Ser Gly Pro Gly Pro Ala Arg Pro Val Leu Leu Leu His Ala Ala
                485                 490                 495

Asp Ser Glu Ala Gln Arg Arg Leu Val Gly Ala Leu Ala Glu Leu Leu
            500                 505                 510

Arg Ala Ala Leu Gly Gly Gly Arg Asp Val Ile Val Asp Leu Trp Glu
        515                 520                 525

Gly Arg His Val Ala Arg Val Gly Pro Leu Pro Trp Leu Trp Ala Ala
    530                 535                 540

Arg Thr Arg Val Ala Arg Glu Gln Gly Thr Val Leu Leu Leu Trp Ser
545                 550                 555                 560

Gly Ala Asp Leu Arg Pro Val Ser Gly Pro Asp Pro Arg Ala Ala Pro
                565                 570                 575

Leu Leu Ala Leu Leu His Ala Ala Pro Arg Pro Leu Leu Leu Leu Ala
            580                 585                 590

Tyr Phe Ser Arg Leu Cys Ala Lys Gly Asp Ile Pro Pro Pro Leu Arg
        595                 600                 605

Ala Leu Pro Arg Tyr Arg Leu Leu Arg Asp Leu Pro Arg Leu Leu Arg
    610                 615                 620

Ala Leu Asp Ala Arg Pro Phe Ala Glu Ala Thr Ser Trp Gly Arg Leu
625                 630                 635                 640
```

-continued

```
Gly Ala Arg Gln Arg Arg Gln Ser Arg Leu Glu Leu Cys Ser Arg Leu
                645                 650                 655

Glu Arg Glu Ala Ala Arg Leu Ala Asp Leu Gly
            660                 665


<210> SEQ ID NO 184
<211> LENGTH: 21
<212> TYPE: DNA
<213> ORGANISM: Artificial Sequence
<220> FEATURE:
<223> OTHER INFORMATION: Primer

<400> SEQUENCE: 184

atgaggaccg ctatccacag a                                              21


<210> SEQ ID NO 185
<211> LENGTH: 16
<212> TYPE: DNA
<213> ORGANISM: Artificial Sequence
<220> FEATURE:
<223> OTHER INFORMATION: Primer

<400> SEQUENCE: 185

cccgtccgtg catcga                                                    16


<210> SEQ ID NO 186
<211> LENGTH: 20
<212> TYPE: DNA
<213> ORGANISM: Artificial Sequence
<220> FEATURE:
<223> OTHER INFORMATION: Probe

<400> SEQUENCE: 186

tggccttcgc cgagtgcctg                                                20
```

ANTAGONISTS OF IL17C FOR THE TREATMENT OF INFLAMMATORY DISORDERS

CROSS REFERENCE TO RELATED APPLICATIONS

This patent application is a continuation of U.S. application Ser. No. 14/351,162 filed Apr. 11, 2014 which is the U.S. National Stage pf PCT/EP2012/070736 filed Oct. 19, 2012, which claims the benefit of priority from U.S. provisional application Ser. No. 61/548,744, filed Oct. 19, 2011 and EP Application No. 11185763.7, filed Oct. 19, 2011, each of which is herein incorporated by reference in its entirety.

FIELD OF THE INVENTION

The present application relates to antagonists of IL17C for use in the treatment of inflammatory disorders, such as arthritis. Exemplary IL17C antagonists are IL17C-specific antibodies or fragments thereof, such as human anti-IL17C antibodies.

BACKGROUND

IL17C is a secreted disulfide-linked homodimer of the IL17 protein family. In vitro it has been shown that IL17C stimulates the release of TNF-α and IL-1β from the monocytic cell line THP-1 (Li et al. (2000) Proc. Natl. Acad. Sci. U.S.A 97, 773-8). IL17C can induce the mRNA expression of inflammatory cytokines such as IL-1β, IL-6 and IL-23 in peritoneal exudates cells (PECS) and the 3T3 cell line (Yamaguchi et al. (2007) J. Immunol 179, 7128-36. In vivo CD4+ T cells transduced with IL17C exacerbated collagen induced arthritis (CIA) in mice and mice reconstituted with bone marrow cells transduced with IL17C suffered from severe collagen induced arthritis. IL17C was reported to bind IL-17 receptor E (IL17RE/Fc) and seemed to activate NF-κB (Calhoun (2007) Bachelor's Thesis: Generation of proof of concept molecules: Neutralizing monoclonal antibodies to IL17C; Oregon State University, University Honours College; Gaffen (2009) Nat Rev. Immunol 9, 556-67) and was also reported to affect nuclear IkappaB family member, IkBζ in Th17 cells activation in IL17C deficient mice (Chang et al. (2011) Immunity 35, 1-11). IL17C expression in normal tissue seems to be restricted to adult and fetal kidney. The mRNA expression of IL17C in the arthritic paws of CIA mice is highly elevated. Hwang et al. described IL17C expression in mononuclear cells of synovial fluid and peripheral blood of rheumatoid arthritis patients (Hwang & Kim (2005) Mol Cells 19, 180-184).

WO 99/060127 describes the cloning of IL17C (PRO1122). WO 99/060127 loosely associated certain disorders with IL17C, including arthritis (e.g., osteoarthritis, rheumatoid arthritis, psoriatic arthritis), sepsis, ulcerative colitis, psoriasis, multiple sclerosis, type I diabetes, giant cell arthritis, systemic lupus erythematosus and Sjogren's syndrome. It is also contemplated that the compounds of WO 99/060127 may be used to treat various conditions, including those characterized by overexpression and/or activation of the disease-associated genes identified herein. However, no experimental proof is provided for this speculative function of IL17C. The same holds true for WO 2005/065711.

The present invention for the first time demonstrates in in vivo experiments that antagonists of IL17C are highly effective in the treatment of inflammatory disorders.

SUMMARY OF THE INVENTION

The present invention provides antagonists of IL17C for use in the treatment of an inflammatory disorder.

The inflammatory disorder treated with the antagonists of the present invention may be any inflammatory disorder selected from arthritis, such as rheumatoid arthritis, asthma, sepsis, an autoimmune disease, such as inflammatory bowel disease, COPD (chronic obstructive pulmonary disease), systemic lupus erythematosus (SLE) and sarcoidosis. In particular embodiments, said inflammatory disorder is arthritis.

The antagonists of IL17C of the present invention may be any antagonist. Preferably, said antagonist is an antibody or antibody fragment, such as a monoclonal antibody. Said antibody may be an antibody or fragment thereof specific for IL17C or an antibody or fragment thereof specific for the receptor of IL17C.

BRIEF DESCRIPTION OF THE FIGURES

FIG. 2 shows quality control results based on size exclusion chromatography (SEC).

FIG. 3 shows results of $EC_{50}$ determination in ELISA. All purified chimeric human-mouse chimeric IgG2a antibodies were titrated on mouse IL17C starting with a concentration of 100 nM.

FIG. 4 shows monovalent affinities of anti-IL17C antibodies. Affinities were determined by solution equilibrium titration (SET) using Fab fragments.

FIG. 5 shows $IC_{50}$ values determined in the IL-17 receptor E inhibition assay described in example 11.

FIG. 6 shows results of a mouse serum stability assay. 11 purified IgGs showed acceptable production yields and specific binding to mouse IL17C after 24 h incubation with mouse serum.

DETAILED DESCRIPTION OF THE INVENTION

Figure 1A:
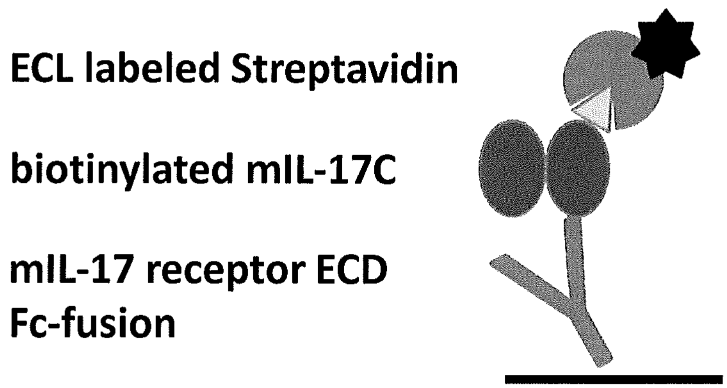
FIG. 1A shows the assay set up for a receptor interaction assay. ECD fusion proteins of IL17 receptors were coated on a Multi-array® 384-well plate. Biotinylated mouse IL17C was applied and detected via Streptavidin.

The present invention demonstrates that IL17C is a valid target for the treatment of inflammatory disorders. In this respect, the invention provides, in one aspect, methods of using an IL17C antagonist to bring about a prophylactic or therapeutic benefit in the treatment of inflammatory disorders.

The present invention provides therapeutic methods comprising the administration of a therapeutically effective amount of an IL17C antagonist to a subject in need of such treatment. A "therapeutically effective amount" or "effective amount", as used herein, refers to the amount of an IL17C antagonist necessary to elicit the desired biological response. In accordance with the subject invention, the therapeutic effective amount is the amount of an IL17C antagonist necessary to treat and/or prevent an inflammatory disorder.

The terms "inflammatory disorder" or "inflammatory disease" are used interchangeably and as used herein refer to any abnormality associated with inflammation. Examples of disorders associated with inflammation include acne vulgaris, arthritis, such as rheumatoid arthritis, asthma, autoimmune diseases, chronic prostatitis, COPD (chronic obstructive pulmonary disease), glomerulonephritis, hypersensitivities, inflammatory bowel diseases, pelvic inflammatory disease, reperfusion injury, sarcoidosis, transplant rejection, vasculitis, interstitial cystitis and sepsis. Inflammatory disorders may be chronic or acute. Examples of autoimmune diseases include ankylosing spondylitis, Crohn's Disease, Diabetes mellitus type I, gastritis, Guillain-Barré syndrome, idiopathic thrombocytopenic purpura, Lupus erythematosus, multiple sclerosis, psoriasis, psoratic arthritis, restless leg syndrome, rheumatoid arthritis, sarcoidosis, scleroderma, systemic lupus erythematosus and ulcerative colitis.

Arthritis can manifest itself as the primary form of a disease. This is for example the case for osteoarthritis, rheumatoid arthritis, septic arthritis, gout and pseudo-gout, juvenile idiopathic arthritis, Still's disease and ankylosing spondylitis. Other forms of arthritis are secondary to other disease, e.g. Ehlers-Danlos syndrome, sarcoidosis, Henoch-Schönlein purpura, psoriatic arthritis, reactive arthritis, haemochromatosis, hepatitis, Wegener's granulomatosis (and other vasculitis syndromes), Lyme disease, familial Mediterranean fever, hyperimmunoglobulinaemia D with recurrent fever, TNF receptor associated periodic syndrome and inflammatory bowel disease (including Crohn's disease and ulcerative colitis).

The term "pulmonary inflammation" encompasses any inflammatory lung disease, acute chronic bronchitis, chronic obstructive lung disease, pulmonary fibrosis, Goodpasture's syndrome, and any pulmonary condition in which white blood cells may play a role including but not limited to idiopathic pulmonary fibrosis and any other autoimmune lung disease.

The term "IL17C" refers to a protein known as interleukin 17C (identified in HUGO Gene Nomenclature Committee (HGNC) by ID 5983 and in Mouse genome Informatics (MGI) database by ID 2446486). IL17C is some older publications referred to as CX2 or IL-21, however, it should not be confused with IL-21 cytokine, which is specifically expressed in activated CD4' T cells, but not most of other tissues (Parrish-Novak et al (2000). Nature 408 (6808): 57-63). Human IL-21 is located on Chromosome 4 and is identified in HGNC database by ID 6005. Human IL17C is located on Chromosome 16 and has the amino acid sequence of (UniProt Q9P0M4:

```
                                    (SEQ ID NO: 181)
MTLLPGLLFLTWLHTCLAHHDPSLRGHPHSHGTPHCYSAEELPLGQAPP

HLLARGAKWGQALPVALVSSLEAASHRGRHERPSATTQCPVLRPEEVLE

ADTHQRSISPWRYRVDTDEDRYPQKLAFAECLCRGCIDARTGRETAALN

SVRLLQSLLVLRRRPCSRDGSGLPTPGAFAFHTEFIHVPVGCTCVLPRS

V
```

The term "IL17RA" refers to a protein known as interleukin 17 receptor A. Human IL17RA has the amino acid sequence of (UniProt Q96F46):

```
                                    (SEQ ID NO: 182)
MGAARSPPSAVPGPLLGLLLLLLGVLAPGGASLRLLDHRALVCSQPGLN

CTVKNSTCLDDSWIHPRNLTPSSPKDLQIQLHFAHTQQGDLFPVAHIEW

TLQTDASILYLEGAELSVLQLNTNERLCVRFEFLSKLRHHHRRWRFTFS

HFVVDPDQEYEVTVHHLPKPIPDGDPNHQSKNFLVPDCEHARMKVTTPC

MSSGSLWDPNITVETLEAHQLRVSFTLWNESTHYQILLTSFPHMENHSC

FEHMHHIPAPRPEEFHQRSNVTLTLRNLKGCCRHQVQIQPFFSSCLNDC

LRHSATVSCPEMPDTPEPIPDYMPLWVYWFITGISILLVGSVILLIVCM

TWRLAGPGSEKYSDDTKYTDGLPAADLIPPPLKPRKVWIIYSADHPLYV

DVVLKFAQFLLTACGTEVALDLLEEQAISEAGVMTWVGRQKQEMVESNS

KIIVLCSRGTRAKWQALLGRGAPVRLRCDHGKPVGDLFTAAMNMILPDF

KRPACFGTYVVCYFSEVSCDGDVPDLFGAAPRYPLMDRFEEVYFRIQDL

EMFQPGRMHRVGELSGDNYLRSPGGRQLRAALDRFRDWQVRCPDWFECE

NLYSADDQDAPSLDEEVFEEPLLPPGTGIVKRAPLVREPGSQACLAIDP

LVGEEGGAAVAKLEPHLQPRGQPAPQPLHTLVLAAEEGALVAAVEPGPL

ADGAAVRLALAGEGEACPLLGSPGAGRNSVLFLPVDPEDSPLGSSTPMA

SPDLLPEDVREHLEGLMLSLFEQSLSCQAQGGCSRPAMVLTDPHTPYEE

EQRQSVQSDQGYISRSSPQPPEGLTEMEEEEEEEQDPGKPALPLSPEDL

ESLRSLQRQLLFRQLQKNSGWDTMGSESEGPSA
```

The term "IL17RE" refers to a protein known as interleukin 17 receptor E. Human IL17RE has the amino acid sequence of (UniProt Q8NFR9):

(SEQ ID NO: 183)

```
MGSSRLAALLLPLLLIVIDLSDSAGIGFRHLPHWNTRCPLASHTDDSFT
GSSAYIPCRTWWALFSTKPWCVRWVHCSRCLCQHLLSGGSGLQRGLFHL
LVQKSKKSSTFKFYRRHKMPAPAQRKLLPRRHLSEKSHHISIPSPDISH
KGLRSKRTQPSDPETWESLPRLDSQRHGGPEFSFDLLPEARAIRVTISS
GPEVSVRLCHQWALECEELSSPYDVQKIVSGGHTVELPYEFLLPCLCIE
ASYLQEDTVRRKKCPFQSWPEAYGSDFWKSVHFTDYSQHTQMVMALTLR
CPLKLEAALCQRHDWHTLCKDLPNATARESDGWYVLEKVDLHPQLCFKF
SFGNSSHVECPHQTGSLTSWNVSMDTQAQQLILHFSSRMHATFSAAWSL
PGLGQDTLVPPVYTVSQARGSSPVSLDLIIPFLRPGCCVLVWRSDVQFA
WKHLLCPDVSYRHLGLLILALLALLTLLGVVLALTCRRPQSGPGPARPV
LLLHAADSEAQRRLVGALAELLRAALGGGRDVIVDLWEGRHVARVGPLP
WLWAARTRVAREQGTVLLLWSGADLRPVSGPDPRAAPLLALLHAAPRPL
LLLAYFSRLCAKGDIPPPLRALPRYRLLRDLPRLLRALDARPFAEATSW
GRLGARQRRQSRLELCSRLEREAARLADLG
```

An "antagonist of IL17C" and an "IL17C antagonist", as used herein, refer to IL17C antagonists in the broadest sense. Any molecule which inhibits the activity or function of IL17C, or which by any other way exerts an effect on IL17C is included. The term IL17C antagonist includes, but is not limited to, antibodies or antibody fragments specifically binding to IL17C, inhibitory nucleic acids specific for IL17C or small organic molecules specific for IL17C. Also within the meaning of the term IL17C antagonist are antibodies or antibody fragments specifically binding to the receptor of IL17C, inhibitory nucleic acids specific for the receptor of IL17C or small organic molecules specific for the receptor of IL17C. The term IL17C antagonist also refers to non-antibody scaffold molecules, such as fibronectin scaffolds, ankyrins, maxybodies/avimers, protein A-derived molecules, anticalins, affilins, protein epitope mimetics (PEMs) or the like.

Inhibitory nucleic acids include, but are not limited to, antisense DNA, triplex-forming oligonucleotides, external guide sequences, siRNA and microRNA. Useful inhibitory nucleic acids include those that reduce the expression of RNA encoding IL17C by at least 20, 30, 40, 50, 60, 70, 80, 90 or 95 percent compared to controls. Inhibitory nucleic acids and methods of producing them are well known in the art. siRNA design software is available.

Small organic molecules (SMOLs) specific for IL17C or the receptor of IL17C may be identified via natural product screening or screening of chemical libraries. Typically the molecular weight of SMOLs is below 500 Dalton, more typically from 160 to 480 Daltons. Other typical properties of SMOLs are one or more of the following:

The partition coefficient log P is in the range from −0.4 to +5.6

The molar refractivity is from 40 to 130

The number of atoms is from 20 to 70

For reviews see Ghose et al. (1999) J Combin Chem: 1, 55-68 and Lipinski et al (1997) Adv Drug Del Rev: 23, 3-25.

Preferably, an IL17C antagonist for use in the present invention is an antibody specific for IL17C or specific for the receptor of IL17C. Such an antibody may be of any type, such as a murine, a rat, a chimeric, a humanized or a human antibody. A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The term "chimeric antibody" or functional chimeric antibody fragment is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster.

In one aspect antigen binding can be performed by "fragments" of an intact antibody. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) *Nature* 341:544-546), which consists of a VH domain; and an isolated complementary determining region (CDR).

A "single chain Fragment (scFv)" is a single protein chain in which the VL and VH regions pair to form monovalent molecules (known as single chain Fv (scFv); see, e.g., Bird et al., (1988) *Science* 242:423-426; and Huston et al., (1988) *Proc. Natl. Acad. Sci.* 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "isolated" refers to a compound which can be e.g. an antibody or antibody fragment that is substantially free of other antibodies or antibody fragments having different antigenic specificities. Moreover, an isolated antibody or antibody fragment may be substantially free of other cellular material and/or chemicals.

The term "monoclonal antibody" as used herein refers to a preparation of antibody molecules of single molecular composition. A monoclonal antibody composition displays a unique binding site having a unique binding specificity and affinity for particular epitopes.

As used herein, an antibody "binds specifically to", "specifically binds to", is "specific to/for" or "specifically recognizes" an antigen (here, IL17C or, alternatively, the receptor of IL17C) if such antibody is able to discriminate between such antigen and one or more reference antigen(s), since binding specificity is not an absolute, but a relative property. The reference antigen(s) may be one or more closely related antigen(s), which are used as reference points, e.g. IL17A or IL17B. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions of IL17C or the receptor of IL17C, or between one or more key amino acid residues or stretches of amino acid residues of IL17C or the receptor of IL17C.

"Cross competes" means the ability of an antibody, antibody fragment or other antigen-binding moieties to interfere with the binding of other antibodies, antibody fragments or antigen-binding moieties to a specific antigen in a standard competitive binding assay. The ability or extent to which an antibody, antibody fragment or other antigen-binding moieties is able to interfere with the binding of another antibody, antibody fragment or antigen-binding moieties to a specific antigen, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731. Cross-competition is present if the antibody or antibody fragment under investigation reduces the binding of one of the antibodies described in Table 1 to IL17C by 60% or more, specifically by 70% or more and more specifically by 80% or more and if one of the antibodies described in Table 1 reduces the binding of said antibody or antibody fragment to IL17C by 60% or more, specifically by 70% or more and more specifically by 80% or more.

The term "epitope" includes any proteinaceous region which is specifically recognized by an immunoglobulin or T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope. An epitope can comprise those residues to which the antibody binds and may be "linear" or "conformational." The term "linear epitope" refers to an epitope wherein all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformations. In a conformational epitope, the points of interaction occur across amino acid residues on the protein that are separated from one another.

"Binds the same epitope as" means the ability of an antibody, antibody fragment or other antigen-binding moiety to bind to a specific antigen and having the same epitope as the exemplified antibody. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')2 fragment, a Fab fragment, scFv or constructs comprising single immunoglobulin variable domains or single domain antibody polypeptides, e.g. single heavy chain variable domains or single light chain variable domains. The F(ab')2 or Fab may be engineered to minimize or completely remove the intermolecular disulphide interactions that occur between the CH1 and CL domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67, Rothe et al., J. Mol. Biol. (2008) 376:1182; and U.S. Pat. No. 6,300,064 issued to Knappik et al., which are hereby incorporated by reference in their entirety.

Any antibody specific for IL17C may be used with the present invention. Exemplary antibodies include antibodies in the prior art, such as A: rat $IgG_{2A}$ monoclonal anti-mouse IL17C antibody (R&D Systems; clone 311522, #MAB23061), B: rat $IgG_{2A}$ monoclonal anti-mouse IL17C antibody (R&D Systems; clone 311523, #MAB2306), and C: rat anti-mouse IL17C (US Biological; clone: 8B28, #I8439-20R3) (take from Example 4).

Other antibodies that may be used to practice the present invention include the anti-IL17C antibodies available from Abnova (Walnut, Calif., USA; Catalog #H00027189-B01P, #H00027189-D01 and #H00027189-D01P) and the anti-IL17C antibodies available from antibodies-online GmbH (Aachen, Germany; Catalog #ABIN525892, #ABIN327411, #ABIN525893, #ABIN221340, #ABIN221341, #ABIN221342 and #ABIN525891). Other antibodies specific for IL17C that may be used with the present invention are those isolated and described in the present invention itself, i.e. those listed in Table 1.

Compositions of the invention may be used for therapeutic or prophylactic applications. The invention, therefore, includes a pharmaceutical composition containing an inventive antibody (or functional antibody fragment) and a pharmaceutically acceptable carrier or excipient therefor. In a related aspect, the invention provides a method for treating an inflammatory disorder. Such method contains the steps of administering to a subject in need thereof an effective amount of the pharmaceutical composition that contains an inventive antibody as described or contemplated herein.

In certain aspects, the present invention provides methods for the treatment of an inflammatory disorder in a subject, said method comprising the step of administering an IL17C antagonist to said subject. "Subject", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably the subject is a primate, most preferably a human.

In certain aspects, the present invention provides methods for the treatment of an inflammatory disorder, said method comprising the step of administering to a subject an IL17C antagonist, wherein said IL17C antagonist can bind to IL17C with an affinity of about less than 100 nM, more preferably less than about 60 nM, and still more preferably less than about 30 nM. Further preferred are antibodies or antibody fragments that bind to IL17C with an affinity of less than about 10 nM, and more preferably less than about 3 nM.

In certain aspects said IL17C antagonist is an antibody or antibody fragment specific for IL17C and said antibody or antibody fragment is cross-reactive with IL17C of another species, such as IL17C from mouse, rat, rhesus monkey and/or cynomolgus monkey. In certain aspects said IL17C antibody or antibody fragment is an isolated antibody or antibody fragment specific for IL17C. In another embodiment said isolated antibody or antibody fragment specific for IL17C is a monoclonal antibody or antibody fragment. In a further embodiment said isolated monoclonal antibody or antibody fragment is an isolated monoclonal antibody specific for a polypeptide comprising the amino acid sequence of SEQ ID NO: 181. In a further embodiment said isolated monoclonal antibody or antibody fragment is an isolated monoclonal antibody specific for a polypeptide consisting of the amino acid sequence of SEQ ID NO: 181. In a further embodiment said isolated monoclonal antibody or antibody fragment is cross-reactive with IL17C of another species, such as IL17C from mouse, rat, rhesus monkey and/or cynomolgus monkey.

In certain aspects, said antibody or antibody fragment specific for IL17C is a human, humanized or chimeric antibody. In certain aspects, said antibody or antibody fragment specific for IL17C is a human synthetic antibody. In certain aspects the present invention provides an isolated monoclonal antibody or antibody fragment specific for a polypeptide comprising the amino acid sequence of SEQ ID NO: 181 wherein said antibody or antibody fragment is a human, humanized or chimeric antibody. In certain aspects the present invention provides an isolated monoclonal antibody or antibody fragment specific for a polypeptide consisting of the amino acid sequence of SEQ ID NO: 181 wherein said antibody or antibody fragment is a human, humanized or chimeric antibody. In certain aspects, said antibody or antibody fragment specific for a polypeptide consisting of the amino acid sequence of SEQ ID NO: 181 is a human synthetic antibody or antibody fragment.

In a certain aspect, the present invention provides a composition comprising an IL17C antagonist capable of antagonizing IL17C in an inflammatory disorder, said composition further comprising one or more pharmaceutically acceptable carriers and/or diluents. In certain aspects, antagonists of IL17C, such as antibodies specific for IL17C, may antagonize any of the roles of IL17C in an inflammatory disorder.

In another aspect, the present invention provides a method for the prophylaxis of an inflammatory disorder in a subject, said method comprising administering an IL17C antagonist to said subject. "Prophylaxis" as used in this context refers to methods which aim to prevent the onset of a disease or which delay the onset of a disease.

In certain aspects, the present invention provides a composition comprising an IL17C antagonist useful in the treatment of an inflammatory disorder, said composition further comprising one or more pharmaceutically acceptable carriers and/or diluents.

In certain aspects, the present invention provides IL17C antagonists for use in the treatment of an inflammatory disorder.

In other aspects, the present invention provides the use of an IL17C antagonist in the preparation of a medicament for the treatment of an inflammatory disorder.

In other aspects, the present invention provides a method for the treatment of an inflammatory disorder in a subject, comprising administering to the subject an antagonist of IL17C.

In particular aspects, the IL17C antagonists of the present invention are administered subcutaneously. In other aspects, the IL17C antagonists of the present invention are administered intra-venously, intra-articularly or intra-spinally.

The compositions of the present invention are preferably pharmaceutical compositions comprising an IL17C antagonist and a pharmaceutically acceptable carrier, diluent or excipient, for the treatment of an inflammatory disorder. Such carriers, diluents and excipients are well known in the art, and the skilled artisan will find a formulation and a route of administration best suited to treat a subject with the IL17C antagonists of the present invention.

In certain aspects, the present invention provides a method for the treatment or prophylaxis of an inflammatory disorder in a subject, comprising the step of administering to the subject an effective amount of an antagonist of IL17C. In certain aspects said subject is a human. In alternative aspects said subject is a rodent, such as a rat or a mouse.

In certain aspects, said antagonist of IL17C is an antibody or antibody fragment specific for IL17C. In certain aspects said antagonist is an antibody or antibody fragment specific for a polypeptide comprising the amino acid sequence of SEQ ID NO: 181. In alternative aspects, said antagonist of IL17C is an antibody or antibody fragment specific for the receptor of IL17C.

In certain aspects, said antibody or antibody fragment specific for IL17C blocks the binding of IL17C to the receptor of IL17C. In alternative aspects, said antibody or antibody fragment specific for the receptor of IL17C blocks the binding of IL17C to the receptor of IL17C.

In certain aspects, said antibody or antibody fragment specific for IL17C blocks the binding of IL17C to the receptor of IL17, wherein said receptor is IL17RE. In alternative aspects, said antibody or antibody fragment specific for the receptor of IL17C blocks the binding of IL17C to IL17RE.

In certain aspects, said antibody or antibody fragment specific for IL17C blocks the binding of IL17C to IL17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In certain aspects the $IC_{50}$ concentration can be determined by ELISA; SET, FACS or MSD (Meso Scale Discovery).

In certain aspects, said antibody or antibody fragment specific for IL17C blocks the binding of IL17C to one or more receptors of IL17C. In alternative aspects, said antibody or antibody fragment specific for the receptor of IL17C blocks the binding of IL17C to receptors of IL17C, wherein the receptors of IL17 include IL17RE and IL17RA. In alternative aspects, said antibody or antibody fragment specific for the receptor of IL17C blocks the binding of IL17C to IL17RE and IL17RA.

In certain aspects, the present invention provides an antagonist of IL17C for use in the treatment or prophylaxis of an inflammatory disorder. In certain aspects, said treatment or prophylaxis comprises the step of administering to a subject an effective amount of the antagonist of IL17C. In certain aspects, said subject is a human. In alternative aspects, said subject is a rodent, such as a rat or a mouse.

In another aspect, the disclosure pertains to an isolated monoclonal antibody or fragment thereof that cross-competes with an antibody described in Table 1. In a certain embodiment, the disclosure pertains to an isolated monoclonal antibody or fragment thereof that cross-competes with an antibody comprising 6 CDRs of one of the antibodies described in Table 1. In a certain embodiment, the disclosure pertains to an isolated monoclonal antibody or fragment thereof that cross-competes with an antibody described in Table 1 and reduces the specific binding of one of the antibodies described in Table 1 by at least 20%, 30%, 40%, 50%, 60%, 70%, 80% or 90% in an ELISA-based cross-competition. In a certain embodiment, the disclosure pertains to an isolated monoclonal antibody or fragment thereof that cross-competes with an antibody described in Table 1 and reduces the specific binding of one of the antibodies described in Table 1 to IL17C by at least 20%, 30%, 40%, 50%, 60%, 70%, 80% or 90% in an ELISA-based cross-competition.

In another aspect, the disclosure pertains to an isolated monoclonal antibody or fragment thereof that interacts with (e.g., by binding, stabilizing, spatial distribution) the same epitope as an antibody described in Table 1.

In one aspect, the disclosure pertains to an isolated monoclonal antibody or fragment thereof comprising 6 CDRs defined by Kabat of any of the antibodies in Table 1. In another aspect, the disclosure pertains to an isolated monoclonal antibody or fragment thereof comprising 6 CDRs defined by Kabat of each of the antibodies in Table 1.

In one aspect, the disclosure pertains to an isolated monoclonal antibody or fragment thereof comprising a VH and a VL of any of the antibodies in Table 1.

In another aspect, the disclosure pertains to a nucleic acid encoding an isolated monoclonal antibody or fragment thereof wherein the nucleic acid comprises a VH and a VL of any of the antibodies in Table 1.

In another aspect, the disclosure pertains to a nucleic acid encoding an isolated monoclonal antibody or fragment thereof having at least 75%, 80%, 85%, 90%, 95%, 98%, 99% sequence identity to nucleic acids described in Table 1.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| MOR# | | SEQ ID NO: | [aa]/DNA |
|---|---|---|---|
| 12740 | HCDR1 | 1 | GGTFSIYAIS |
| | HCDR2 | 2 | WMGGIIPILGIANYAQKFQG |
| | HCDR3 | 3 | DATHSYYHDY |
| | LCDR1 | 4 | TGTSSDVGSYETVS |
| | LCDR2 | 5 | VMIYEVSDRPS |
| | LCDR3 | 6 | GSFAHWGSW |
| | VL | 7 | DIALTQPASVSGSPGQSITISCTGTSSDVGSYET VSWYQQHPGKAPKVMIYEVSDRPSGVSNRFSGSK SGNTASLTISGLQAEDEADYYCGSFAHWGSWVFG GGTKLTVLGQ |

TABLE 1-continued

| MOR# | | SEQ ID NO: | [aa]/DNA |
|---|---|---|---|
| | VH | 8 | QVQLVQSGAEVKKPGSSVKVSCKASGGTFSIYAI<br>SWVRQAPGQGLEWMGGIIPILGIANYAQKFQGRV<br>TITADESTSTAYMELSSLRSEDTAVYYCARDATH<br>SYYHDYWGQGTLVTVSS |
| | VL (DNA) | 9 | GATATCGCGCTGACCCAGCCGGCGAGCGTGAGCG<br>GTAGCCCGGGCCAGAGCATTACCATTAGCTGCAC<br>CGGCACCAGCAGCGATGTGGGCTCTTACGAAACT<br>GTGTCTTGGTACCAGCAGCATCCGGGCAAGGCGC<br>CGAAAGTTATGATCTACGAAGTTTCTGACCGTCC<br>GAGCGGCGTGAGCAACCGTTTTAGCGGATCCAAA<br>AGCGGCAACACCGCGAGCCTGACCATTAGCGGCC<br>TGCAAGCGGAAGACGAAGCGGATTATTACTGCGG<br>TTCTTTCGCTCATTGGGGTTCTTGGGTGTTTGGC<br>GGCGGCACGAAGTTAACCGTTCTTGGCCAG |
| | VH (DNA) | 10 | CAGGTGCAATTGGTGCAGAGCGGTGCCGAAGTGA<br>AAAAACCGGGCAGCAGCGTGAAAGTTAGCTGCAA<br>AGCATCCGGAGGGACGTTTTCTATCTACGCTATC<br>TCTTGGGTGCGCCAGGCCCCGGGCCAGGGCCTCG<br>AGTGGATGGGCGGTATCATCCCGATCCTGGGCAT<br>CGCGAACTACGCCCAGAAATTTCAGGGCCGGGTG<br>ACCATTACCGCCGATGAAAGCACCAGCACCGCCT<br>ATATGGAACTGAGCAGCCTGCGCAGCGAAGATAC<br>GGCCGTGTATTATTGCGCGCGTGACGCTACTCAT<br>TCTTACTACCATGATTACTGGGGCCAAGGCACCC<br>TGGTGACTGTTAGCTCA |
| 12741 | HCDR1 | 11 | GGTFSSYAIS |
| | HCDR2 | 12 | WMGMIMPEVGMADYAQKFQG |
| | HCDR3 | 13 | DFIAVGSLEIWHYYYGLDV |
| | LCDR1 | 14 | SGDNIGEHYAS |
| | LCDR2 | 15 | LVISYDNERPS |
| | LCDR3 | 16 | QSWTSQKPDY |
| | VL | 17 | DIELTQPPSVSVSPGQTASITCSGDNIGEHYASW<br>YQQKPGQAPVLVISYDNERPSGIPERFSGSNSGN<br>TATLTISGTQAEDEADYYCQSWTSQKPDYVFGGG<br>TKLTVLGQ |
| | VH | 18 | QVQLVQSGAEVKKPGSSVKVSCKASGGTFSSYAI<br>SWVRQAPGQGLEWMGMIMPEVGMADYAQKFQGRV<br>TITADESTSTAYMELSSLRSEDTAVYYCARDFIA<br>VGSLEIWHYYYGLDVWGQGTLVTVSS |
| | VL (DNA) | 19 | GATATCGAACTGACCCAGCCGCCGAGCGTGAGCG<br>TGAGCCCGGGCCAGACCGCGAGCATTACCTGTAG<br>CGGCGATAACATCGGTGAACATTACGCTTCTTGG<br>TACCAGCAGAAACCGGGCCAGGCGCCGGTGCTGG<br>TGATCTCTTACGACAACGAACGTCCGAGCGGCAT<br>CCCGGAACGTTTTAGCGGATCCAACAGCGGCAAC<br>ACCGCGACCCTGACCATTAGCGGCACCCAGGCGG<br>AAGACGAAGCGGATTATTACTGCCAGTCTTGGAC<br>TTCTCAGAAACCGGACTACGTGTTTGGCGGCGGC<br>ACGAAGTTAACCGTTCTTGGCCAG |
| | VH (DNA) | 20 | CAGGTGCAATTGGTGCAGAGCGGTGCCGAAGTGA<br>AAAAACCGGGCAGCAGCGTGAAAGTTAGCTGCAA<br>AGCATCCGGAGGGACGTTTAGCAGCTATGCGATT<br>AGCTGGGTGCGCCAGGCCCCGGGCCAGGGCCTCG<br>AGTGGATGGGCATGATCATGCCGGAAGTTGGCAT<br>GGCTGACTACGCCCAGAAATTTCAGGGCCGGGTG<br>ACCATTACCGCCGATGAAAGCACCAGCACCGCCT<br>ATATGGAACTGAGCAGCCTGCGCAGCGAAGATAC<br>GGCCGTGTATTATTGCGCGCGTGACTTCATCGCT<br>GTTGGTTCTCTGGAAATCTGGCATTACTACTACG<br>GTCTGGATGTTTGGGGCCAAGGCACCCTGGTGAC<br>TGTTAGCTCA |
| 12742 | HCDR1 | 21 | GGTFSSYGIS |
| | HCDR2 | 22 | WMGRIIPIFGTAYYAQKFQG |
| | HCDR3 | 23 | DMRYHDYMYYYGSDQFDV |
| | LCDR1 | 24 | SGSSSNIGSDIVS |
| | LCDR2 | 25 | LLIYYNNLRPS |
| | LCDR3 | 26 | QSWDWASLAM |
| | VL | 27 | DIVLTQPPSVSGAPGQRVTISCSGSSSNIGSDIV<br>SWYQQLPGTAPKLLIYYNNLRPSGVPDRFSGSKS<br>GTSASLNTGLQAEDEADYYCQSWDWASLAMVFGG<br>GTKLTVLGQ |
| | VH | 28 | QVQLVQSGAEVKKPGSSVKVSCKASGGTFSSYGI<br>SWVRQAPGQGLEWMGRHPIFGTAYYAQKFQGRVT<br>ITADESTSTAYMELSSLRSEDTAVYYCARDMRYH<br>DYWPYYYGSDQFDVWGQGTLVTVSS |

TABLE 1-continued

| MOR# | | SEQ ID NO: | [aa]/DNA |
|---|---|---|---|
| | VL (DNA) | 29 | GATATCGTGCTGACCCAGCCGCCGAGCGTGAGCG GTGCACCGGGCCAGCGCGTGACCATTAGCTGTAG CGGCAGCAGCAGCAACATTGGTTCTGACATCGTG TCTTGGTACCAGCAGCTGCCGGGCACGGCGCCGA AACTGCTGATCTACTACAACAACCTGCGCCCGAG CGGCGTGCCGGATCGCTTTAGCGGATCCAAAAGC GGCACCAGCGCCAGCCTGGCGATTACCGGCCTGC AAGCAGAAGACGAAGCGGATTATTACTGCCAGTC TTGGGACTGGGCTTCTCTGGCTATGGTGTTTGGC GGCGGCACGAAGTTAACCGTTCTTGGCCAG |
| | VH (DNA) | 30 | CAGGTGCAATTGGTGCAGAGCGGTGCCGAAGTGA AAAAACCGGGCAGCAGCGTGAAAGTTAGCTGCAA AGCATCCGGAGGGACGTTTTCTTCTTACGGTATC TCTTGGGTGCGCCAGGCCCCGGGCCAGGGCCTCG AGTGGATGGGCCGTATCATCCCGATCTTCGGCAC TGCGTACTACGCCCAGAAATTTCAGGGCCGGGTG ACCATTACCGCCGATGAAAGCACCAGCACCGCCT ATATGGAACTGAGCAGCCTGCGCAGCGAAGATAC GGCCGTGTATTATTGCGCGCGTGACATGCGTTAC CATGACTACTGGCCGTACTACTACGGTTCTGACC AGTTCGATGTTTGGGGCCAAGGCACCCTGGTGAC TGTTAGCTCA |
| 12743 | HCDR1 | 31 | GYTFTSNFIH |
| | HCDR2 | 32 | WMGWISPYNGDTNYAQKFQG |
| | HCDR3 | 33 | ESVYYGSDYGYNGMDI |
| | LCDR1 | 34 | SGDNLGEEYVS |
| | LCDR2 | 35 | LVIYDDTKRPS |
| | LCDR3 | 36 | ASWDLWSVE |
| | VL | 37 | DIELTQPPSVSVSPGQTASITCSGDNLGEEYVSW YQQKPGQAPVLVIYDDTKRPSGIPERFSGSNSGN TATLTISGTQAEDEADYYCASWDLWSVEVFGGGT KLTVLGQ |
| | VH | 38 | QVQLVQSGAEVKKPGASVKVSCKASGYTFTSNFI HWVRQAPGQGLEWMGWISPYNGDTNYAQKFQGRV TMTRDTSISTAYMELSRLRSEDTAVYYCARESVY YGSDYGYNGMDIWGQGTLVTVSS |
| | VL (DNA) | 39 | GATATCGAACTGACCCAGCCGCCGAGCGTGAGCG TGAGCCCGGGCCAGACCGCGAGCATTACCTGTAG CGGCGATAACCTGGGTGAAGAATACGTTTCTTGG TACCAGCAGAAACCGGGCCAGGCGCCGGTGCTGG TGATCTACGACGACACTAAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCGCTTCTTGGGA CCTGTGGTCTGTTGAAGTGTTTGGCGGCGGCACG AAGTTAACCGTTCTTGGCCAG |
| | VH (DNA) | 40 | CAGGTGCAATTGGTGCAGAGCGGTGCGGAAGTGA AAAAACCGGGTGCCAGCGTGAAAGTTAGCTGCAA AGCGTCCGGATATACCTTCACTTCTAACTTCATC CATTGGGTGCGCCAGGCCCCGGGCCAGGGCCTCG AGTGGATGGGCTGGATCTCTCCGTACAACGGCGA CACGAACTACGCGCAGAAATTTCAGGGCCGGGTG ACCATGACCCGTGATACCAGCATTAGCACCGCGT ATATGGAACTGAGCCGTCTGCGTAGCGAAGATAC GGCCGTGTATTATTGCGCGCGTGAATCTGTTTAC TACGGTTCTGACTACGGTTACAACGGTATGGATA TCTGGGGCCAAGGCACCCTGGTGACTGTTAGCTC A |
| 12744 | HCDR1 | 41 | GYTFTSNFIH |
| | HCDR2 | 42 | WMGWISPYNGDTNYAQKFQG |
| | HCDR3 | 43 | ESVYYGSDYGYNGMDI |
| | LCDR1 | 44 | SGDNLGEEYVS |
| | LCDR2 | 45 | LVIYDDTKRPS |
| | LCDR3 | 46 | ASWAFYSSQ |
| | VL | 47 | DIELTQPPSVSVSPGQTASITCSGDNLGEEYVSW YQQKPGQAPVLVIYDDTKRPSGIPERFSGSNSGN TATLTISGTQAEDEADYYCASWAFYSSQVFGGGT KLTVLGQ |
| | VH | 48 | QVQLVQSGAEVKKPGASVKVSCKASGYTFTSNFI HWVRQAPGQGLEWMGWISPYNGDTNYAQKFQGRV TMTRDTSISTAYMELSRLRSEDTAVYYCARESVY YGSDYGYNGMDIWGQGTLVTVSS |
| | VL (DNA) | 49 | GATATCGAACTGACCCAGCCGCCGAGCGTGAGCG TGAGCCCGGGCCAGACCGCGAGCATTACCTGTAG CGGCGATAACCTGGGTGAAGAATACGTTTCTTGG TACCAGCAGAAACCGGGCCAGGCGCCGGTGCTGG |

TABLE 1-continued

| MOR# | | SEQ ID NO: | [aa]/DNA |
|---|---|---|---|
| | | | TGATCTACGACGACACTAAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCGCTTCTTGGGC TTTCTACTCTTCTCAGGTGTTTGGCGGCGGCACG AAGTTAACCGTTCTTGGCCAG |
| | VH (DNA) | 50 | CAGGTGCAATTGGTGCAGAGCGGTGCGGAAGTGA AAAAACCGGGTGCCAGCGTGAAAGTTAGCTGCAA AGCGTCCGGATATACCTTCACTTCTAACTTCATC CATTGGGTGCGCCAGGCCCCGGGCCAGGGCCTCG AGTGGATGGGCTGGATCTCTCCGTACAACGGCGA CACGAACTACGCGCAGAAATTTCAGGGCCGGGTG ACCATGACCCGTGATACCAGCATTAGCACCGCGT ATATGGAACTGAGCCGTCTGCGTAGCGAAGATAC GGCCGTGTATTATTGCGCGCGTGAATCTGTTTAC TACGGTTCTGACTACGGTTACAACGGTATGGATA TCTGGGGCCAAGGCACCCTGGTGACTGTTAGCTC A |
| 12745 | HCDR1 | 51 | GYTFTSNFIH |
| | HCDR2 | 52 | WMGWISPYNGDTNYAQKFQG |
| | HCDR3 | 53 | ESVYYGSDYGYNGMDI |
| | LCDR1 | 54 | SGDNLGEEYVS |
| | LCDR2 | 55 | LVIYDDTKRPS |
| | LCDR3 | 56 | SAWATWSVA |
| | VL | 57 | DIELTQPPSVSVSPGQTASITCSGDNLGEEYVSW YQQKPGQAPVLVIYDDTKRPSGIPERFSGSNSGN TATLTISGTQAEDEADYYCSAWATWSVAVFGGGT KLTVLGQ |
| | VH | 58 | QVQLVQSGAEVKKPGASVKVSCKASGYTFTSNFI HWVRQAPGQGLEWMGWISPYNGDTNYAQKFQGRV TMTRDTSISTAYMELSRLRSEDTAVYYCARESVY YGSDYGYNGMDIWGQGTLVTVSS |
| | VL (DNA) | 59 | GATATCGAACTGACCCAGCCGCCGAGCGTGAGCG TGAGCCCGGGCCAGACCGCGAGCATTACCTGTAG CGGCGATAACCTGGGTGAAGAATACGTTTCTTGG TACCAGCAGAAACCGGGCCAGGCGCCGGTGCTGG TGATCTACGACGACACTAAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCTCTGCTTGGGC TACTTGGTCTGTTGCTGTGTTTGGCGGCGGCACG AAGTTAACCGTTCTTGGCCAG |
| | VH (DNA) | 60 | CAGGTGCAATTGGTGCAGAGCGGTGCGGAAGTGA AAAAACCGGGTGCCAGCGTGAAAGTTAGCTGCAA AGCGTCCGGATATACCTTCACTTCTAACTTCATC CATTGGGTGCGCCAGGCCCCGGGCCAGGGCCTCG AGTGGATGGGCTGGATCTCTCCGTACAACGGCGA CACGAACTACGCGCAGAAATTTCAGGGCCGGGTG ACCATGACCCGTGATACCAGCATTAGCACCGCGT ATATGGAACTGAGCCGTCTGCGTAGCGAAGATAC GGCCGTGTATTATTGCGCGCGTGAATCTGTTTAC TACGGTTCTGACTACGGTTACAACGGTATGGATA TCTGGGGCCAAGGCACCCTGGTGACTGTTAGCTC A |
| 12746 | HCDR1 | 61 | GYTFTSNFIH |
| | HCDR2 | 62 | WMGWISPYNGDTNYAQKFQG |
| | HCDR3 | 63 | ESVYYGSDYGYNGMDI |
| | LCDR1 | 64 | SGDNLGEEYVS |
| | LCDR2 | 65 | LVIYDDTKRPS |
| | LCDR3 | 66 | SSWTHFSNI |
| | VL | 67 | DIELTQPPSVSVSPGQTASITCSGDNLGEEYVSW YQQKPGQAPVLVIYDDTKRPSGIPERFSGSNSGN TATLTISGTQAEDEADYYCSSWTHFSNIVFGGGT KLTVLGQ |
| | VH | 68 | QVQLVQSGAEVKKPGASVKVSCKASGYTFTSNFI HWVRQAPGQGLEWMGWISPYNGDTNYAQKFQGRV TMTRDTSISTAYMELSRLRSEDTAVYYCARESVY YGSDYGYNGMDIWGQGTLVTVSS |
| | VL (DNA) | 69 | GATATCGAACTGACCCAGCCGCCGAGCGTGAGCG TGAGCCCGGGCCAGACCGCGAGCATTACCTGTAG CGGCGATAACCTGGGTGAAGAATACGTTTCTTGG TACCAGCAGAAACCGGGCCAGGCGCCGGTGCTGG TGATCTACGACGACACTAAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCTCTTCTTGGAC |

TABLE 1-continued

| MOR# | | SEQ ID NO: | [aa]/DNA |
|---|---|---|---|
| | | | TCATTTCTCTAACATCGTGTTTGGCGGCGGCACG AAGTTAACCGTTCTTGGCCAG |
| | VH (DNA) | 70 | CAGGTGCAATTGGTGCAGAGCGGTGCGGAAGTGA AAAAACCGGGTGCCAGCGTGAAAGTTAGCTGCAA AGCGTCCGGATATACCTTCACTTCTAACTTCATC CATTGGGTGCGCCAGGCCCCGGGCCAGGGCCTCG AGTGGATGGGCTGGATCTCTCCGTACAACGGCGA CACGAACTACGCGCAGAAATTTCAGGGCCGGGTG ACCATGACCCGTGATACCAGCATTAGCACCGCGT ATATGGAACTGAGCCGTCTGCGTAGCGAAGATAC GGCCGTGTATTATTGCGCGCGTGAATCTGTTTAC TACGGTTCTGACTACGGTTACAACGGTATGGATA TCTGGGGCCAAGGCACCCTGGTGACTGTTAGCTC A |
| 12751 | HCDR1 | 71 | GDSVSSNSAAWN |
| | HCDR2 | 72 | WLGVIYYRSKWYINYADSVKS |
| | HCDR3 | 73 | EGIVGGWFAY |
| | LCDR1 | 74 | SGDKLGSKIAH |
| | LCDR2 | 75 | LVIYDDNERPS |
| | LCDR3 | 76 | QSWDYLSWSV |
| | VL | 77 | DIELTQPPSVSVSPGQTASITCSGDKLGSKIAHW YQQKPGQAPVLVIYDDNERPSGIPERFSGSNSGN TATLTISGTQAEDEADYYCQSWDYLSWSVVFGGG TKLTVLGQ |
| | VH | 78 | QVQLQQSGPGLVKPSQTLSLTCAISGDSVSSNSA AWNWIRQSPSRGLEWLGVIYYRSKWYINYADSVK SRITINPDTSKNQFSLQLNSVTPEDTAVYYCARE GIVGGWFAYWGQGTLVTVSS |
| | VL (DNA) | 79 | GATATCGAACTGACCCAGCCGCCGAGCGTGAGCG TGAGCCCGGGCCAGACCGCGAGCATTACCTGTAG CGGCGATAAACTGGGTTCTAAAATCGCTCATTGG TACCAGCAGAAACCGGGCCAGGCGCCGGTGCTGG TGATCTACGACGACAACGAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCCAGTCTTGGGA CTACCTGTCTTGGTCTGTTGTGTTTGGCGGCGGC ACGAAGTTAACCGTTCTTGGCCAG |
| | VH (DNA) | 80 | CAGGTGCAATTGCAGCAGAGCGGTCCGGGCCTGG TGAAACCGAGCCAGACCCTGAGCCTGACCTGCGC GATTTCCGGAGATAGCGTGAGCAGTAACTCTGCT GCTTGGAACTGGATTCGTCAGAGCCCGAGCCGTG GCCTCGAGTGGCTGGGCGTTATCTACTACCGTAG CAAATGGTACATCAACTATGCCGACAGCGTGAAA AGCCGCATTACCATTAACCCGGATACTTCGAAAA ACCAGTTTAGCCTGCAACTGAACAGCGTGACCCC GGAAGATACGGCCGTGTATTATTGCGCGCGTGAA GGTATCGTTGGTGGTTGGTTCGCTTACTGGGGCC AAGGCACCCTGGTGACTGTTAGCTCA |
| 12753 | HCDR1 | 81 | GDSVSSSSAAWN |
| | HCDR2 | 82 | WLGRIEYRSKWYNDYAVSVKS |
| | HCDR3 | 83 | EMYYYSGYGVFDV |
| | LCDR1 | 84 | SGDALGGEYVH |
| | LCDR2 | 85 | LVIYDDDKRPS |
| | LCDR3 | 86 | SSFDTWTSY |
| | VL | 87 | DIELTQPPSVSVSPGQTASITCSGDALGGEYVHW YQQKPGQAPVLVIYDDDKRPSGIPERFSGSNSGN TATLTISGTQAEDEADYYCSSFDTWTSYVFGGGT KLTVLGQ |
| | VH | 88 | QVQLQQSGPGLVKPSQTLSLTCAISGDSVSSSSA AWNWIRQSPSRGLEWLGRIEYRSKWYNDYAVSVK SRITINPDTSKNQFSLQLNSVTPEDTAVYYCARE MYYYSGYGVFDVWGQGTLVTVSS |
| | VL (DNA) | 89 | GATATCGAACTGACCCAGCCGCCGAGCGTGAGCG TGAGCCCGGGCCAGACCGCGAGCATTACCTGTAG CGGCGATGCTCTGGGTGGTGAATACGTTCATTGG TACCAGCAGAAACCGGGCCAGGCGCCGGTGCTGG TGATCTACGACGACGACAAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCTCTTCTTTCGA CACTTGGACTTCTTACGTGTTTGGCGGCGGCACG AAGTTAACCGTTCTTGGCCAG |
| | VH (DNA) | 90 | CAGGTGCAATTGCAGCAGAGCGGTCCGGGCCTGG TGAAACCGAGCCAGACCCTGAGCCTGACCTGCGC GATTTCCGGAGATAGCGTGAGCTCCTCTTCTGCT |

TABLE 1-continued

| MOR# | | SEQ ID NO: | [aa]/DNA |
|---|---|---|---|
| | | | GCTTGGAACTGGATTCGTCAGAGCCCGAGCCGTGGCCTCGAGTGGCTGGGCCGTATCGAATACCGTAGCAAATGGTACAACGACTATGCCGTGAGCGTGAAAAGCCGCATTACCATTAACCCGGATACTTCGAAAAACCAGTTTAGCCTGCAACTGAACAGCGTGACCCCGGAAGATACGGCCGTGTATTATTGCGCGCGTGAAATGTACTACTACTCTGGTTACGGTGTTTTCGATGTTTGGGGCCAAGGCACCCTGGTGACTGTTAGCTCA |
| 12754 | HCDR1 | 91 | GFTFSDYAMT |
| | HCDR2 | 92 | WVSVISYDGSLTYYADSVKG |
| | HCDR3 | 93 | DPGVWWLSYLDY |
| | LCDR1 | 94 | RASQDIISYLA |
| | LCDR2 | 95 | LLIYGASNLQG |
| | LCDR3 | 96 | QQYMIAPPN |
| | VL | 97 | DIQMTQSPSSLSASVGDRVTITCRASQDIISYLAWYQQKPGKAPKLLIYGASNLQGGVPSRFSGSGSGTDFTLTISSLQPEDFAVYYCQQYMIAPPNTFGQGTKVEIKRT |
| | VH | 98 | EVQLLESGGGLVQPGGSLRLSCAASGFTFSDYAMTWVRQAPGKGLEWVSVISYDGSLTYYADSVKGRFTISRDNSKNTLYLQMNSLRAEDTAVYYCARDPGVWWLSYLDYWGQGTLVTVSS |
| | VL (DNA) | 99 | GATATCCAGATGACCCAGAGCCCGAGCAGCCTGAGCGCCAGCGTGGGCGATCGCGTGACCATTACCTGCAGAGCCAGCCAGGACATTATCTCTTACCTGGCTTGGTACCAGCAGAAACCGGGCAAAGCGCCGAAACTATTAATCTACGGTGCTTCTAACCTGCAAGGCGGCGTGCCGAGCCGCTTTAGCGGCAGCGGATCCGGCACCGATTTCACCCTGACCATTAGCTCTCTGCAACCGGAAGACTTTGCGGTGTATTATTGCCAGCAGTACATGATCGCTCCACCGAACACCTTTGGCCAGGGCACGAAAGTTGAAATTAAACGTACG |
| | VH (DNA) | 100 | GAAGTGCAATTGCTGGAAAGCGGCGGTGGCCTGGTGCAGCCGGGTGGCAGCCTGCGTCTGAGCTGCGCGGCGTCCGGATTCACCTTTTCTGACTACGCTATGACTTGGGTGCGCCAGGCCCCGGGCAAAGGTCTCGAGTGGGTTTCCGTTATCTCTTACGACGGTTCTCTGACCTACTATGCGGATAGCGTGAAAGGCCGCTTTACCATCAGCCGCGATAATTCGAAAAACACCCTGTATCTGCAAATGAACAGCCTGCGTGCGGAAGATACGGCCGTGTATTATTGCGCGCGTGACCCGGGTGTTTGGTGGCTGTCTTACCTGGATTACTGGGGCCAAGGCACCCTGGTGACTGTTAGCTCA |
| 12755 | HCDR1 | 101 | GDSVSSNSAAWN |
| | HCDR2 | 102 | WLGKTYYRSTWSNDYAESVKS |
| | HCDR3 | 103 | EMDSLTRSASSIAFDY |
| | LCDR1 | 104 | SGDNLREHYVH |
| | LCDR2 | 105 | LVIYDDTERPS |
| | LCDR3 | 106 | ATRDWSNV |
| | VL | 107 | DIELTQPPSVSVSPGQTASITCSGDNLREHYVHWYQQKPGQAPVLVIYDDTERPSGIPERFSGSNSGNTATLTISGTQAEDEADYYCATRDWSNVVFGGGTKLTVLGQ |
| | VH | 108 | QVQLQQSGPGLVKPSQTLSLTCAISGDSVSSNSAAWNWIRQSPSRGLEWLGKTYYRSTWSNDYAESVKSRITINPDTSKNQFSLQLNSVTPEDTAVYYCAREMDSLTRSASSIAFDYWGQGTLVTVSS |
| | VL (DNA) | 109 | GATATCGAACTGACCCAGCCGCCGAGCGTGAGCGTGAGCCCGGGCCAGACCGCGAGCATTACCTGTAGCGGCGATAACCTGCGTGAACATTACGTTCATTGGTACCAGCAGAAACCGGGCCAGGCGCCGGTGCTGGTGATCTACGACGACACTGAACGTCCGAGCGGCATCCCGGAACGTTTTAGCGGATCCAACAGCGGCAACACCGCGACCCTGACCATTAGCGGCACCCAGGCGGAAGACGAAGCGGATTATTACTGCGCTACTCGTGACTGGTCTAACGTTGTGTTTGGCGGCGGCACGAAGTTAACCGTTCTTGGCCAG |
| | VH (DNA) | 110 | CAGGTGCAATTGCAGCAGAGCGGTCCGGGCCTGGTGAAACCGAGCCAGACCCTGAGCCTGACCTGCGCGATTTCCGGAGATAGCGTGAGCAGTAACTCTGCTGCTTGGAACTGGATTCGTCAGAGCCCGAGCCGTGGCCTCGAGTGGCTGGGCAAAACCTACTACCGTAGCACTTGGTCTAACGACTATGCCGAAAGCGTGAAAAGCCGCATTACCATTAACCCGGATACTTCGAAAAACCAGTTTAGCCTGCAACTGAACAGCGTGACCCC |

TABLE 1-continued

| MOR# | | SEQ ID NO: | [aa]/DNA |
|---|---|---|---|
| | | | GGAAGATACGGCCGTGTATTATTGCGCGCGTGAA ATGGACTCTCTGACTCGTTCTGCTTCTTCTATCG CTTTCGATTACTGGGGCCAAGGCACCCTGGTGAC TGTTAGCTCA |
| 12756 | HCDR1 | 111 | GDSVSDNSVAWN |
| | HCDR2 | 112 | WLGRIYYRSKWYNDYAVSVKS |
| | HCDR3 | 113 | EVLLFPARSYGTGMDV |
| | LCDR1 | 114 | SGDNLPSKYVH |
| | LCDR2 | 115 | LVIYDDNERPS |
| | LCDR3 | 116 | GVADMPRQMK |
| | VL | 117 | DIELTQPPSVSVSPGQTASITCSGDNLPSKYVHW YQQKPGQAPVLVIYDDNERPSGIPERFSGSNSGN TATLTISGTQAEDEADYYCGVADMPRQMKVFGGG TKLTVLGQ |
| | VH | 118 | QVQLQQSGPGLVKPSQTLSLTCAISGDSVSDNSV AWNWIRQSPSRGLEWLGRIYYRSKWYNDYAVSVK SRITINPDTSKNQFSLQLNSVTPEDTAVYYCARE VLLFPARSYGTGMDVWGQGTLVTVSS |
| | VL (DNA) | 119 | GATATCGAACTGACCCAGCCGCCGAGCGTGAGCG TGAGCCCGGGCCAGACCGCGAGCATTACCTGTAG CGGCGATAACCTGCCGTCTAAATACGTTCATTGG TACCAGCAGAAACCGGGCCAGGCGCCGGTGCTGG TGATCTACGACGACAACGAACGTCCGAGCGGCAT CCCGGAACGTTTTAGCGGATCCAACAGCGGCAAC ACCGCGACCCTGACCATTAGCGGCACCCAGGCGG AAGACGAAGCGGATTATTACTGCGGTGTTGCTGA CATGCCGCGTCAGATGAAAGTGTTTGGCGGCGGC ACGAAGTTAACCGTTCTTGGCCAG |
| | VH (DNA) | 120 | CAGGTGCAATTGCAGCAGAGCGGTCCGGGCCTGG TGAAACCGAGCCAGACCCTGAGCCTGACCTGCGC GATTTCCGGAGATAGCGTGAGCGACAACTCTGTT GCTTGGAACTGGATTCGTCAGAGCCCGAGCCGTG GCCTCGAGTGGCTGGGCCGTATCTACTACCGTAG CAAATGGTACAACGACTATGCCGTGAGCGTGAAA AGCCGCATTACCATTAACCCGGATACTTCGAAAA ACCAGTTTAGCCTGCAACTGAACAGCGTGACCCC GGAAGATACGGCCGTGTATTATTGCGCGCGTGAA GTTCTGCTGTTCCCGGCTCGTTCTTACGGTACTG GTATGGATGTTTGGGGCCAAGGCACCCTGGTGAC TGTTAGCTCA |
| 12757 | HCDR1 | 121 | GFTFSSYAMS |
| | HCDR2 | 122 | WVSFISSGGSETFYADSVKG |
| | HCDR3 | 123 | VSYIYYYSWVLFDV |
| | LCDR1 | 124 | RASQGIGTALN |
| | LCDR2 | 125 | LLIYDVSSLQS |
| | LCDR3 | 126 | QQGLFLPF |
| | VL | 127 | DIQMTQSPSSLSASVGDRVTITCRASQGIGTALN WYQQKPGKAPKLLIYDVSSLQSGVPSRFSGSGSG TDFTLTISSLQPEDFATYYCQQGLFLPFTFGQGT KVEIKRT |
| | VH | 128 | EVQLLESGGGLVQPGGSLRLSCAASGFTFSSYAM SWVRQAPGKGLEWVSFISSGGSETFYADSVKGRF TISRDNSKNTLYLQMNSLRAEDTAVYYCARVSYI YYYSWVLFDVWGQGTLVTVSS |
| | VL (DNA) | 129 | GATATCCAGATGACCCAGAGCCCGAGCAGCCTGA GCGCCAGCGTGGGCGATCGCGTGACCATTACCTG CAGAGCCAGCCAGGGTATTGGTACTGCTCTGAAC TGGTACCAGCAGAAACCGGGCAAAGCGCCGAAAC TATTAATCTACGACGTTTCTTCTCTGCAAAGCGG CGTGCCGAGCCGCTTTAGCGGCAGCGGATCCGGC ACCGATTTCACCCTGACCATTAGCTCTCTGCAAC CGGAAGACTTTGCGACCTATTATTGCCAGCAGGG TCTGTTCCTGCCGTTCACCTTTGGCCAGGGCACG AAAGTTGAAATTAAACGTACG |
| | VH (DNA) | 130 | GAAGTGCAATTGCTGGAAAGCGGCGGTGGCCTGG TGCAGCCGGGTGGCAGCCTGCGTCTGAGCTGCGC GGCGTCCGGATTCACCTTTTCTTCTTACGCTATG TCTTGGGTGCGCCAGGCCCCGGGCAAAGGTCTCG AGTGGGTTTCCTTCATCTCTTCTGGTGGTTCTGA AACCTTCTATGCGGATAGCGTGAAAGGCCGCTTT ACCATCAGCCGCGATAATTCGAAAAACACCCTGT ATCTGCAAATGAACAGCCTGCGTGCGGAAGATAC GGCCGTGTATTATTGCGCGCGTGTTTCTTACATC TACTACTACTCTTGGGTTCTGTTCGATGTTTGGG GCCAAGGCACCCTGGTGACTGTTAGCTCA |

TABLE 1-continued

| MOR# | | SEQ ID NO: | [aa]/DNA |
|---|---|---|---|
| 12758 | HCDR1 | 131 | GYSFTDYWIS |
| | HCDR2 | 132 | WMGAIDPTDSYTRYSPSFQG |
| | HCDR3 | 133 | WYTSHPYYEGRYPMDV |
| | LCDR1 | 134 | TGTSSDVGHYNYVS |
| | LCDR2 | 135 | LMIYGVTKRPS |
| | LCDR3 | 136 | ASADEWPTLH |
| | VL | 137 | DIALTQPASVSGSPGQSITISCTGTSSDVGHYNY<br>VSWYQQHPGKAPKLMIYGVTKRPSGVSNRFSGSK<br>SGNTASLTISGLQAEDEADYYCASADEWPTLHVF<br>GGGTKLTVLGQ |
| | VH | 138 | EVQLVQSGAEVKKPGESLKISCKGSGYSFTDYWI<br>SWVRQMPGKGLEWMGAIDPTDSYTRYSPSFQGQV<br>TISADKSISTAYLQWSSLKASDTAMYYCARWYTS<br>HPYYEGRYPMDVWGQGTLVTVSS |
| | VL (DNA) | 139 | GATATCGCGCTGACCCAGCCGGCGAGCGTGAGCG<br>GTAGCCCGGGCCAGAGCATTACCATTAGCTGCAC<br>CGGCACCAGCAGCGATGTGGGCCATTACAACTAC<br>GTGTCTTGGTACCAGCAGCATCCGGGCAAGGCGC<br>CGAAACTGATGATCTACGGTGTTACTAAACGTCC<br>GAGCGGCGTGAGCAACCGTTTTAGCGGATCCAAA<br>AGCGGCAACACCGCGAGCCTGACCATTAGCGGCC<br>TGCAAGCGGAAGACGAAGCGGATTATTACTGCGC<br>TTCTGCTGACGAATGGCCGACTCTGCATGTGTTT<br>GGCGGCGGCACGAAGTTAACCGTTCTTGGCCAG |
| | VH (DNA) | 140 | GAAGTGCAATTGGTGCAGAGCGGTGCGGAAGTGA<br>AAAAACCGGGCGAAAGCCTGAAAATTAGCTGCAA<br>AGGCTCCGGATATAGCTTCACTGACTACTGGATC<br>TCTTGGGTGCGCCAGATGCCGGGCAAAGGTCTCG<br>AGTGGATGGGCGCTATCGACCCGACTGACAGCTA<br>CACCCGTTATAGCCCGAGCTTTCAGGGCCAGGTG<br>ACCATTAGCGCGGATAAAAGCATCAGCACCGCGT<br>ATCTGCAATGGAGCAGCCTGAAAGCGAGCGATAC<br>CGCGATGTATTATTGCGCGCGTTGGTACACTTCT<br>CATCCGTACTACGAAGGTCGTTACCCGATGGATG<br>TTTGGGGCCAAGGCACCCTGGTGACTGTTAGCTC<br>A |
| 12759 | HCDR1 | 141 | GYSFNNYWIA |
| | HCDR2 | 142 | WMGFIYPSNSATQYSPSFQG |
| | HCDR3 | 143 | DNEYSDSYFDV |
| | LCDR1 | 144 | RASQIVSSYLA |
| | LCDR2 | 145 | LLIYDASSRAT |
| | LCDR3 | 146 | QQSVNFPT |
| | VL | 147 | DIVLTQSPATLSLSPGERATLSCRASQIVSSYLA<br>WYQQKPGQAPRLLIYDASSRATGIPARFSGSGSG<br>TDFTLTISSLEPEDFAVYYCQQSVNFPTTFGQGT<br>KVEIKRT |
| | VH | 148 | EVQLVQSGAEVKKPGESLKISCKGSGYSFNNYWI<br>AWVRQMPGKGLEWMGFIYPSNSATQYSPSFQGQV<br>TISADKSISTAYLQWSSLKASDTAMYYCARDNEY<br>SDSYFDVWGQGTLVTVSS |
| | VL (DNA) | 149 | GATATCGTGCTGACCCAGAGCCCGGCGACCCTGA<br>GCCTGAGCCCGGGTGAACGTGCCACCCTGAGCTG<br>CAGAGCGAGCCAGATCGTTTCTTCTTACCTGGCT<br>TGGTACCAGCAGAAACCGGGCCAGGCCCCGCGTC<br>TATTAATCTACGACGCTTCTTCTCGTGCGACCGG<br>CATTCCGGCGCGTTTTAGCGGCAGCGGATCCGGC<br>ACCGATTTCACCCTGACCATTAGCAGCCTGGAAC<br>CGGAAGACTTTGCGGTGTATTATTGCCAGCAGTC<br>TGTTAACTTCCCGACTACCTTTGGCCAGGGCACG<br>AAAGTTGAAATTAAACGTACG |
| | VH (DNA) | 150 | GAAGTGCAATTGGTGCAGAGCGGTGCGGAAGTGA<br>AAAAACCGGGCGAAAGCCTGAAAATTAGCTGCAA<br>AGGCTCCGGATATAGCTTCAACAACTACTGGATC<br>GCTTGGGTGCGCCAGATGCCGGGCAAAGGTCTCG<br>AGTGGATGGGCTTCATCTACCCGTCTAACAGCGC<br>TACCCAGTATAGCCCGAGCTTTCAGGGCCAGGTG<br>ACCATTAGCGCGGATAAAAGCATCAGCACCGCGT<br>ATCTGCAATGGAGCAGCCTGAAAGCGAGCGATAC<br>CGCGATGTATTATTGCGCGCGTGACAACGAATAC<br>TCTGACTCTTACTTCGATGTTTGGGGCCAAGGCA<br>CCCTGGTGACTGTTAGCTCA |
| 12760 | HCDR1 | 151 | GYSFNNYWIA |
| | HCDR2 | 152 | WMGFIYPSNSATQYSPSFQG |
| | HCDR3 | 153 | DNEYSDSYFDV |
| | LCDR1 | 154 | RASQIVSSYLA |
| | LCDR2 | 155 | LLIYDASSRAT |

TABLE 1-continued

| MOR# | | SEQ ID NO: | [aa]/DNA |
|---|---|---|---|
| | LCDR3 | 156 | QQSVKSN |
| | VL | 157 | DIVLTQSPATLSLSPGERATLSCRASQIVSSYLA WYQQKPGQAPRLLIYDASSRATGIPARFSGSGSG TDFTLTISSLEPEDFATYYCQQSVKSNTFGQGTK VEIKRT |
| | VH | 158 | EVQLVQSGAEVKKPGESLKISCKGSGYSFNNYWI AWVRQMPGKGLEWMGFIYPSNSATQYSPSFQGQV TISADKSISTAYLQWSSLKASDTAMYYCARDNEY SDSYFDVWGQGTLVTVSS |
| | VL (DNA) | 159 | GATATCGTGCTGACCCAGAGCCCGGCGACCCTGA GCCTGAGCCCGGGTGAACGTGCCACCCTGAGCTG CAGAGCGAGCCAGATCGTTTCTTCTTACCTGGCT TGGTACCAGCAGAAACCGGGCCAGGCCCCGCGTC TATTAATCTACGACGCTTCTTCTCGTGCGACCGG CATTCCGGCGCGTTTTAGCGGCAGCGGATCCGGC ACCGATTTCACCCTGACCATTAGCAGCCTGGAAC CGGAAGACTTTGCGACCTATTATTGCCAGCAGTC TGTTAAATCTAACACCTTTGGCCAGGGCACGAAA GTTGAAATTAAACGTACG |
| | VH (DNA) | 160 | GAAGTGCAATTGGTGCAGAGCGGTGCGGAAGTGA AAAAACCGGGCGAAAGCCTGAAAATTAGCTGCAA AGGCTCCGGATATAGCTTCAACAACTACTGGATC GCTTGGGTGCGCCAGATGCCGGGCAAAGGTCTCG AGTGGATGGGCTTCATCTACCCGTCTAACAGCGC TACCCAGTATAGCCCGAGCTTTCAGGGCCAGGTG ACCATTAGCGCGGATAAAAGCATCAGCACCGCGT ATCTGCAATGGAGCAGCCTGAAAGCGAGCGATAC CGCGATGTATTATTGCGCGCGTGACAACGAATAC TCTGACTCTTACTTCGATGTTTGGGGCCAAGGCA CCCTGGTGACTGTTAGCTCA |
| 12761 | HCDR1 | 161 | GYSFNNYWIA |
| | HCDR2 | 162 | WMGFIYPSNSATQYSPSFQG |
| | HCDR3 | 163 | DNEYSDSYFDV |
| | LCDR1 | 164 | RASQIVSSYLA |
| | LCDR2 | 165 | LLIYDASSRAT |
| | LCDR3 | 166 | QQSNGWLP |
| | VL | 167 | DIVLTQSPATLSLSPGERATLSCRASQIVSSYLA WYQQKPGQAPRLLIYDASSRATGIPARFSGSGSG TDFTLTISSLEPEDFATYYCQQSNGWLPTFGQGT KVEIKRT |
| | VH | 168 | EVQLVQSGAEVKKPGESLKISCKGSGYSFNNYWI AWVRQMPGKGLEWMGFIYPSNSATQYSPSFQGQV TISADKSISTAYLQWSSLKASDTAMYYCARDNEY SDSYFDVWGQGTLVTVSS |
| | VL (DNA) | 169 | GATATCGTGCTGACCCAGAGCCCGGCGACCCTGA GCCTGAGCCCGGGTGAACGTGCCACCCTGAGCTG CAGAGCGAGCCAGATCGTTTCTTCTTACCTGGCT TGGTACCAGCAGAAACCGGGCCAGGCCCCGCGTC TATTAATCTACGACGCTTCTTCTCGTGCGACCGG CATTCCGGCGCGTTTTAGCGGCAGCGGATCCGGC ACCGATTTCACCCTGACCATTAGCAGCCTGGAAC CGGAAGACTTTGCGACCTATTATTGCCAGCAGTC TAACGGTTGGCTGCCGACCTTTGGCCAGGGCACG AAAGTTGAAATTAAACGTACG |
| | VH (DNA) | 170 | GAAGTGCAATTGGTGCAGAGCGGTGCGGAAGTGA AAAAACCGGGCGAAAGCCTGAAAATTAGCTGCAA AGGCTCCGGATATAGCTTCAACAACTACTGGATC GCTTGGGTGCGCCAGATGCCGGGCAAAGGTCTCG AGTGGATGGGTTTCATCTACCCGTCTAACAGCGC TACCCAGTATAGCCCGAGCTTTCAGGGCCAGGTG ACCATTAGCGCGGATAAAAGCATCAGCACCGCGT ATCTGCAATGGAGCAGCCTGAAAGCGAGCGATAC CGCGATGTATTATTGCGCGCGTGACAACGAATAC TCTGACTCTTACTTCGATGTTTGGGGCCAAGGCA CCCTGGTGACTGTTAGCTCA |
| 12762 | HCDR1 | 171 | GYSFNNYWIA |
| | HCDR2 | 172 | WMGFIYPSNSATQYSPSFQG |
| | HCDR3 | 173 | DNEYSDSYFDV |
| | LCDR1 | 174 | RASQIVSSYLA |
| | LCDR2 | 175 | LLIYDASSRAT |
| | LCDR3 | 176 | QQSEQVPT |
| | VL | 177 | DIVLTQSPATLSLSPGERATLSCRASQIVSSYLA WYQQKPGQAPRLLIYDASSRATGIPARFSGSGSG TDFTLTISSLEPEDFAVYYCQQSEQVPTTFGQGT KVEIKRT |

TABLE 1-continued

| MOR# | SEQ ID NO: | [aa]/DNA |
|---|---|---|
| VH | 178 | EVQLVQSGAEVKKPGESLKISCKGSGYSFNNYWI<br>AWVRQMPGKGLEWMGFIYPSNSATQYSPSFQGQV<br>TISADKSISTAYLQWSSLKASDTAMYYCARDNEY<br>SDSYFDVWGQGTLVTVSS |
| VL (DNA) | 179 | GATATCGTGCTGACCCAGAGCCCGGCGACCCTGA<br>GCCTGAGCCCGGGTGAACGTGCCACCCTGAGCTG<br>CAGAGCGAGCCAGATCGTTTCTTCTTACCTGGCT<br>TGGTACCAGCAGAAACCGGGCCAGGCCCCGCGTC<br>TATTAATCTACGACGCTTCTTCTCGTGCGACCGG<br>CATTCCGGCGCGTTTTAGCGGCAGCGGATCCGGC<br>ACCGATTTCACCCTGACCATTAGCAGCCTGGAAC<br>CGGAAGACTTTGCGGTGTATTATTGCCAGCAGTC<br>TGAACAGGTTCCGACTACCTTTGGCCAGGGCACG<br>AAAGTTGAAATTAAACGTACG |
| VH (DNA) | 180 | GAAGTGCAATTGGTGCAGAGCGGTGCGGAAGTGA<br>AAAAACCGGGCGAAAGCCTGAAAATTAGCTGCAA<br>AGGCTCCGGATATAGCTTCAACAACTACTGGATC<br>GCTTGGGTGCGCCAGATGCCGGGCAAAGGTCTCG<br>AGTGGATGGGCTTCATCTACCCGTCTAACAGCGC<br>TACCCAGTATAGCCCGAGCTTTCAGGGCCAGGTG<br>ACCATTAGCGCGGATAAAAGCATCAGCACCGCGT<br>ATCTGCAATGGAGCAGCCTGAAAGCGAGCGATAC<br>CGCGATGTATTATTGCGCGCGTGACAACGAATAC<br>TCTGACTCTTACTTCGATGTTTGGGGCCAAGGCA<br>CCCTGGTGACTGTTAGCTCA |

Example 1: Mouse IL17C

Mouse IL17C was purchased from R&D Systems (#2306-ML/CF; R&D Systems, Inc., Minneapolis, USA). Biotinylated mouse IL17C was prepared using the ECL™ biotinylation module (GE Healthcare; #1061918). After biotinlyation the product was purified using Zeba™ Desalt spin columns (Pierce; #89889).

Quality control of the biotinylated IL17C was performed using dynamic light scattering (DLS), size exclusion chromatography (SEC) and SDS-PAGE. As expected, SDS-PAGE revealed an apparent molecular weight of about 22 kDa under reducing conditions and of about 40 kDa under non-reducing conditions. In addition no high molecular weight species or aggregates could be detected. The predicted size of the antigen was confirmed in SEC, where biotinylated mouse IL17C was visible as one peak with a molecular weight of about 43 kDa. In DLS, no aggregates could be detected. Additionally it was confirmed that mouse IL17C was biotinylated quantitatively.

Only material that passed the quality control was used for panning and binding assays.

Example 2: Mouse IL17 Receptor E

The extracellular domain (ECD) of mouse IL-17 receptor E (GeneID: 57890, isoform 1) was cloned as a C-terminal Fc fusion protein (referred to as "IL17RE/Fc"). A construct containing a VK-Leader followed by the ECD of mouse IL17C was transiently expressed in HKB11 cells (Cho et al. (2002) J. Biomed Sci. November-December; 9(6 Pt 2):631-8). The products were purified via protein A affinity chromatography. Purity was analyzed under denaturing, reducing and denaturing, non-reducing conditions in SDS-PAGE and in native state by High Pressure-SEC and DLS.

Example 3: IL17C-IL17 Receptor E Interaction Assay

To test binding of mouse IL17 to its putative receptor, IL17 receptor E an interaction assay was set up. The assay setup is depicted in FIG. 1A. In brief, IL17 receptors B and E were coated on a Multi-array® 384-well plate Standard plate (Meso Scale Discovery; #L21XA-4) and biotinylated mouse IL17C was added. Binding of mouse IL17C to its receptor was measured via binding of Streptavidin in a MSD Sector Imager 6000 (Meso Scale Discovery, Gaithersburg, Md., USA).

Figure 1B:
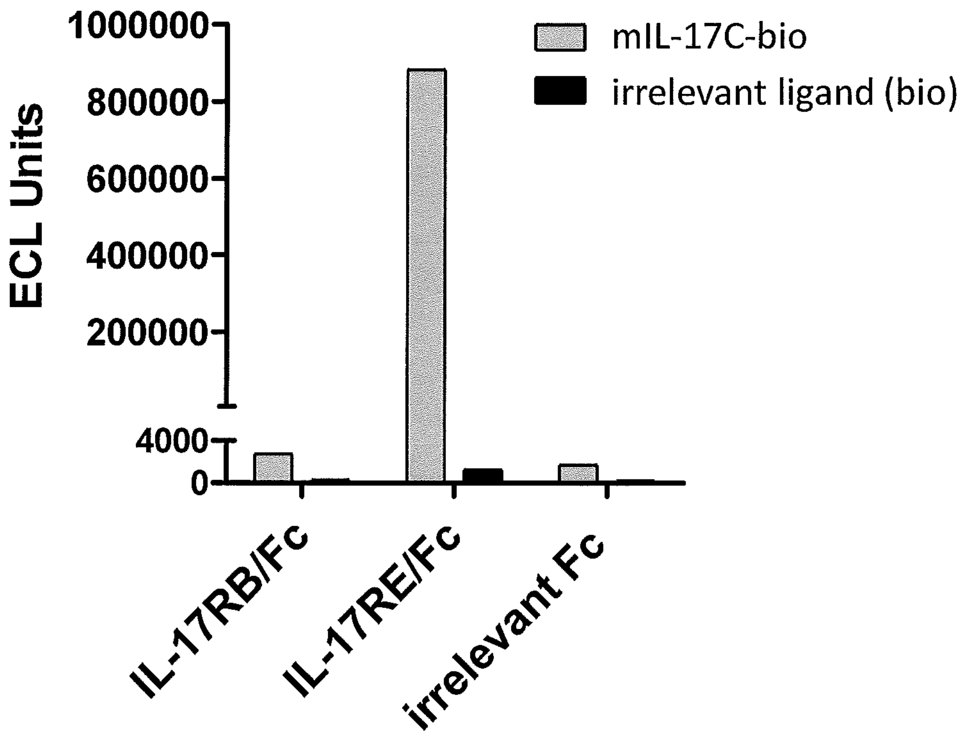
FIG. 1B shows results of the receptor interaction assay shown in FIG. 1A. IL17C was clearly found to bind to mouse IL17RE/Fc, but not to mouse IL-17RB or another irrelevant receptor.

Results are shown in FIG. 1B. IL17C was clearly found to bind to mouse IL17RE/Fc, but not to mouse IL-17RB or another irrelevant receptor. Also, an irrelevant biotinylated ligand did not show binding to any of the three receptors tested. The interaction assay is therefore highly specific and well suited for the analysis of IL17C-IL17 receptor E interactions.

Example 4: Effect of Prior Art Antibodies on the IL17C-IL17 Receptor E Interaction Three prior art antibodies were tested for their ability to inhibit binding of mouse IL17C to mouse IL17RE/Fc in the interaction assay of Example 3. The following antibodies were tested:

A: rat $IgG_{2A}$ monoclonal anti-mouse IL17C antibody (R&D Systems; clone 311522, #MAB23061)

B: rat $IgG_{2A}$ monoclonal anti-mouse IL17C antibody (R&D Systems; clone 311523, # MAB2306)

C: rat anti-mouse IL17C (US Biological; clone: 8B28, #I8439-20R3)

Antibodies were pre-incubated with biotinylated mouse IL17C and the pre-formed complex was then added to the coated mouse IL17RE/Fc.

Figure 1C:
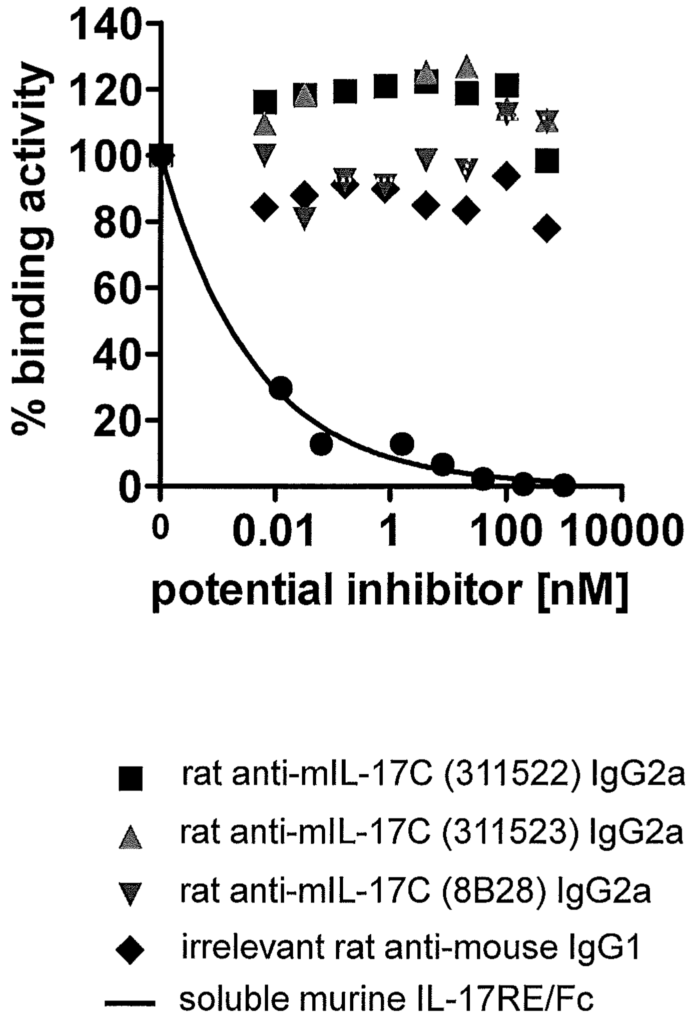
FIG. 1C shows results of the receptor interaction assay shown in FIG. 1A. None of the three prior art antibodies inhibits binding of mouse IL17C to mouse IL17RE/Fc.

Results are shown in FIG. 1C. None of the prior art anti-mouse IL17C antibodies did show any effect on the binding of mouse IL17C to its receptor IL17RE/Fc.

Example 5: Panning Strategy

The HuCAL PLATINUM® library was used to select specific Fab fragments against mouse IL17C. This phagemid library is based on the HuCAL® concept disclosed in Knappik et al. (Knappik et al. (2000) J. Mol. Biol. 296:57-

86) and employs the CysDisplay® technology for displaying the Fab on the phage surface (Lohning et al., WO2001/05950).

Different panning strategies were performed, solution panning, including various maturation strategies, as well as conventional solid phase panning. For solid phase panning mouse IL17C was directly coated on Maxisorp™ Immuno plates (Nunc; #442404). A total of three rounds of panning were performed for solid phase panning. Three selection rounds were performed with a successive increase of washing stringency and reduction of antigen concentration from round to round. For solution panning biotinylated antigen was exposed to the phage library in solution with subsequent capture of phage-antigen complexes on streptavidin beads. Again, three selection rounds were performed with a successive increase of washing stringency and reduction of antigen concentration from round to round. Phages were isolated using streptavidin-coupled magnetic beads (Invitrogen, #112-05D). To select high affinity antibodies, HCDR2 and LCDR3 libraries were generated after the second round of selection (average library size ~$1\times10^8$) followed by two more selection rounds with further increased stringency and further decreased antigen concentrations.

Example 6: Initial Characterization of Panning Output Via ELISA

To facilitate rapid expression of soluble Fab fragments in crude bacterial lysates periplasmatic extracts were prepared as previously described (Rauchenberger et al. (2003) J. Biol. Chem. 278.40: 38194-205). Fab containing *E. coli* lysates were used for ELISA screening of the initial hits.

Specificity of the binders were investigates via ELISA screening on the directly coated antigen or on the biotinylated antigen. For ELISA screening on the directly coated antigen Maxisorp™ 384 well plates (Nunc; #460518) were coated with 2.5 μg/mL mouse IL17C in PBS. After blocking of plates with 5% skimmed milk powder in PBS, Fab-containing *E. coli* lysates were added. Binding of Fabs was detected by $F(ab)_2$ specific goat anti-human IgG conjugated to alkaline phosphatase (diluted 1:5000) using Attophos fluorescence substrate (Roche: #11681982001). Fluorescence emission at 535 nm was recorded with excitation at 430 nm. For ELISA screening on biotinylated antigen Maxisorp™ 384 well plates were coated with Fd fragment specific sheep anti-human IgG (Binding site, #PC075) diluted 1:1000 in PBS. After blocking with 5% skim milk powder in PBS, Fab-containing *E. coli* lysates were added. Subsequently the captured HuCAL®-Fab fragments were allowed to bind to 1 μg/ml biotinylated mouse IL17C, which was detected by incubation with streptavidin conjugated to alkaline phosphatase followed by addition of AttoPhos fluorescence substrate (Roche: #11681982001). Fluorescence emission at 535 nm was recorded with excitation at 430 nm. Almost 9000 Fab fragments isolated from the panning procedure were tested in these ELISA assays, and about 2900 were positive in all ELISA tests.

Example 7: Characterization of the Binders Via the IL17C-IL17 Receptor E Interaction Assay To test Fab-containing crude bacterial lysates for neutralizing activity in high throughput screening mode a slightly modified assay as outlined in Example 3 was used. Maxisorp™ 384 well MSD plates (Nunc; #460518) were coated with 30 μL mouse IL17RE/Fc at 0.6 μg/mL in PBS overnight at 4° C. The next day 20 μL Fab-containing *E. coli* lysates were pre-incubated for 30 min at RT with an equal volume of biotinylated mouse IL17C at 2 nM. After blocking of plates for 1 h with 5% BSA in PBS, preformed antibody-ligand complexes were added for 1 h to coated IL17RE/Fc and receptor binding was detected via Streptavidin-ECL using MSD Sector Imager 6000 (Meso Scale Discovery, Gaithersburg, Md., USA).

To determine inhibitory activity of purified anti-IL17C human-mouse chimeric IgG2a in a mIL-17 RE interaction assay, Maxisorp™ 384 well MSD plates were coated with 30 μL mouse IL17RE/Fc at 75 ng/mL in PBS at 4° C. overnight. The next day 25 μL of a serial antibody dilution (concentrations from 0.001 to 100 nM) were pre-incubated for 30 min at RT with an equal volume of biotinylated mouse IL17C at 0.125 nM. After blocking of plates for 1 h with 2.5% BSA in PBST, preformed antibody-ligand complexes were added for 1 h to coated IL17RE/Fc and receptor binding was detected via Streptavidin-ECL using MSD Sector Imager.

Of all ELISA-positive binders, the IL17C-IL17 receptor E interaction assay, followed by sequencing of the positive clones, revealed merely 141 sequence-unique clones belonging to 33 different HCDR3 families. This number was again reduced by confirmatory screening in ELISA and mouse IL17RE/Fc inhibition assay. To select candidates with best inhibitory activity, BEL lysates were pre-diluted up to 1:500 for use in IL17RE/Fc inhibition assay. Finally, 18 sequence-unique clones belonging to 8 different HCDR3 families could be identified which consistently and repeatedly were positive in the IL17C-IL17 receptor E interaction assay.

Example 8: Polyclonal IgG Conversion

Conversion of the Fab fragments into an IgG format was performed by polyclonal cloning of the Fab fragments into the desired IgG format. A human-mouse chimeric IgG format was used to avoid immunogenicity reactions directed against administered anti-mouse IL17C antibodies in the in vivo proof of concept study with wild-type mice. Two different constant regions were used—the IgG2a and the IgG1 isotype. Potential N-linked glycosylation sites were removed via site-directed mutagenesis using the QuickChange II Site-directed Mutagenesis Kit (Stratagene; #0200524). The sequence diversity of all IgG's recovered from this procedure is depicted in Table 1.

Example 9: Exploratory Scale Production of IgG's

All IgGs recovered from the procedure described in Example 8 were produced in exploratory-scale in HKB11 cells (Cho et al. (2002) J. Biomed Sci. November-December; 9(6 Pt 2):631-8) in both chimeric human/mouse IgG2a and chimeric human/mouse IgG1 isotype format, in order to assess production yields and monomeric portion of the antibodies with two different constant regions. The highest quantities could be produced with antibodies of the chimeric human/mouse IgG2a format. This format also successfully passed quality control in SEC (>90% monomer content). The chimeric human/mouse IgG2a format was therefore chosen for further functional testing. Purification yield and the portion of monomer as determined in SEC is shown in FIG. 2.

Example 10: Affinity Determination

All purified chimeric human-mouse chimeric IgG2a antibodies were titrated on mouse IL17C for $EC_{50}$ determination in ELISA starting with a concentration of 100 nM. $EC_{50}$ values on mouse IL17C were determined in 1 to 3 independent experiments. Results are shown in FIG. 3.

$EC_{50}$ values ranged between 200 and 1200 pM, with most $EC_{50}$ values were around 300 pM. Binding activity of 4 IgGs (MOR12755, MOR12756, 12757, 12758) could not be confirmed with purified IgG2a, therefore these IgGs were excluded from further characterization. None of the antibodies showed cross-reactivity to human IL17C (sequence identity 77%), to mouse IL-17B (sequence identity 30%) or to the negative control antigen lysozyme.

Monovalent affinities of anti-IL17C antibodies were determined by solution equilibrium titration (SET) using Fab fragments. Affinity determination in solution was basically performed as described in the literature (Friquet et al., (1985) J. Immunol. Meth. 77: 305-19). In order to improve the sensitivity and accuracy of the SET method, it was transferred from classical ELISA to ECL based technology (Haenel et al. (2005) Anal Biochem. 339.1: 182-84). Binders were expressed and purified in Fab_FH format. Some Fabs did either not bind or showed no sigmoidal binding curve in SET, therefore affinities could only be determined for 10 candidates. Monovalent affinities ranged between 48 and 4100 pM with most $K_D$ values of the Fabs in the low pM range (≤100 pMError! Reference source not found.). Results are shown in FIG. 4.

Example 11: IL17C-IL17 Receptor E Interaction Assay in with Binders in IgG Format To characterize the antibodies in human/mouse IgG2a format in more detail, for each candidate $IC_{50}$ values were determined in the IL-17 receptor E inhibition assay as described herein above in up to 4 independent experiments.

Results are depicted in FIG. 5. 11 out of the 12 IgGs showed inhibitory activity with mean $IC_{50}$ values ranging between 9 and 8442 pM. 9 out of these 11 inhibitory IgGs even had $IC_{50}$ values in the low picomolar range. The best candidates belonged to different HCDR3 families and were of different VL subtypes (kappa or lambda).

Example 12: Stability in Mouse Serum

In order to analyse whether the selected anti-mouse IL17C antibodies are suitable for in vivo administration in mice, stability in mouse serum was determined for a subset of 11 purified IgGs that showed acceptable production yields and specific binding to mouse IL17C (see hereinabove).

96 well Maxisorp plates (Nunc; #442404) were coated with avidin at a concentration of 1 μg/ml in PBS overnight at 4° C. The next day, anti-IL17 chimeric IgG2a were incubated in mouse serum for 24 h at 37° C. at a final concentration 100 μg/mL. After the incubation step the antibodies were diluted 1:100 in LowCross buffer (Candor Bioscience; #100500). As a reference the same set of antibodies were freshly diluted in LowCross buffer+1% mouse serum and incubated for 30 min at RT. Avidin coated plates were incubated with blocking buffer (Superblock blocking buffer from Pierce, #37515) and subsequently 100 μL of 0.1 μg/mL biotin-IL17C in LowCross buffer was added to blocked wells. After a washing step a serial dilution of the serum-incubated and freshly diluted IgGs was added. Binding of IgGs was detected by anti-mouse-IgG2a POD conjugated detection antibody (diluted 1:5000 in LowCross buffer) using TMB One Component HRP as substrate. The reaction was stopped by adding 1M HCl and absorbance was measured at 450 nm.

With exception of one IgG candidate (MOR12760) which exhibited only moderate serum stability, all other antibodies showed a very good stability in mouse serum (coefficient of variation ≤20%) after incubation for 24 h at 37° C. Results are depicted in FIG. 6.

Example 13: Selection of the Binders for the In Vivo Proof of Concept Study

Based on their favorable properties with respect to productivity, stability, binding and functional activity in IL-17RE receptor inhibition assay and in a cell-based NFkB reporter gene assay, MOR12743 and MOR12762 were selected as candidates for the in vivo proof of concept study.

Example 14: In Vivo CIA Model 14.1 Materials

Completed Freund's adjuvant (CFA) and incomplete Freund's adjuvant (IFA) were purchased from Difco (MI, US). Bovine collagen type II (CII), lipopolysaccharide (LPS), and Enbrel was obtained from MD Biosciences (Germany); Sigma (P4252, L'Isle d'Abeau, France), Whyett (25 mg injectable syringe, France), respectively. All other reagents used were of reagent grade and all solvents were of analytical grade.

14.2 Animals

DBA1/J mice (male, 6-7 weeks old, approx 20 gram) were obtained from Centre d'Elevage Regional Janvier (Laval, France). Mice were kept on a 12 hr light/dark cycle (0700-1900). Temperature was maintained at 22° C., and food and water were provided ad libitum.

14.3 Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.1 mL of the emulsion was injected intradermally at the base of the tail of each mouse on day 1, a second booster intradermal injection (CII solution at 2 mg/mL in CFA 0.1 mLemulsion) was performed on day 21. This immunization method was modified from published methods (Brand et al, 2007, Collagen-induced arthritis. Nature Protocols; vol 2 (5): 1269-1275; Lin et al., 2007, Anti-rheumatic activities of histone deacetylase (HDAC) inhibitors in vivo in collagen-induced arthritis in rodents. Br J Pharmacol. April; 150 (7):829-31).

14.4 Study Design 14.4.1 Therapeutic Protocol

The therapeutic effects of the antibodies were tested in the mouse CIA model. Mice were randomly divided into equal groups and each group contained 10 mice. All mice were immunized on day 1 and boosted on day 21. Therapeutic dosing lasted from day 31 to day 46. The negative control group was treated with vehicle (PBS) and the positive control group with Enbrel (10 mg/kg, 3× week, i.p.). An antibody of interest was tested at 10 mg/kg, i.p. 3 times per week.

Therefore, five different treatment groups were used, wherein each group consisted of ten mice.

Group 1: Vehicle (PBS)
Group 2: Enbrel 10 mg/kg/3× week, i.p.
Group 3: MOR03207 10 mg/kg/3× week, i.p.
Group 4: MOR12743 10 mg/kg/3× week, i.p.
Group 5: MOR12762 10 mg/kg/3× week, i.p.

Anti-IL17C antibodies were administered i.p. three times a week at 10 mg/kg. Blood samples (approx 250 μL) were taken on days 31 and 46 for pharmacokinetic analysis.

14.4.2 Preventative Protocol

The preventative effects of the antibodies were tested in the mouse CIA model. Mice were randomly divided into two equal groups containing 20 mice. All mice were immunized on day 1 and boosted on day 21. Prophylactic dosing lasted from day 21 to day 46. The negative control group was treated with negative antibody (MOR03207, 10 mg/kg, 3× week, i.p.) An antibody of interest (MOR12762) was tested at 10 mg/kg, 3× week, i.p.

Therefore, two different treatment groups were used, wherein each group consisted of twenty mice.

Group 1: MOR03207 10 mg/kg/3× week, i.p.

Group 2: MOR12762 10 mg/kg/3× week, i.p.

Anti-IL17C antibodies were administered i.p.three times a week at 10 mg/kg. Blood sample (approx 250 μL) were taken on days 21, 36 and 46 for pharmacokinetic analysis.

14.5 Clinical Assessment of Arthritis

Arthritis was scored according to the method of Khachigian 2006 (Collagen antibody-induced arthritis. (2006) Nature Protocols 1, 2512-6), Lin et al 2007 (supra); Nishida et al. 2004 (Histone deacetylase inhibitor suppression of autoantibody-mediated arthritis in mice via regulation of p16INK4a and p21(WAF1/Cip1) expression. Arthritis Rheum. 10: 3365-76); and Brand et al. 2007 (supra). The swelling of each of the four paws was ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al., 2004 (supra)).

If required, to permit the meta-analysis of multiple therapeutic studies the clinical score values may be normalised as follows:

AUC of Clinical Score (AUC Score):

The area under the curve (AUC) from day 31(21) to day 46 was calculated for each individual animal. The AUC of each animal was divided by the average AUC obtained for the vehicle in the study from which the data on that animal was obtained and multiplied by 100 (i.e. the AUC was expressed as a percentage of the average vehicle AUC per study).

Clinical Score Increase from Day 21 to Day 46 (End Point Score):

The clinical score difference for each animal was divided by the average clinical score difference obtained for the vehicle in the study from which the data on that animal was obtained and multiplied by 100 (i.e. the difference was expressed as a percentage of the average clinical score difference for the vehicle per study).

14.6 Radiology (Larsen's Score)

X-ray photos were taken of the hind paws of each individual animal. A random blind identity number was assigned to each of the photos, and the severity of bone erosion was ranked by three independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from Salvemini et al., 2001 (Amelioration of joint disease in a rat model of collagen-induced arthritis by M40403, a superoxide dismutase mimetic. Arthritis Rheum. 44:2909-21); Bush et al., 2002 (Reduction of joint inflammation and bone erosion in rat adjuvant arthritis by treatment with interleukin-17 receptor IgG1 Fc fusion protein. Arthritis Rheum. 46: 802-5); Sims et al., 2004, (Targeting osteoclasts with zoledronic acid prevents bone destruction in collagen-induced arthritis. Arthritis Rheum., 50: 2338-46) and Jou et al., 2005 (Thrombospondin 1 as an effective gene therapeutic strategy in collagen-induced arthritis. Arthritis Rheum. 52:339-44).

14.7 Results

Figure 7:
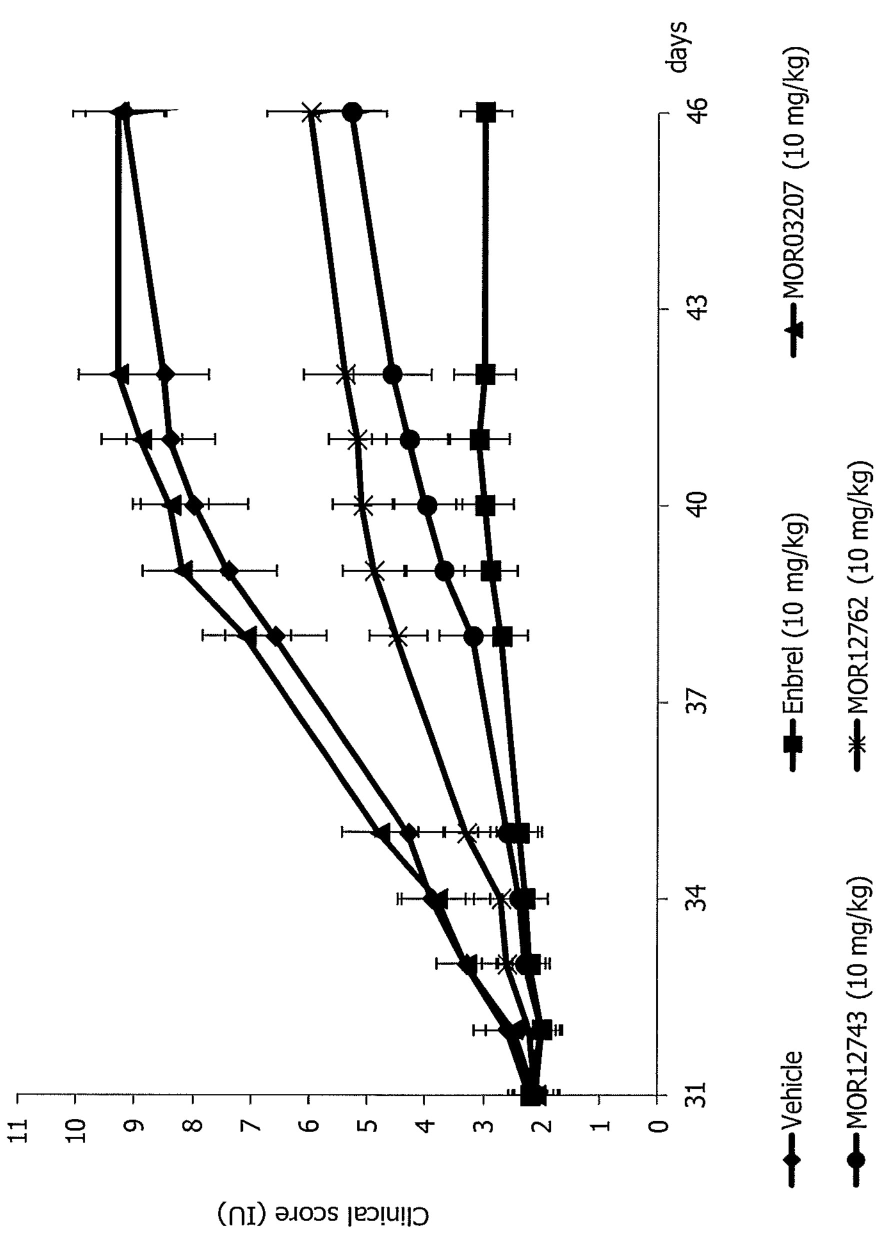
FIG. 7 shows the results of MOR12743 and MOR12762 administration on the clinical score in the treatment protocol of the mouse CIA model compared to vehicle, Enbrel® (etanercept) and a control antibody (MOR03207).
Figure 8:
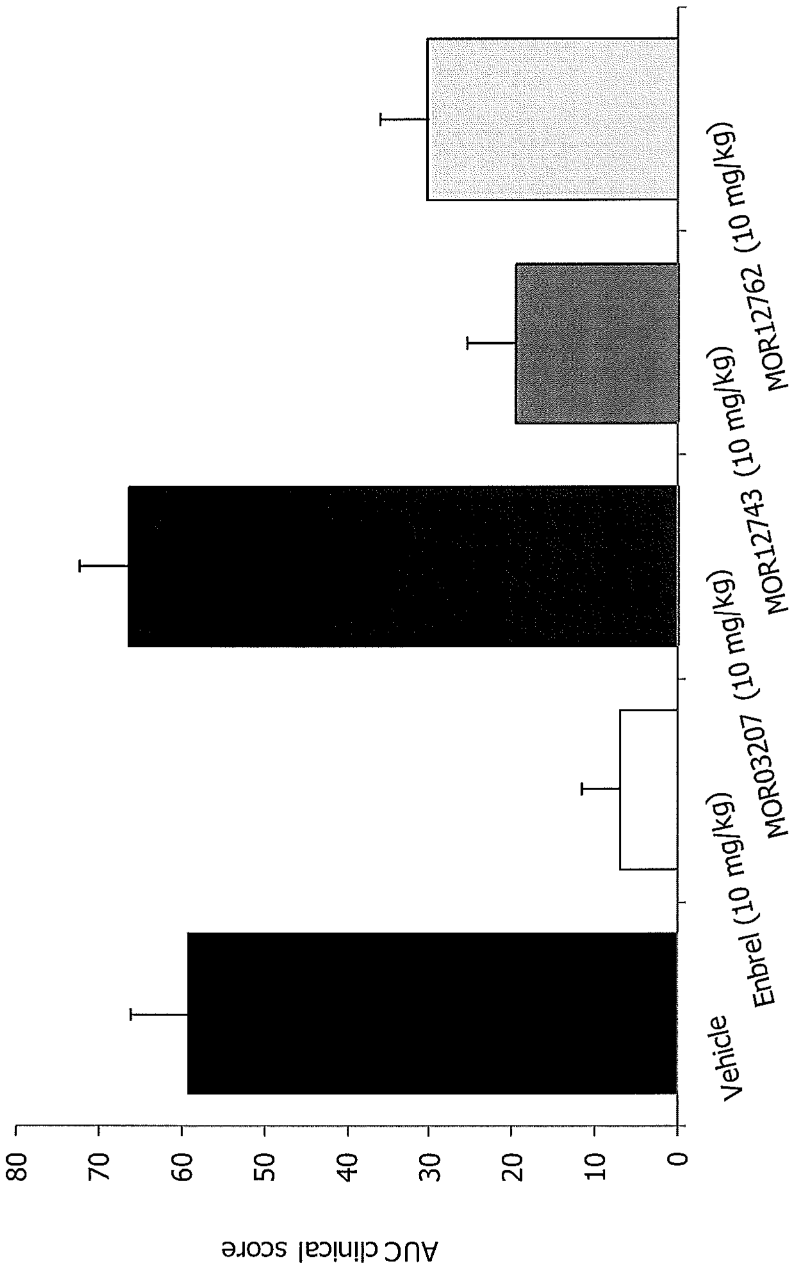
FIG. 8 shows the results of MOR12743 and MOR12762 administration on the AUC of the clinical score in the treatment protocol of the mouse CIA model compared to vehicle, Enbrel® (etanercept) and a control antibody (MOR03207).

In the treatment model, treatment was assessed via the clinical score and the Larsen score. Results are depicted in FIG. 7 and FIG. 8. Strikingly, both anti-IL17C antibodies tested (MOR12743 and MOR12762) demonstrated a significant inhibition of inflammation. The negative control antibody, MOR03207, did not inhibit inflammation, whereas the positive control, Enbrel, did inhibit disease progression.

Figure 9:
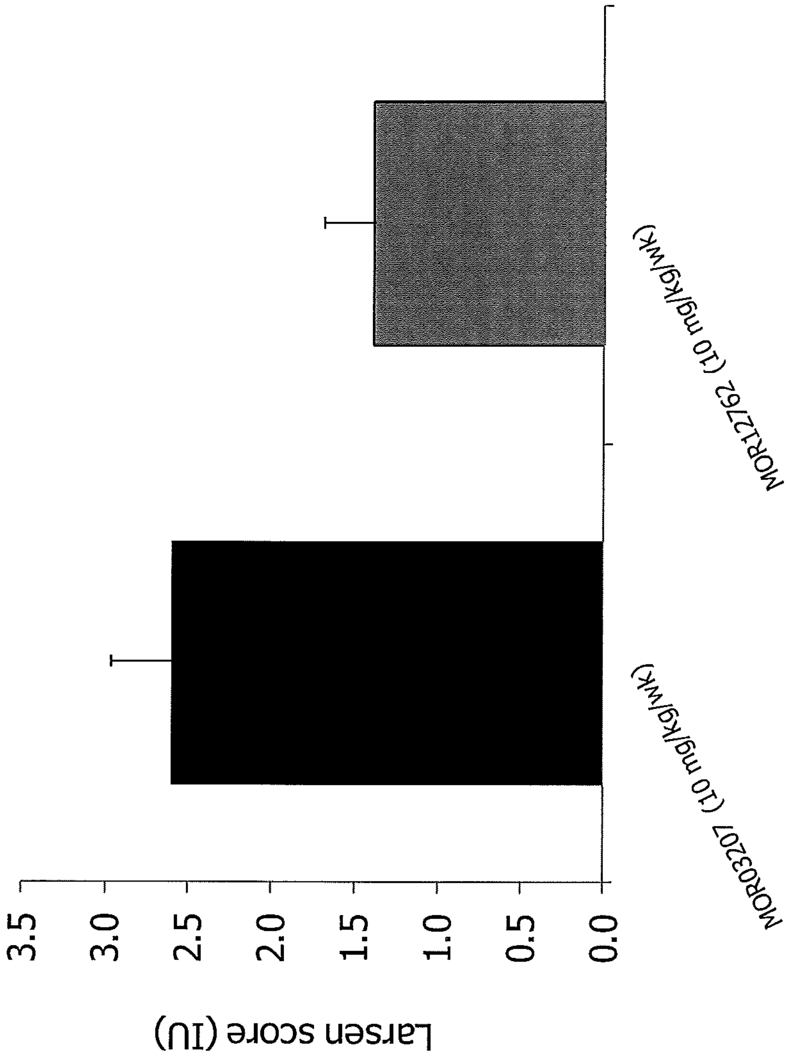
FIG. 9 shows the results of MOR12762 administration on the Larsen score in the prophylaxis protocol of the mouse CIA model compared to a control antibody (MOR03207).

In the preventative model, treatment was assessed via the clinical score and the Larsen score. Results are depicted in FIG. 9. Strikingly, the anti-IL17C antibody tested (MOR12762) demonstrated a significant inhibition of inflammation and bone degradation. The negative control antibody, MOR03207, did not inhibit neither inflammation nor bone erosion.

14.8 Steady State PK

At pre-dose, days 31 and 46 (treatment protocol) or days 21, 36 and 46 (preventive protocol), blood samples were collected at the retro-orbital sinus with lithium heparin as anti-coagulant. Whole blood samples were centrifuged and the resulting plasma samples were stored at −20° C. pending analysis.

Example 15—Tobacco Smoke Model

Daily exposures of mice (C57BL/6J, Charles River) to tobacco smoke (TS) for 11 consecutive days resulted in pulmonary inflammation, as indicated by an increase in the total number of cells recovered in the bronchoalveolar lavage (BAL), when compared with a similarly treated air-exposed group, 24 h after the final exposure. The response consisted of significant increases in the numbers of macrophages, epithelial cells, neutrophils and lymphocytes recovered in BAL.

MOR12743 was administered by the intra-peritoneal route (i.p.), 1 h prior to TS-exposure on days 1, 4, 7 and 10 of exposure. This resulted in significant inhibition of the total number of cells recovered in the BAL and specifically the numbers of epithelial cells and neutrophils.

MOR03207 was administered by the intra-peritoneal route (i.p.), 1 h prior to TS-exposure on days 1, 4, 7 and 10 of exposure. This did not result in any significant inhibition of total cell numbers or the numbers of any specifically identified cell types recovered in the BAL.

Roflumilast (ChemPharmaServe Ltd. Ref. 0010206) was administered 5 mg/kg orally (p.o.), 1 h prior to each TS-exposure. This significantly inhibited the total number of cells recovered in the BAL and specifically the numbers of epithelial cells neutrophils and lymphocytes.

All TS-exposed groups showed some bodyweight loss but this was not significant when compared with the air-exposed group at sacrifice on day 12.

15.1 Materials

Vehicle for i.p. administration: D-PBS pH7.4 (PAA Product Ref. H15-002, Lot. H00208-2353)

Vehicle for p.o. administration: PEG 200/water for injection (60%/40% v/v)

Phosphate buffered saline (PBS), for the bronchoalveolar lavage (BAL), was obtained from Gibco. Euthatal (sodium pentobarbitone) was obtained from Merial Animal Health Ltd. The tobacco smoke was generated using 'Marlboro 100' cigarettes purchased from a commercial supplier.

Formulations:

MOR12743 and MOR03207 were frozen, at 1 mg/mL. Both test substances were allowed to thaw at 4° C. overnight prior to administration.

Roflumilast was formulated by placing a pre-weighed amount in a mortar and grinding gently while adding vehicle (PEG200/water, 60%/40% v/v) drop-wise to form a suspension. Suspensions were vortex-mixed prior to administration.

15.2 Methods

Previous studies have established that the total numbers of cells recovered in the BAL are significantly elevated 24 h following the last of 11 daily TS-exposures. In this study, a time point of 24 h after the final air or TS-exposure was used for analysis.

Vehicle (PBS), MOR12743 and MOR03207 were administered i.p., 1 h prior to TS-exposure on days 1, 4, 7 and 10 of the study. Roflumilast was administered p.o., 1 h prior to each TS-exposure.

15.2.1 Exposure of Animals to TS Daily for 11 Consecutive Days

In this exposure protocol, mice were exposed in groups of 5 in clear polycarbonate chambers (27 cm×16 cm×12 cm). The TS from 'Marlboro 100' cigarettes was allowed to enter the exposure chambers at a flow rate of 100 mL/min. In order to minimise any potential problems caused by repeated exposure to a high level of TS, the exposure period to TS was increased initially from 25 minutes at the start of the study (day 1) to a maximum of 45 minutes on day 3. The exposure schedule used in this study was as follows:

Day 1: 25 min exposure (~5 cigarettes).

Day 2: 35 min exposure (~7 cigarettes).

Days 3-11: 45 min exposure (~9 cigarettes).

Exposure boxes were vented after 10 min and every 5 min thereafter.

One further group of mice was exposed to air on a daily basis for equivalent lengths of time as sham controls (no TS-exposure).

15.2.2 Bronchoalveolar Lavage and Cytospin Analysis

Bronchoalveolar Lavage was Performed as Follows:

The trachea was cannulated using a 10 mm long Luer fitting stainless steel cannula. Phosphate buffered saline (PBS) was used as the lavage fluid. A volume of 0.4 mL was gently instilled and withdrawn 3 times using a 1 mL syringe and then placed in an Eppendorf tube and kept on ice prior to subsequent determinations.

Total Cell-Counts were Performed as Follows:

Lavage fluid was separated from cells by centrifugation (6 min at 3400 rpm, RCF=3070×g—'Eppendorf Mini Spin') and the supernatant decanted and frozen for possible subsequent analysis. The cell pellet was re-suspended in a known volume of PBS and total cell numbers calculated by counting a stained (Turks stain) aliquot under a microscope using a haemocytometer.

Differential Cell-Counts were Performed as Follows:

The residual cell pellet was diluted to approximately 105 cells per mL. A volume of 500 μl was placed in the funnel of a cytospin slide and centrifuged for 8 min at 800 rpm, RCF=72.26×g (Shandon Cytospin 3). The slide was air-dried and stained using Wrights/Giemsa stain as per the proprietary instructions. When dried and cover-slipped, differential cell-counts were performed using light microscopy. Approximately 400 cells were counted for each slide. Cells were identified using standard morphometric techniques.

15.3 Treatment Regimes

In this study, 4 groups of mice were subjected to daily TS-exposure for 11 days and were sacrificed on the $12^{th}$ day, 24 h after the final TS-exposure. Three groups received either vehicle (D-PBS), MOR12743 or MOR03207, i.p., 1 h prior to TS-exposure on days 1, 4, 7 and 10 of the study. One group received Roflumilast, p.o., 1 h prior to each TS-exposure. A further group was exposed to air for 11 consecutive days and sacrificed on the 12th day, 24 h after the final air-exposure. This group received vehicle (D-PBS), i.p., 1 h prior to exposure on days 1, 4, 7 and 10 of the study. For all groups n=10.

15.4 Sampling Procedures

All mice were killed on day 12, by intra-peritoneal barbiturate anaesthetic overdose, 24 h after final exposure to air or TS. A blood sample was taken over heparin from the sub-clavian vein and the plasma separated by centrifugation and stored at −40° C. A BAL was performed using 0.4 mL of phosphate buffered saline (PBS). Cells recovered from the BAL were used for the total cell and differential cell counts. The BAL supernatants and remaining cell pellet were stored at −40° C. and −80° C. respectively for possible future analysis. Following BAL, the cannula was left tied in place. The heart and lungs were removed after gently opening the thorax and cutting down either side of the sternum and ribs. The left lobe was tied off, removed, snap-frozen and stored at −80° C. The right lobe was inflated with 10% phosphate buffered formalin (PBF) to a pressure of 18 cm of PBF for 20 minutes. The trachea was then ligated below the cannula and the cannula removed. The heart, lung & trachea were immersed in PBF.

15.5 Data Measurement and Statistical Analysis

Results are presented as individual data points for each animal and the mean value calculated for each group.

The data were therefore initially subjected to a one-way analysis of variance test (ANOVA), followed by a Bonferroni correction for multiple comparisons in order to test for statistically significant differences between treatment groups. A "p" value of <0.05 was considered to be statistically significant.

Percentage inhibitions were calculated using the formula below:

$$\%\ \text{Inhibition} = \left(1 - \left(\frac{\text{Treatment group result} - \text{sham group result}}{TS\ \text{vehicle group result} - \text{sham group result}}\right)\right) \times 100$$

15.6 Results 15.6.1 Pulmonary Inflammation, as Indicated by the Increase in Cell Numbers Recovered in the BAL, Induced by Daily Exposures to TS One group was exposed to TS daily for 11 days and received vehicle (D-PBS), i.p., 1 h prior TS-exposure on days 1, 4, 7 and 10 of the study. When compared to a similarly treated air-exposed group, mice exhibited pulmonary inflammation presented as a significant increase (p<0.001) in the total number of cells recovered in BAL at sacrifice on day 12 (24 h after the last TS-exposure). This inflammation consisted of significant increases in the numbers of macrophages, epithelial cells, neutrophils and lymphocytes (p<0.001 for all), when compared with the air-exposed (sham) animals (Table 2).

TABLE 2

Summary of the effects of TS-exposure for 11 consecutive days on pulmonary inflammatory responses in mice.

| Inflammatory markers | TS-exposure Days 1-11 | |
|---|---|---|
| (BAL) | Fold increase* | p |
| Total Cells | 9.5 | <0.001 |
| Macrophages | 7.3 | <0.001 |
| Epithelial cells | 6.6 | <0.001 |
| Neutrophils | 551.8 | <0.001 |
| Eosinophils | 80.1 | ns |
| Lymphocytes | 96.7 | <0.001 |

*When compared to the air-exposed control group at the same time point.

Data were subjected to ANOVA. A "p" value of <0.05 was considered to be statistically significant.

ns = not statistically significant.

15.6.2 Effect of i.p. Administration of MOR12743 on Pulmonary Inflammation, as Indicated by the Increase in Cell Numbers Recovered in the BAL, Induced by Daily Exposures to TS MOR12743, 5 mg/kg, administered i.p., 1 h prior to TS-exposure on days 1, 4, 7 and 10, significantly inhibited total cell numbers recovered in the BAL (26%, p<0.001) and specifically epithelial cells (52%, p<0.001) and neutrophils (48%, p<0.001). Degree and significance of inhibition are summarised in Table 3.

15.6.3 Effect of i.p. Administration of MOR03207 on Pulmonary Inflammation, as Indicated by the Increase in Cell Numbers Recovered in the BAL, Induced by Daily Exposures to TS MOR12743, 5 mg/kg, administered i.p., 1 h prior to TS-exposure on days 1, 4, 7 and 10, did not significantly inhibit total cell numbers recovered in the BAL, or the numbers of any specifically identified cell-type elevated following TS-exposure. Data are summarised in Table 3.

15.6.4 Effect of Oral Administration of Roflumilast on Pulmonary Inflammation, as Indicated by the Increase in Cell Numbers Recovered in the BAL, Induced by Daily Exposures to TS Roflumilast, 5 mg/kg, administered p.o., 1 h prior to each TS-exposure, significantly inhibited the total cell numbers recovered in the BAL (32% p<0.001) and specifically epithelial cells (50% p<0.001), neutrophils (56% p<0.001) and lymphocytes (54% p<0.01). Degree and significance of inhibition are summarised in Table 3.

TABLE 3

Summary of the effects of MOR12743, MOR03207 and Roflumilast on the TS-induced inflammatory responses in mice.

| | Compound | | | | | |
|---|---|---|---|---|---|---|
| | MOR12743 | | MOR03207 Treatment | | Roflumilast | |
| | 5 mg/kg i.p. on days 1, 4, 7, & 10. | | 5 mg/kg i.p. on days 1, 4, 7, & 10. | | 5 mg/kg p.o. q.d. | |
| Inhibition | % | p value | % | p value | % | p value |
| Total cells | 26 | <0.001 | 0 | ns | 32 | <0.001 |
| Macrophages | 6 | ns | −3 | ns | 13 | <0.001 |
| Epithelial Cells | 52 | <0.001 | 8 | ns | 50 | <0.001 |
| Neutrophils | 48 | <0.001 | −1 | ns | 56 | <0.001 |
| Lymphocytes | 24 | ns | 20 | ns | 54 | <0.01 |
| Eosinophils | No statistically significant increase following TS-exposure | | | | | |

All data were subjected to an ANOVA test for comparisons in order to test for significant differences between treatment groups.

A "p" value of <0.05 was considered to be statistically significant.

ns = not statistically significant.

15.6.5 Effect of Treatment on Bodyweights of Mice Throughout the Eleven Daily Exposures to TS In order to monitor the health of the mice throughout the duration of the exposure protocol, mice were weighed at the start of the study, on day 6 and on day 12 prior to sacrifice. Over the 12 days of the study, sham-exposed mice showed little or no change in bodyweight. All TS-exposed groups showed some loss of bodyweight over this period but these losses were not statistically significant.

15.7 Conclusion

MOR12743 (5 mg/kg), administered i.p., on days 1, 4, 7 and 10, significantly inhibited the total number of cells recovered in BAL and specifically epithelial cells and neutrophils. MOR03207 (5 mg/kg), administered in the same way, had no effect on total cell numbers recovered in BAL, or on the numbers of any specifically identified cell type.

The reference compound, Roflumilast (5 mg/kg), administered p.o., 1 h prior to each TS-exposure, significantly inhibited the total number of cells recovered in BAL and specifically epithelial cells neutrophils and lymphocytes. The response was similar to that seen in previous studies.

All TS-exposed groups showed some bodyweight loss over the 12 day study period but there were no significant differences between any of the treatment groups.

Example 16—Intranasal Instillation of LPS: A Mouse Model of Acute Lung Neutrophilia Two independent studies were conducted with one negative mAb and two positive mAbs in the intranasal instillation of Lipopolysaccharide (LPS) mouse model of acute lung neutrophilia, a model which mimics some relevant aspects of COPD (Chronic Obstructive Pulmonary Disease). The effects were measured by Broncho Alveolar Lavage (BAL) inflammatory cell counting.

16.1 Study Groups

Several groups of mice were treated with different antibodies and Dexamethasone and compared to the mice subjected to LPS only. The summary of the groups is provided in Table 4.

TABLE 4

| | Number of animals in the group | Dose | Route | Frequency | Vehicle |
|---|---|---|---|---|---|
| Saline solution | 5 | — | — | — | — |
| LPS | 10 | 10 μg/mouse | Intranasal | — | saline |
| LPS + DEX | 10 | 30 mg/kg | Per os | Twice per day | MC 0.5% |
| LPS + MOR03207 | 10 | 5 mg/kg | Intra-peritoneally | ONCE | D-PBS |
| LPS + MOR12743 | 10 | 5 mg/kg | Intra-peritoneally | ONCE | D-PBS |
| LPS + MOR12762 | 10 | 5 mg/kg | Intra-peritoneally | ONCE | D-PBS |

16.2 Materials

Lipopolysaccharide (LPS): from *Escherichia coli* 055:B5, ref: L4524-25MG, purified by affinity chromatography lot: 018K4077—Sigma. LPS was prepared by Volume administered by intranasal instillation: 50 μL/mouse (10 μg/50 μL)

Saline solution: sodium chloride 0.9%, lot 9F0191 (endotoxin free, Lavoisier)

Ketamine: Imalgene MERIAL 1000, 10 mL

Xylazine: Rompun BAYER PHARMA 2%, 25 mL

Isoflurane: Aerrane, batch 10E28A35

Methylcellulose (MC): VWR, ref AX021233 batch M1395

Dexamethasone (DEX) preparation: 30 mg/kg, 10 mL/kg, 0.2 mL/mouse, po

Antibodies were frozen, at 1 mg/mL. Test substances were allowed to thaw at 4° C. overnight prior to administration. All antibodies were ready to use upon defrosting (or were diluted extemporaneously).

16.3 Animals

BALB/c female mice from Harlan (France) were used in the study. Mice weight was around 20 g.

16.4 Experimental Procedures

Intranasal Administration

Mice were anesthetized by isoflurane inhalation. During the breathing, LPS was instilled intranasally. After 24 h, mice were anesthetized intra-peritoneally (IP) and Broncho Alveolar Lavage procedure was performed. Mice were anesthetized by injection of anaesthetic solution of 0.1 mL per 10 g of the mouse weight. The anaesthetic solution was composed of 18 ml 0.9% NaCl, 0.5 mL xylazine (5 mg/Kg) and 1.5 mL ketamine (75 mg/Kg).

Bronchoalveolar Lavage (BAL)

The trachea was exposed through midline incision and canulated (with a mice catheter). BAL was performed twice using 1 mL of sterile PBS buffer. Lavage fluid was removed and centrifuged at 1500 rpm for 10 min at 4° C. The cell pellet was resuspended in 200 μL of PBS buffer. The cells were counted using a cell counter (Vet abc, France). The lavage fluid supernatant was kept at −20° C. for inflammation mediators dosing.

16.5 Study Design

Dexamethasone: Treatment with dexamethasone was performed 24, 16 and 1 hour prior to LPS instillation and 6 hours after LPS administration Antibodies: 24 hours before LPS instillation mice were treated with one of the mAbs (MOR03207, MOR12762 or MOR12743).

For all groups, BAL was performed 24 hours after LPS administration and cell counts were measured.

Results

Figure 10:
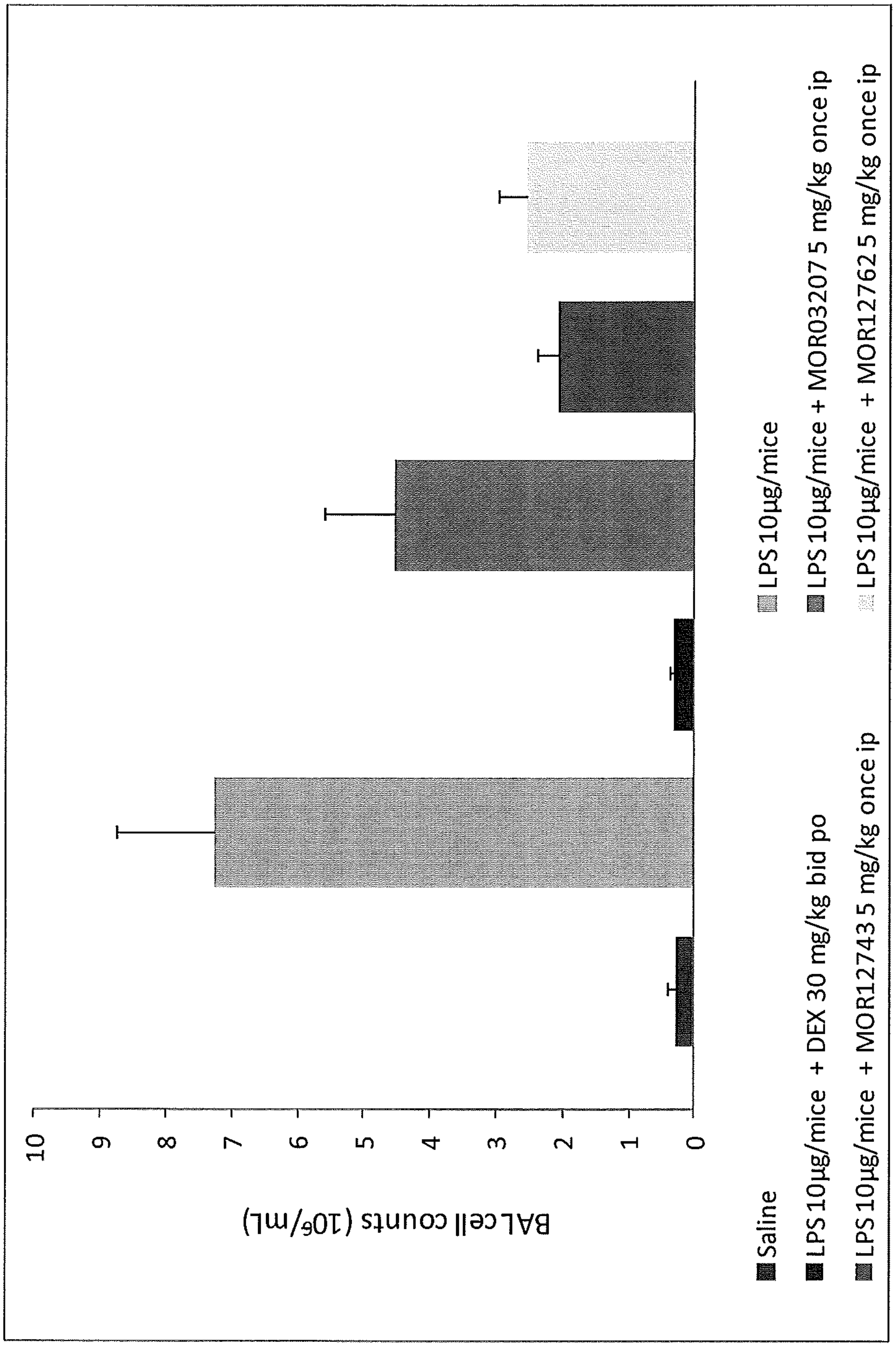
FIG. 10 shows the results of MOR12762 or MOR12743 administration on the recruitment of inflammatory cells into the BALF in a mouse model of acute lung neutrophilia compared to a control antibody (MOR03207).

The results were analyzed using Student t-test. Cell counts from BAL from mice treated with either antibody or Dexamethasone were compared to the cell counts in mice subjected only to LPS. The averages +/−sem of cell counts from the mice in each group were considered. The results are presented in FIG. 10.

Conclusion

Single treatment with MOR03207 antibody (negative control) at 5 mg/kg did not inhibit significantly (ns trend) the recruitment of inflammatory cells into the BALF. At the same time a single treatment with MOR12762 or MOR12743 at 5 mg/kg inhibited significantly the recruitment of inflammatory cells into the BALF. This indicates that IL17C regulates acute neutrophilia and is a therapeutic target for lung diseases such as COPD.

Therefore it is demonstrated for the first time that IL17C antagonists, e.g. IL17C antibodies, are effective in the treatment of inflammatory disorders and diseases.

Example 17—IL17C Expression Profiling in Human Respiratory Tissue

In this study, IL17C expression was measured via quantitative Real Time PCR (qRT-PCR) in different human respiratory tissue types (tertiary bronchus, quaternary bronchus and pulmonary artery) from both control and diseased samples. Control samples were derived from non-smoking and smoking-donors whereas diseased samples were derived from COPD patients, acute/chronic bronchitis patients and patients having lung emphysema.

17.1. RNA Purification and QC

Total RNA was isolated from the frozen tissues using standard methodologies according to the suppliers' protocols, or with in-house adaptations.

QC criteria met (data not shown) were:

Presence of 18S ribosomal RNA

Minimum copy numbers of control gene mRNA transcripts, determined using qRT-PCR, as follows:

β-actin (amplicon length 295 bp) >3,800 transcript copies/100 ng total RNA glyceraldehyde-3-phosphate dehydrogenase (GAPDH, amplicon length 71 bp) >10,000 transcript copies/100 ng total RNA no DNA contamination 17.2 Treatment of RNA Samples with DNase Total RNA was treated with RNase-free DNase I to remove any residual genomic DNA (gDNA). To test for successful removal of DNA from RNA samples, qPCR was done without prior reverse transcription. The absence of an amplification signal confirmed that the RNA samples were free of DNA.

17.3 Primer Probe Sets

The primer probe sets used for qRT-PCR are shown below:

IL17C Amplicon size: 72 bp

```
Forward primer:
                                   (SEQ ID NO: 184)
5'-ATGAGGACCGCTATCCACAGA-3'

Reverse primer:
                                   (SEQ ID NO: 185)
5'-CCCGTCCGTGCATCGA-3'

Probe:
                                   (SEQ ID NO: 186)
5'-TGGCCTTCGCCGAGTGCCTG-3'
```

The probe was labeled at the 5'-end with 6-carboxyfluorescein (FAM) and at the 3'-end with 6-carboxy-tetramethylrhodamine (TAMRA).

17.4 cDNA Synthesis

DNased RNA was incubated with the reverse primers for beta 1, beta 2, beta 3 and GAPDH in reverse transcription buffer, with the samples being heated to 72° C. (to remove secondary structure) and then cooled to 55° C. (to anneal the primers). MuLV reverse transcriptase and nucleotides were added and the reaction mixes were incubated for 30 minutes at 37° C. to allow cDNA synthesis to occur. The samples were then heated to 90° C. for 5 minutes to denature the reverse transcriptase.

17.5 qRT-PCR

Multiplexing methodology-using qRT-PCR for simultaneous measurement of mRNA levels of the genes of interest and GAPDH was used. The simultaneous measurement of GAPDH in each assay tube provided a QC check for successful reverse transcription and qRT-PCR. The reactions were performed with cDNA derived from 50 ng of total RNA. Forward and reverse primers and probes for each target and GAPDH were added to the reaction mix along with nucleotides, buffer and AmpliTaq Gold™ Taq polymerase. The PCR conditions were: 94° C. for 12 minutes (enzyme activation step), followed by 40 cycles of 94° C. for 15 seconds (denaturing step) and 60° C. for 30 seconds (to anneal and extend). Following sensitivity testing, the initial PCR temperature for beta 3 was increased to 97° C.

Results

Figure 11:
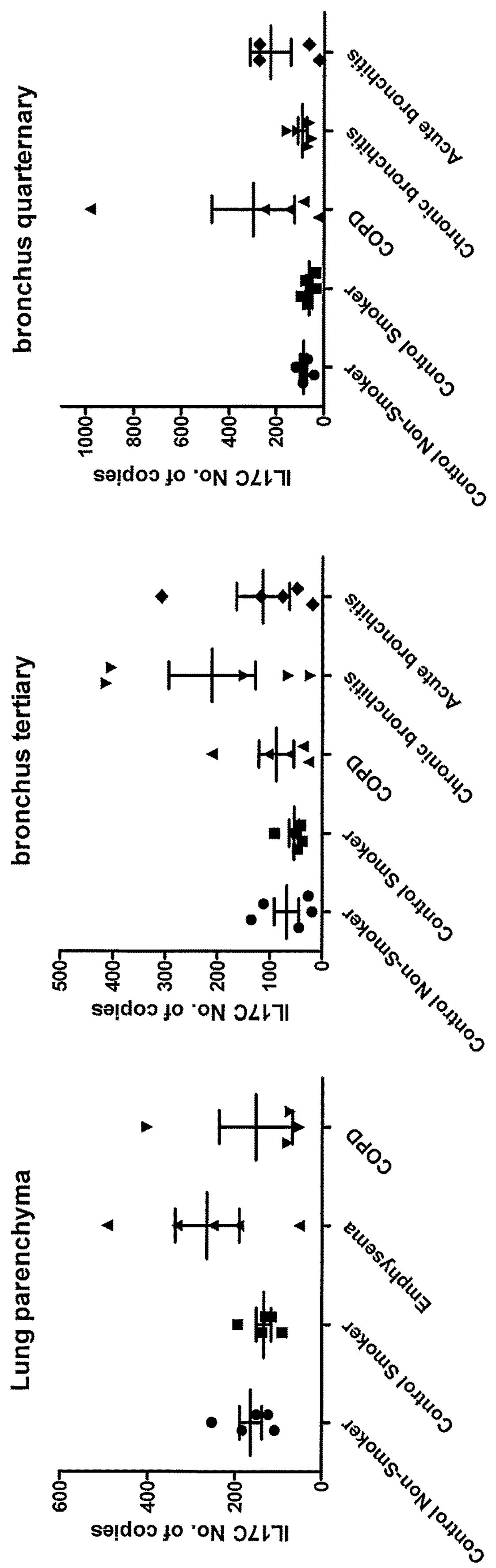
FIG. 11 shows the results of IL17C expression profiling using qRT-PCR. Increased IL17C expression levels were detected in lung tissue samples derived from donors with diagnosed inflammatory respiratory diseases in comparison to IL17C expression levels in the control samples. Samples from 5 individual donors were analyzed for each group.

The data presented here show that IL17C, a member of the interleukin 17 family of pro-inflammatory cytokines, is constitutively expressed in human lung. In addition, increased expression levels of IL17C were observed in lung tissue samples derived from donors with diagnosed inflammatory respiratory diseases like COPD, bronchitis or lung emphysema in comparison to the control samples (FIG. 11).

Example 18—Imiquimod (IMQ) Psoriasis-Like Mouse Model

The pro-inflammatory function of IL17C in the skin was examined in a non-infectious cutaneous inflammation mouse model of psoriasis where topical TLR7-TLR8 agonist Imiquimod induces psoriatic skin lesions characterized by epidermal proliferation and leukocyte infiltration, which are dependent on pathogenic TH17 cytokines (Van der Fits et al., J of Immunol. 2009 May 1; 182(9):5836-45.). The role of IL17C in this particular model was recently documented (Ramirez-Carrozzi et al, Nat Immunol. 2011 12(12):1159-66) and a convincing genetic proof of the IL17C role in the disease model was provided with IL17C$^{-/-}$ mice. The same psoriasis-like model was used to further study the IL17C response to IMQ in the skin and identify the IL17C producing cells.

18.1 Reagents

Vaseline (Vaseline officinale, Cooper) and Imiquimod cream (Aldara, 5% cream, MEDA) were used. The antibodies used were anti-mouse IL17A/F (R&D System, clone 50104, ref MAB421) and anti-mouse IL23p40 (eBioscience, clone C17.8, ref 16-7123-85)

18.2 Animals

Balb/c N mice (female, 18-20 gr, approx. 10 weeks old) were obtained from CERJ or Halan (France). Mice were kept on a 12 hr light/dark cycle (0700-1900). Temperature was maintained at 22° C., and food and water were provided ad libitum.

18.3 Experimental Procedures

In order to induce a psoriatic-like response, a daily topical dose of 62.5 mg of Imiquimod cream on the shaved back and the right ear for 5 consecutive days (D0-D4), translating in a daily dose of 3.13 mg of the active compound. The control group was constituted with mice receiving the same quantity of Vaseline cream. Severity of skin inflammation (erythema, scaling and thickening) was observed every day. Body weight was daily recorded. At necropsy and at the days indicated, the ears and the back skin thicknesses were measured using a micrometer (Mitutoyo). Samples from back and ear skin were collected for histology and gene expression. Spleen and thymus weight was measured.

18.4 Study Design

Mice were randomly divided into equal groups (n=10). The IMQ group received a daily topical dose of 62.5 mg of Imiquimod cream on the shaved back and ear for 5 consecutive days (D0-D4), translating in a daily dose of 3.13 mg of the active compound. The control group was constituted with control mice receiving the same quantity of Vaseline. Antibodies were formulated in PBS, tested at 10 mg/kg (200 ug/mice) and administered i.p., 3 days before and at start of the experiment (D0), therefore, 6 different treatment groups were used:

- Control (Vaseline)
- IMQ (Aldara 5% cream)
- IMQ+MOR03207_h/m 10 mg/kg i.p. (negative control Ab)
- IMQ+MOR12743_h/m 10 mg/kg i.p.
- anti-mouse IL17A/F 10 mg/kg i.p
- anti-mouse IL23p40 10 mg/kg i.p 18.5 Results IL17C protein expression was detected using biotinylated MOR12743 antibodies and IHC. IL17C was expressed in the mast cells of the dermis both in control and IMQ treated groups (data not shown). In response to IMQ, IL17C expression was increased in keratinocytes of the epidermis from D2 to D4—with the higher expression observed at D3—as well as in some smaller inflammatory cells of the dermis and the stratum. MOR03207 (isotype control) displayed no staining whatever the conditions.

This observation was in line with IL17C gene expression. Basal levels were undetectable for IL17A and IL17F and low for IL17C and IL23p19. IL17A, IL17F were maximally increased by IMQ in the back skin after 96 h whereas IL23p19 and IL17C were increased earlier with a maximum at 48 h. IL17RA and IL17RE were well expressed with very moderate expression changes in response to IMQ.

Figure 12:
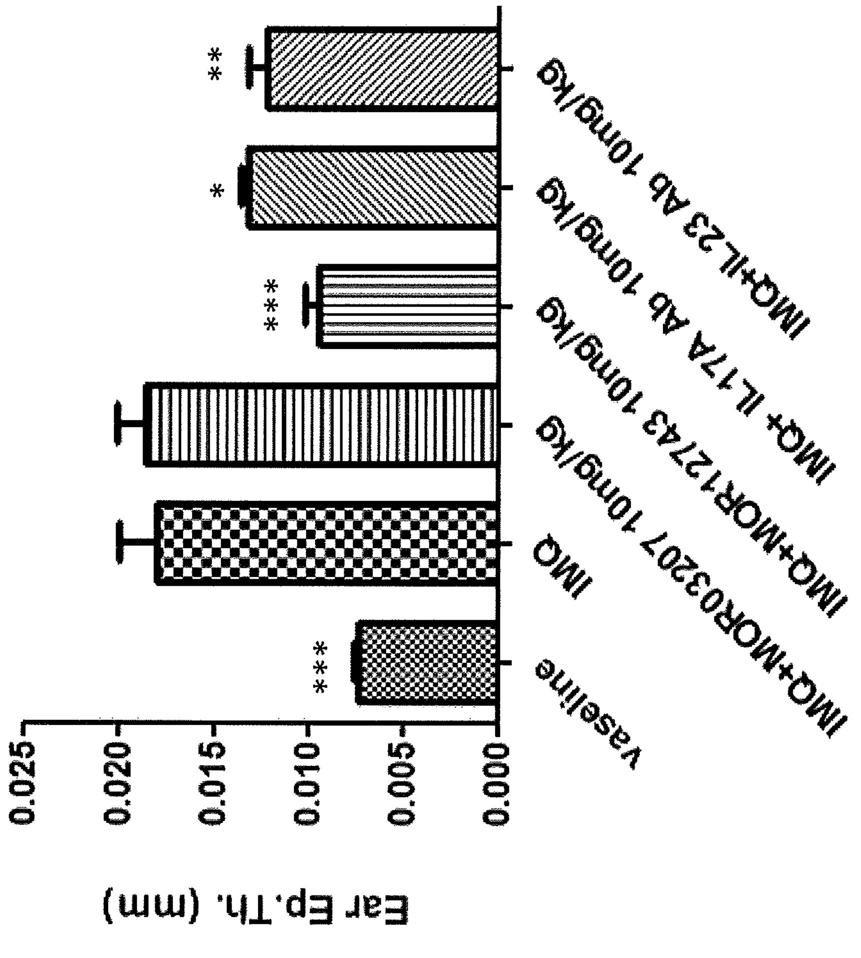
FIG. 12 shows effect of MOR1243 neutralizing antibodies on epidermal thickness in Imiquimod (IMQ) psoriasis-like mouse model.

Effects of neutralizing antibodies relevant to the pathway or specific to IL17C were assessed on the IMQ induced psoriasis by a histological measure of epidermal thickness. IL-17A and IL-23p40 antibodies showed partial preventive effects in line with the common knowledge in the field. The effect of MOR1243 neutralizing antibodies was significant thus demonstrating that IL17C neutralization can significantly prevent the epidermal thickness induced by IMQ in the mouse ear skin (FIG. 12).

Example 19—IL17C Expression and Function in Primary Human Epidermal Keratinocytes To further explore function of IL17C in psoriasis, we focused on IL17C expression and function in primary human epidermal keratinocytes.

19.1 Adult Normal Human Epidermal Keratinocytes (NHEK-Ad) Cultures

Cryopreserved primary normal human epidermal keratinocytes from adult were obtained from Lonza and cultured in Keratinocyte Growth Medium-gold (KGM-Gold™) that was made by supplementing the Keratinocyte Basal Medium-gold (KBM-Gold™) with the various SingleQuots™ of growth factor supplements including bovine pituitary extract, hydrocortisone, hEGF, epinephrine, transferrin, insulin and GA-1000 (media & supplements all from Lonza). Cells that were expanded for 2 more passages were seeded in 96-well plates (25000 c/well) in KGM-Gold™. After overnight culture, medium was removed and changed to KGM-Gold™ w/o hydrocortisone prior to addition of various cytokine triggers. Total RNA was extracted at various time points and expression of IL-17RE, IL17C and ß-defensin-2 (DEF4B) was determined by quantitative RT-PCR. Cell supernatant harvested was kept at −20° C. until analyzed for levels of secreted ß-defensin-2 (hBD2) using ELISA. Recombinant human IL17C was from Novus Biologicals. Recombinant human IL-1ß and TNFα were from PeproTech. Recombinant human IL-17A and IL-22 were from R&D Systems. The following Toll-Like receptor (TLR) agonists were acquired from InvivoGen: flagellin (FLA) purified from *S. typhimurium* (TLR5 agonist), guardiquimod (TLR7 agonist), CL097 (TLR7/8 agonist) and CpG oligonucleotide ODN 2611 (TLR9 agonist). The TLR4 agonist lipopolysacccharide (LPS, from *E. Coli* serotype 026:B6) was obtained from Sigma.

19.2 Quantitative RT-PCR

Total RNA was extracted from cells using the RNeasy Mini Kit (Qiagen) and reverse-transcribed using Taqman® Reverse Transcription Reagents (Applied Biosystems). Twenty-five μl PCR reactions were prepared using Taqman® universal PCR master mix/No AmpErase® UNG and predesigned Assay-on-Demand Gene Expression primer/probe sets (all Applied Biosystems). qPCR was performed on the ABI Prism® 7000 (Applied Biosystems). Gene expression was normalized to the housekeeping gene GAPDH and expressed as ΔCt values, with ΔCt=Ctgene−Ct(GAPDH) or expressed as relative mRNA level of specific gene expression as obtained using the 2-ΔCt method.

19.3 Hbd2 ELISA

The following protocol was developed and validated to measure hBD2 levels using capture and detection antibodies obtained from PeproTech (catno. 900-K172). White Lumitrac 600 384-well plates (Greiner) were coated with 40 μL of anti-hBD2 capture antibody solution (0.5 μg/mL in PBS). After overnight incubation at 4° C., plates were washed once with PBST (PBS+0.05% Tween-20 (Sigma)) and once with PBS and blocked by a 4 hr incubation at room temperature with 100 uL/well blocking buffer (PBS+1% BSA+1% sucrose+0.05% $NaN_3$). Blocking buffer was removed by inverting the plate and tapping it on an absorbent paper. The plate was washed with 100 μL PBST and 100 μL PBS and 35 uL of hBD2 standard or sample was added. After overnight incubation at 4° C., the plates were washed twice with PBST and once with PBS. Subsequently, 35 uL of biotinylated anti-hBD2 detection antibody solution (0.1 μg/mL in PBS containing 1% BSA) was added. After 2 hr incubation at room temperature, plates were washed as described above and incubated with 35 μL Streptavidin-HRP conjugate (Invitrogen, catno. SNN2004) diluted 1/2000 in PBS+1% BSA. After 45 min, plates were washed as described above and incubated for 5 min at room temperature with 50 μL/well BM Chem ELISA Substrate (Roche). Readout was performed on the Luminoscan Ascent Luminometer (Labsystems) with an integration time of 100 msec.

19.4 Results

While IL-17RA is ubiquitously expressed, expression of IL-17RE is more restricted and its expression is particularly high on cells of epithelial origin. We analyzed the expression of IL-17RE mRNA on primary human epidermal keratinocytes and observed high expression of IL-17RE in these cells with ΔCT (IL-17RE, GAPDH) 4-6. Expression of IL-17RE was not modulated by any of the tested inflammatory triggers (data not shown).

Figure 13A:
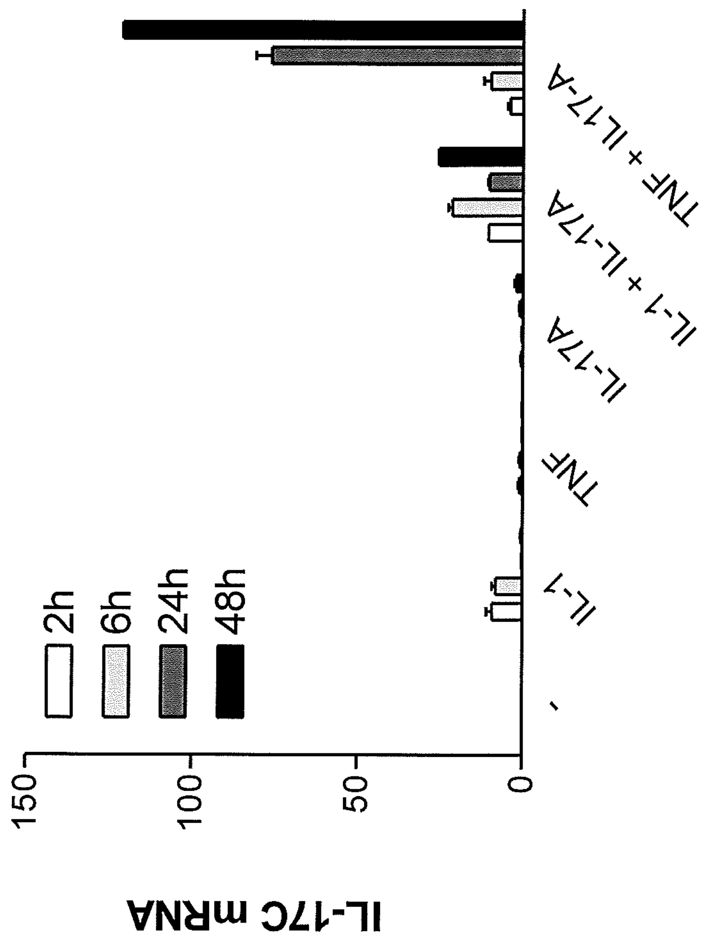
FIG. 13A shows the results of quantitative RT-PCR analysis of IL17C mRNA expression in human epidermal keratinocytes treated for 2 h, 6 h, 24 h or 48 h with medium alone, IL-1 (10 ng/mL), TNF (10 ng/mL), IL-17A (250 ng/mL) or combinations of these triggers.
Figure 13B:
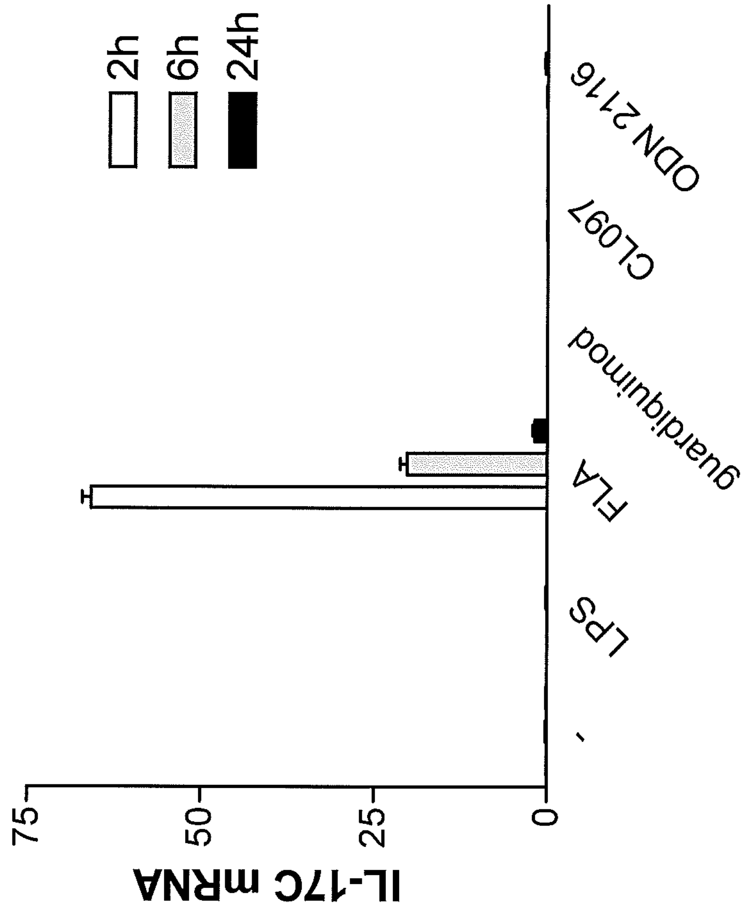
FIG. 13B shows results of quantitative RT-PCR analysis of IL-17C mRNA expression in human epidermal keratinocytes treated for 2 h, 6 h or 24 h with medium alone or various TLR ligands: TLR4 ligand LPS (1 μg/mL), TLR5 ligand flagellin (1 μg/mL), TLR7 ligand guardiquimod (4 μg/mL), TLR7/8 ligand CL097 (10 μg/mL) and TLR9 ligand CpG ODN 2116 (10 μM).

We further extended these initial findings and also analyzed the regulation of IL17C expression in keratinocytes by IL-17A, a cytokine produced by Th17 cells and known to play an important role in psoriasis. The obtained data confirm induction of IL17C mRNA by IL-1 and by flagellin, a TLR5 agonist (FIGS. 13A and 13B). Ligand of other TLRs (TLR4, TLR7, TLR8 or TLR9) did not significantly induce IL17C mRNA. Kinetic analysis showed that the induction of IL17C mRNA by IL-1 or Flagelin was rapid and transient. Interestingly, while IL-17A did not significantly induce IL17C mRNA on its own, it synergistically boosted and sustained the expression of IL17C over time when combined with the pro-inflammatory cytokines TNF or IL-1 (FIG. 13A).

As keratinocytes express high levels of IL-17RE, function of IL17C in these cells was further examined. Although human primary keratinocytes did not respond to IL17C alone, IL17C did stimulate expression of R-defensin-2 in synergy with other tested pro-inflammatory genes i.e. IL-1ß, TNFα and IL-22. Synergistic stimulation of ß-defensin-2 mRNA expression was observed both at level of mRNA and protein.

19.5 Summary

Overall, data indicate that IL17C produced by proinflammatory cytokines in keratinocytes could play a role in a positive feed forward loop that amplifies and sustains inflammatory gene expression in keratinocytes contributing to psoriasis skin inflammation.

Example 20: ELISA-Based Cross-Competition Assay

Cross-competition of an anti-IL17C antibody or another IL17C binding agent may be detected by using an ELISA assay according to the following standard procedure. Likewise, cross-competition of an anti-IL17C antibody or another IL17C binding agent may be detected.

The general principle of the ELISA-assay involves coating of an anti-IL17C antibody onto the wells of an ELISA plate. An excess amount of a second, potentially cross-competitive, anti-IL17C antibody is then added in solution (i.e. not bound to the ELISA plate). Subsequently a limited amount of IL17C-Fc is then added to the wells.

The antibody which is coated onto the wells and the antibody in solution will compete for binding of the limited number of IL17C molecules. The plate is then washed to remove IL17C molecules that has not bound to the coated antibody and to also remove the second, solution phase antibody as well as any complexes formed between the second, solution phase antibody and IL17C. The amount of bound IL17C is then measured using an appropriate IL17C detection reagent. Therefore, IL17C may be fused with a tag, e.g. Fc, Flag, etc. which can be detected via an appropriate tag-specific antibody.

An antibody in solution that is cross-competitive to the coated antibody will be able to cause a decrease in the number of IL17C molecules that the coated antibody can bind relative to the number of IL17C molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y IL17C binding sites per well are at least 10 fold higher than the moles of Ab-X IL17C binding sites that are used, per well, during the coating of the ELISA plate. IL17C is then added such that the moles of IL17C added per well were at least 25-fold lower than the moles of Ab-X IL17C binding sites that are used for coating each well. Following a suitable incubation period, the ELISA plate is washed and a IL17C detection reagent is added to measure the amount of IL17C molecules specifically bound by the coated anti-IL17C antibody (in this case Ab-X). The background signal for the assay is defined as the signal obtained in wells with the coated antibody (in this case Ab-X), second solution phase antibody (in this case Ab-Y), buffer only (i.e. no IL17C) and IL17C detection reagents. The positive control signal for the assay is defined as the signal obtained in wells with the coated antibody (in this case Ab-X), second solution phase antibody buffer only (i.e. no second solution phase antibody), IL17C detection reagents. The ELISA assay needs to be run in such a manner so as to have the positive control signal be at least 6 times the background signal.

To avoid any artifacts (e.g. significantly different affinities between Ab-X and Ab-Y for IL17C) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

The invention claimed is:

1. An isolated antibody or antibody fragment specific for Interleukin 17C (IL-17C), wherein said antibody:

a) is monoclonal
b) is of the IgG isotype;
c) comprises a human light chain variable region and a human heavy chain variable region;
d) has an $IC_{50}$ less than 100 pM for blocking the binding of mouse IL-17C to mouse interleukin 17 receptor E (IL-17RE);
e) binds mouse IL-17C with a $K_D$ less than 3 nM;
f) has an $EC_{50}$ value on mouse IL-17C between 200 and 1200 pM; and
g) has a coefficient of variation ≤20% in a murine serum stability assay.

2. A method for treating an inflammatory disorder, comprising administering to a subject in need thereof an effective amount of a pharmaceutical composition comprising an isolated monoclonal IgG antibody or antibody fragment specific for Interleukin 17C (IL-17C), wherein the inflammatory disorder is lung neutrophilia, pulmonary inflammation, bronchitis, emphysema, arthritis, psoriasis or chronic obstructive pulmonary disease (COPD), and wherein said antibody:

a) comprises a human light chain variable region and a human heavy chain variable region;
b) has an $IC_{50}$ less than 100 pM for blocking the binding of mouse IL-17C to mouse interleukin 17 receptor E (IL-17RE);
c) binds mouse IL-17C with a $K_D$ less than 3 nM;
d) has an $EC_{50}$ value on mouse IL-17C between 200 and 1200 pM; and
e) has a coefficient of variation ≤20% in a murine serum stability assay.

3. The method according to claim 2 wherein the inflammatory disorder is lung neutrophilia, pulmonary inflammation, bronchitis, emphysema, or chronic obstructive pulmonary disease (COPD).

4. The method according to claim 3, wherein the inflammatory disorder is arthritis.

5. The method according to claim 3, wherein the inflammatory disorder is psoriasis.

6. The method according to claim 2, wherein said antibody or antibody fragment is of the $IgG_{2a}$ or of the $IgG_1$ isotype.

7. The method according to claim 2, wherein said effective amount of said antibody or antibody fragment is 5 mg/kg-10 mg/kg.

8. The method according to claim 2, wherein said antibody or antibody fragment is an antibody fragment selected from the group consisting of a Fab, F(ab2)', F(ab)2', and scFV.

* * * * *